US008326420B2

(12) United States Patent
Skelton et al.

(10) Patent No.: US 8,326,420 B2
(45) Date of Patent: Dec. 4, 2012

(54) ASSOCIATING THERAPY ADJUSTMENTS WITH POSTURE STATES USING STABILITY TIMERS

(75) Inventors: Dennis M. Skelton, Bloomington, MN (US); Jon P. Davis, St. Michael, MN (US)

(73) Assignee: Medtronic, Inc., Minneapolis, MN (US)

( * ) Notice: Subject to any disclaimer, the term of this patent is extended or adjusted under 35 U.S.C. 154(b) by 485 days.

(21) Appl. No.: 12/433,808

(22) Filed: Apr. 30, 2009

(65) Prior Publication Data
US 2010/0010590 A1   Jan. 14, 2010

Related U.S. Application Data

(60) Provisional application No. 61/080,002, filed on Jul. 11, 2008.

(51) Int. Cl.
*A61N 1/00* (2006.01)
(52) U.S. Cl. ............. 607/17; 607/18; 607/19; 607/30; 607/32; 607/62
(58) Field of Classification Search .............. 600/481, 600/529, 544, 546; 607/17, 30, 62
See application file for complete search history.

(56) References Cited

U.S. PATENT DOCUMENTS

| 4,297,685 | A | 10/1981 | Brainard, II |
| 4,365,633 | A | 12/1982 | Loughman |
| 4,543,955 | A | 10/1985 | Schroeppel |
| 4,550,736 | A | 11/1985 | Broughton et al. |
| 4,566,456 | A | 1/1986 | Koning et al. |
| 4,771,780 | A | 9/1988 | Sholder |
| 4,776,345 | A | 10/1988 | Cohen et al. |
| 4,846,180 | A | 7/1989 | Buffet |
| 4,846,195 | A | 7/1989 | Alt |
| 5,031,618 | A | 7/1991 | Mullett |
| 5,040,534 | A | 8/1991 | Mann et al. |
| 5,040,536 | A | 8/1991 | Riff |
| 5,058,584 | A | 10/1991 | Bourgeois |
| 5,125,412 | A | 6/1992 | Thornton |
| 5,154,180 | A | 10/1992 | Blanchet et al. |
| 5,158,078 | A | 10/1992 | Bennett et al. |

(Continued)

FOREIGN PATENT DOCUMENTS
DE   19831109   1/2000
(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Niketa Patel
*Assistant Examiner* — Lindsey G Hankins
(74) *Attorney, Agent, or Firm* — Shumaker & Sieffert, P.A.

(57) ABSTRACT

The disclosure describes techniques for associating therapy adjustments with posture states using stability timers. The techniques may include detecting a patient adjustment to electrical stimulation therapy delivered to the patient, sensing a posture state of the patient, and associating the detected adjustment with the sensed posture state if the sensed posture state is sensed within a first period following the detection of the adjustment and if the sensed posture state does not change during a second period following the sensing of the sensed posture state.

35 Claims, 39 Drawing Sheets

U.S. PATENT DOCUMENTS

| | | |
|---|---|---|
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |

| | | | | | | |
|---|---|---|---|---|---|---|
| 7,308,311 B2 | 12/2007 | Sorensen et al. | | 2005/0177192 A1 | 8/2005 | Rezai et al. |
| 7,313,440 B2 | 12/2007 | Miesel | | 2005/0209511 A1 | 9/2005 | Heruth et al. |
| 7,317,948 B1 | 1/2008 | King et al. | | 2005/0209512 A1 | 9/2005 | Heruth et al. |
| 7,330,760 B2 | 2/2008 | Heruth et al. | | 2005/0209513 A1 | 9/2005 | Heruth et al. |
| 7,366,569 B2 | 4/2008 | Belalcazar | | 2005/0209643 A1 | 9/2005 | Heruth et al. |
| 7,366,572 B2 | 4/2008 | Heruth et al. | | 2005/0209644 A1 | 9/2005 | Heruth et al. |
| 7,387,610 B2 | 6/2008 | Stahmann et al. | | 2005/0209645 A1 | 9/2005 | Heruth et al. |
| 7,389,147 B2 | 6/2008 | Wahlstrand et al. | | 2005/0215847 A1 | 9/2005 | Heruth et al. |
| 7,395,113 B2 | 7/2008 | Heruth | | 2005/0215947 A1 | 9/2005 | Heruth et al. |
| 7,403,820 B2 | 7/2008 | DiLorenzo | | 2005/0216064 A1 | 9/2005 | Heruth et al. |
| 7,406,351 B2 | 7/2008 | Wesselink | | 2005/0222522 A1 | 10/2005 | Heruth et al. |
| 7,415,308 B2 | 8/2008 | Gerber et al. | | 2005/0222638 A1 | 10/2005 | Foley et al. |
| 7,447,545 B2 | 11/2008 | Heruth et al. | | 2005/0228455 A1 | 10/2005 | Kramer et al. |
| 7,471,290 B2 | 12/2008 | Wang et al. | | 2005/0234514 A1 | 10/2005 | Heruth et al. |
| 7,471,980 B2 | 12/2008 | Koshiol | | 2005/0234518 A1 | 10/2005 | Heruth et al. |
| 7,489,970 B2 | 2/2009 | Lee et al. | | 2005/0240242 A1 | 10/2005 | DiLorenzo |
| 7,491,181 B2 | 2/2009 | Heruth et al. | | 2005/0245988 A1 | 11/2005 | Miesel |
| 7,505,815 B2 | 3/2009 | Lee et al. | | 2005/0283210 A1 | 12/2005 | Blischak et al. |
| 7,519,431 B2 | 4/2009 | Goetz et al. | | 2006/0190049 A1 | 8/2006 | Gerber et al. |
| 7,542,803 B2 | 6/2009 | Heruth et al. | | 2006/0190050 A1 | 8/2006 | Gerber et al. |
| 7,548,786 B2 | 6/2009 | Lee et al. | | 2006/0190051 A1 | 8/2006 | Gerber et al. |
| 7,559,901 B2 | 7/2009 | Maile | | 2006/0195051 A1 | 8/2006 | Schnapp et al. |
| 7,572,225 B2 | 8/2009 | Stahmann | | 2006/0206167 A1 | 9/2006 | Flaherty et al. |
| 7,577,479 B2 | 8/2009 | Hartley et al. | | 2006/0212080 A1 | 9/2006 | Hartley et al. |
| 7,580,752 B2 | 8/2009 | Gerber et al. | | 2006/0213267 A1 | 9/2006 | Tronconi et al. |
| 7,584,808 B2 | 9/2009 | Dolgin et al. | | 2006/0235289 A1 | 10/2006 | Wesselink et al. |
| 7,590,453 B2 | 9/2009 | Heruth | | 2006/0235472 A1 | 10/2006 | Goetz et al. |
| 7,590,455 B2 | 9/2009 | Heruth et al. | | 2006/0241513 A1 | 10/2006 | Hatlestad et al. |
| 7,590,481 B2 | 9/2009 | Lu et al. | | 2006/0247732 A1 | 11/2006 | Wesselink |
| 7,591,265 B2 | 9/2009 | Lee et al. | | 2006/0247739 A1 | 11/2006 | Wahlstrand et al. |
| 7,603,170 B2 | 10/2009 | Hatlestad et al. | | 2006/0259099 A1 | 11/2006 | Goetz et al. |
| 7,623,919 B2 | 11/2009 | Goetz et al. | | 2006/0262120 A1 | 11/2006 | Rosenberg |
| 7,634,379 B2 | 12/2009 | Noble | | 2006/0265025 A1 | 11/2006 | Goetz et al. |
| 7,664,546 B2 | 2/2010 | Hartley et al. | | 2006/0287686 A1 | 12/2006 | Cullen et al. |
| 7,672,806 B2 | 3/2010 | Tronconi | | 2007/0015976 A1 | 1/2007 | Miesel et al. |
| 7,717,848 B2 | 5/2010 | Heruth et al. | | 2007/0038265 A1 | 2/2007 | Tcheng et al. |
| 7,769,464 B2 | 8/2010 | Gerber et al. | | 2007/0050715 A1 | 3/2007 | Behar |
| 7,792,583 B2 | 9/2010 | Heruth et al. | | 2007/0073355 A1 | 3/2007 | DiLorenzo et al. |
| 2002/0038137 A1 | 3/2002 | Stein | | 2007/0115277 A1 | 5/2007 | Wang et al. |
| 2002/0091308 A1 | 7/2002 | Kipshidze et al. | | 2007/0118056 A1 | 5/2007 | Wang et al. |
| 2002/0107553 A1 | 8/2002 | Hill et al. | | 2007/0123758 A1 | 5/2007 | Miesel et al. |
| 2002/0115939 A1 | 8/2002 | Mulligan et al. | | 2007/0129622 A1 | 6/2007 | Bourget et al. |
| 2002/0165586 A1 | 11/2002 | Hill et al. | | 2007/0129641 A1 | 6/2007 | Sweeney |
| 2002/0169485 A1 | 11/2002 | Pless et al. | | 2007/0129769 A1 | 6/2007 | Bourget et al. |
| 2002/0170193 A1 | 11/2002 | Townsend et al. | | 2007/0129774 A1 | 6/2007 | Bourget et al. |
| 2003/0004423 A1 | 1/2003 | Lavie et al. | | 2007/0150026 A1 | 6/2007 | Bourget et al. |
| 2003/0036783 A1 | 2/2003 | Bauhahn et al. | | 2007/0150029 A1* | 6/2007 | Bourget et al. ............ 607/62 |
| 2003/0045910 A1 | 3/2003 | Sorensen et al. | | 2007/1050026 | 6/2007 | Bourget |
| 2003/0065370 A1 | 4/2003 | Lebel et al. | | 2007/0213789 A1 | 9/2007 | Nolan et al. |
| 2003/0088185 A1 | 5/2003 | Prass | | 2007/0249968 A1 | 10/2007 | Miesel et al. |
| 2003/0149457 A1 | 8/2003 | Tcheng et al. | | 2007/0250121 A1 | 10/2007 | Miesel et al. |
| 2003/0171791 A1 | 9/2003 | KenKnight et al. | | 2007/0250134 A1 | 10/2007 | Miesel et al. |
| 2003/0181960 A1 | 9/2003 | Carter et al. | | 2007/0255118 A1 | 11/2007 | Miesel et al. |
| 2003/0204211 A1 | 10/2003 | Condie et al. | | 2007/0255154 A1 | 11/2007 | Lu et al. |
| 2004/0015103 A1 | 1/2004 | Aminian et al. | | 2007/0265664 A1 | 11/2007 | Gerber et al. |
| 2004/0049132 A1 | 3/2004 | Barron et al. | | 2007/0265681 A1 | 11/2007 | Gerber et al. |
| 2004/0088020 A1 | 5/2004 | Condie et al. | | 2007/0276439 A1 | 11/2007 | Miesel et al. |
| 2004/0102814 A1 | 5/2004 | Sorensen et al. | | 2007/0293737 A1 | 12/2007 | Heruth et al. |
| 2004/0133248 A1 | 7/2004 | Frei et al. | | 2007/0293917 A1 | 12/2007 | Thompson |
| 2004/0138716 A1 | 7/2004 | Kon et al. | | 2008/0071150 A1 | 3/2008 | Miesel et al. |
| 2004/0147975 A1 | 7/2004 | Popovic et al. | | 2008/0071324 A1 | 3/2008 | Miesel et al. |
| 2004/0199215 A1 | 10/2004 | Lee et al. | | 2008/0071326 A1 | 3/2008 | Heruth et al. |
| 2004/0199216 A1 | 10/2004 | Lee et al. | | 2008/0071327 A1 | 3/2008 | Miesel et al. |
| 2004/0199217 A1 | 10/2004 | Lee et al. | | 2008/0079444 A1 | 4/2008 | Denison |
| 2004/0199218 A1 | 10/2004 | Lee et al. | | 2008/0081958 A1 | 4/2008 | Denison et al. |
| 2004/0215286 A1 | 10/2004 | Stypulkowski | | 2008/0114219 A1 | 5/2008 | Zhang et al. |
| 2004/0220621 A1 | 11/2004 | Zhou et al. | | 2008/0164979 A1 | 7/2008 | Otto |
| 2004/0225332 A1 | 11/2004 | Gebhardt et al. | | 2008/0177355 A1 | 7/2008 | Miesel et al. |
| 2004/0257693 A1 | 12/2004 | Ehrlich | | 2008/0188901 A1 | 8/2008 | Sanghera et al. |
| 2005/0042589 A1 | 2/2005 | Hatlestad et al. | | 2008/0188909 A1 | 8/2008 | Bradley |
| 2005/0043767 A1 | 2/2005 | Belalcazar | | 2008/0194998 A1 | 8/2008 | Holmstrom et al. |
| 2005/0060001 A1 | 3/2005 | Singhal et al. | | 2008/0204255 A1 | 8/2008 | Flexer et al. |
| 2005/0061320 A1 | 3/2005 | Lee et al. | | 2008/0269812 A1 | 10/2008 | Gerber et al. |
| 2005/0113710 A1 | 5/2005 | Stahmann et al. | | 2008/0269843 A1 | 10/2008 | Gerber |
| 2005/0113887 A1 | 5/2005 | Bauhahn | | 2008/0281376 A1 | 11/2008 | Gerber et al. |
| 2005/0126026 A1 | 6/2005 | Townsend et al. | | 2008/0281379 A1 | 11/2008 | Wesselink |
| 2005/0137627 A1 | 6/2005 | Koshiol et al. | | 2008/0281381 A1 | 11/2008 | Gerber et al. |
| 2005/0145246 A1 | 7/2005 | Hartley et al. | | 2008/0288200 A1 | 11/2008 | Noble |
| 2005/0172311 A1 | 8/2005 | Hjelt et al. | | 2008/0300449 A1 | 12/2008 | Gerber et al. |

| | | | |
|---|---|---|---|
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| DE | 10024103 | 11/2001 |
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006, 5 pp., http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems, "ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Kitchin et al., "Compensating for the 0 g Offset Drift of the ADXL50 Accelerometer," Analog Devices Application Note AN-380, 2 pp.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp., 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http ://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99-$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/49219: Invitation to Pay Additional Fees dated Oct. 12, 2009, 6 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Notification of Transmittal of the International Search Report and the Written Opinion for corresponding PCT Application No. PCT/US2009/049219, (26 pgs.).
Office Action dated mar. 22, 2012 for U.S. Appl. No. 12/433,750, (10 pgs.).
Responsive Amendment dated Dec. 28, 2011 for U.S. Appl. No. 12/433,756, (14 pgs.).
Office Action dated Apr. 6, 2011 for U.S. Appl. No.12/433,520, (10 pgs).
Responsive Amendment dated Jun. 30, 2011 for U.S. Appl. No. 12/433,520, (17 pgs.).
Office Action dated Sep. 19, 2011 for U.S. Appl. No. 12/433,520, (11 pgs.).
Responsive Amendment dated Nov. 21, 2011 for U.S. Appl. No. 12/433,520, (13 pgs.).
Office Action dated Oct. 6, 2011 for U.S. Appl. No. 12/433,756, (6 pgs.).
Responsive Amendment dated Jun. 21, 2012 for U.S. Appl. No. 12/433,750, (12 pgs.).
Response to Office Action dated Jul. 11, 2012, from U.S. Appl. No. 12/433,756, filed Sep. 28, 2012, 6 pp.

* cited by examiner

ASSOCIATING THERAPY ADJUSTMENTS WITH POSTURE STATES USING STABILITY TIMERS

This application claims the benefit of U.S. Provisional Application No. 61/080,002, titled, "POSTURE STATE DATA COLLECTION AND ASSOCIATED PROGRAMMING" and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure provides a method for associating detected patient therapy adjustments with a posture state and storing the associations. The system may determine the associations intended by the patient through implementation of a posture search timer and a posture stability timer that track therapy adjustments and posture state changes in real time. Since some patients make therapy adjustments in anticipation of changing to a different posture state, instead of making changes once in the desired posture state, these timers may allow the system to correctly associate therapy adjustments to posture states made before the patient engaged in the posture state or current posture states.

The associations of the therapy adjustments with posture states may be used in a record mode for later review. An implantable medical device (IMD) or external programmer may be configured to store multiple therapy adjustments for each posture state and allow a user to find efficacious therapy based upon review of the associations stored for each posture state. The recorded therapy adjustments may be presented as a range of therapy parameters to focus the user on acceptable therapy parameters for each of the posture states. In this manner, the patient and/or physician may be able to fine-tune stimulation therapy for the patient.

The associations of therapy adjustments with posture states also may allow the user to set nominal therapy parameters for a plurality of programs with a single action, such as one click of a confirmation input on an input device of a user interface. The nominal therapy parameters may be previously adjusted values for therapy parameters that support effective therapy. A single action, such as a one-click confirmation, prevents the user from having to set the therapy parameters for each program of each group in each posture state on an individual basis.

Further, in some examples, the system may provide a suggested therapy parameter for each of the plurality of individual programs based upon the therapy adjustment information that includes the associations. The system may implement a guided programming process that is used to generate the suggested therapy parameters and limit programming time needed from the clinician.

In addition, the system may be capable of only associating therapy adjustments that have been intended by the patient for only a particular posture state. If the system recognizes that a received therapy adjustment is outside of a historical range of the prior stored therapy adjustments, the system may not make the association of the therapy adjustment to the posture state. However, the system may prompt the user to confirm the association and only make the association once the confirmation is received.

In one example, the disclosure provides a method comprising detecting a plurality of patient adjustments to electrical stimulation therapy delivered to a patient during multiple instances of a sensed posture state, associating the detected patient adjustments with the sensed posture state of the patient, and storing the associations of the detected patient adjustments with the sensed posture state in a memory.

In another example, the disclosure provides a system comprising an input device that receives a plurality of patient adjustments to electrical stimulation therapy delivered to a patient during multiple instances of a sensed posture state, a processor that associates the received patient adjustments with the sensed posture state of the patient, and a memory that stores the associations of the received patient adjustments with the sensed posture state in a memory.

In another example, the disclosure provides an external programmer for an implantable medical device, the programmer comprising an input device that receives a plurality of patient adjustments to electrical stimulation therapy delivered to the patient by the implantable medical device during multiple instances of a sensed posture state, a telemetry interface that receives a sensed posture state from the implantable medical device and transmits the received patient adjustments to the implantable medical device, a processor that associates the received patient adjustments with the sensed posture state of the patient, and a memory that stores the associations of the received adjustments with the sensed posture state in a memory.

In another example, the disclosure provides An implantable medical device comprising a stimulation generator that delivers electrical stimulation therapy to a patient, a posture sensing module that senses a posture state of the patient, a telemetry interface that receives patient adjustments to the electrical stimulation therapy from an external programmer during multiple instances of a plurality of sensed postured states, a processor that associates the received adjustments with a sensed posture state of the patient, and a memory that stores the associations of the received adjustments with the sensed posture state in a memory.

In another example, the disclosure provides a method comprising detecting a patient adjustment to electrical stimulation therapy delivered to the patient, sensing a posture state of the patient, and associating the detected adjustment with the sensed posture state if the sensed posture state is sensed within a first period following the detection of the adjustment and if the sensed posture state does not change during a second period following the sensing of the sensed posture state.

In another example, the disclosure provides a system comprising a user interface configured to detect a patient adjustment to electrical stimulation therapy delivered to the patient, a posture state module that senses a posture state of the patient, and a processor that associates the detected adjustment with the sensed posture state if the sensed posture state is sensed within a first period following the detection of the adjustment and if the sensed posture state does not change during a second period following the sensing of the sensed posture state.

In another example, the disclosure provides an external programmer for an implantable medical device comprising a user interface that receives patient adjustments to electrical stimulation therapy delivered to the patient by the implantable medical device, a telemetry interface that receives a sensed posture state from the implantable medical device and transmits the received adjustments to the implantable medical device, a processor that associates the detected adjustment with the sensed posture state if the sensed posture state is sensed within a first period following the detection of the adjustment and if the sensed posture state does not change during a second period following the sensing of the sensed posture state, and a memory that stores the associations of the received adjustments with the sensed posture state in a memory.

In another example, the disclosure provides an implantable medical device comprising a stimulation generator that delivers electrical stimulation therapy to a patient, a telemetry interface that receives patient adjustments to the electrical stimulation therapy from an external programmer, a posture sensing module that senses a posture state of the patient, a processor that associates the received adjustments with the sensed posture state if the sensed posture state is sensed within a first period following the receiving of the adjustment and if the sensed posture state does not change during a second period following the sensing of the sensed posture state, and a memory that stores the associations of the received adjustments with the sensed posture state in a memory.

In another example, the disclosure provides a method comprising presenting therapy adjustment information to a user via a user interface, wherein the therapy adjustment information includes one or more therapy adjustments made by a patient to at least one stimulation parameter of one or more stimulation therapy programs for one or more patient posture states, receiving input from the user that selects one or more nominal therapy parameters for each of the therapy programs and for each of the posture states based on the therapy adjustment information, and setting the selected nominal therapy parameters for each of the therapy programs and posture states for use in delivering stimulation therapy to the patient.

In another example, the disclosure provides a system comprising a memory that stores therapy adjustment information that includes one or more therapy adjustments made by a patient to at least one stimulation parameter of one or more stimulation therapy programs for one or more patient posture states, a user interface that presents the therapy adjustment information to a user and receives input from the user that selects one or more nominal therapy parameters for each of the therapy programs and for each of the posture states based on the therapy adjustment information, and a processor that sets the selected nominal therapy parameters for each of the therapy programs and posture states for use in delivering stimulation therapy to the patient.

In another example, the disclosure provides an external programmer for an implantable medical device comprising a user interface that presents therapy adjustment information to a user via a user interface, wherein the therapy adjustment information includes one or more therapy adjustments made by a patient to at least one stimulation parameter of one or more stimulation therapy programs for one or more patient posture states, and receives input from the user that selects one or more nominal therapy parameters for each of the therapy programs and for each of the posture states based on the therapy adjustment information, and a processor that sets the selected nominal therapy parameters for each of the therapy programs and posture states for use in delivering stimulation therapy to the patient.

In another example, the disclosure provides a method comprising receiving therapy adjustment information that includes therapy adjustments made by a patient to at least one parameter of one or more stimulation therapy programs for one or more patient posture states, generating one or more suggested therapy parameters for one or more of the stimulation therapy programs based on the therapy adjustment information, and presenting the suggested therapy parameters to a user.

In another example, the disclosure provides a programming device for an implantable medical device, the programmer comprising a processor configured to generate one or more suggested therapy parameters for one or more stimulation therapy programs delivered by the implantable medical device based on therapy adjustment information, wherein the therapy adjustment information includes therapy adjustments made by a patient to at least one parameter of the stimulation therapy programs for one or more patient posture states, and a user interface that presents the suggested therapy parameters to a user and receives input from the user selecting at least some of the suggested therapy parameters, wherein the processor sets the selected suggested therapy parameters to at least partially define the respective therapy programs for the respective posture states.

In another example, the disclosure provides a method comprising receiving a patient therapy adjustment to a parameter of a therapy program that defines electrical stimulation therapy delivered to the patient, identifying a posture state of the patient, and associating the patient therapy adjustment with the posture state when the patient therapy adjustment is within a range determined based on stored adjustment information for the identified posture state.

In another example, the disclosure provides a system comprising a user interface that receives a patient therapy adjustment to a parameter of a therapy program that defines electrical stimulation therapy delivered to the patient, and a processor that identifies a posture state of the patient, associates the patient therapy adjustment with the posture state when the patient therapy adjustment is within a range determined based on stored adjustment information for the identified posture state.

The details of one or more aspects of the disclosure are set forth in the accompanying drawings and the description below. Other features, objects, and advantages will be apparent from the description and drawings, and from the claims.

DETAILED DESCRIPTION

Figure 1A:
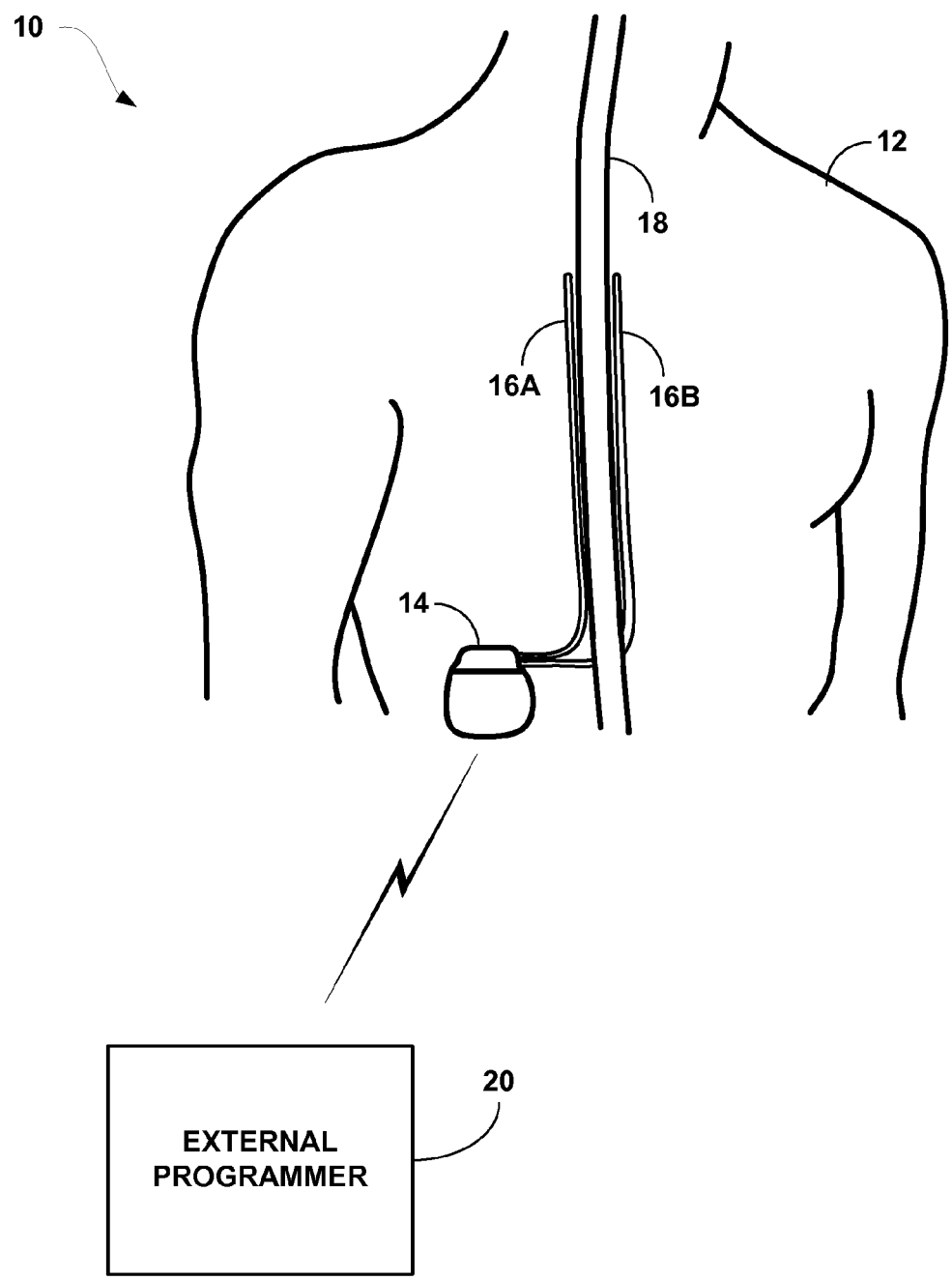
FIG. 1A is a conceptual diagram illustrating an implantable stimulation system including two implantable stimulation leads.

In some medical devices that deliver electrical stimulation therapy, therapeutic efficacy may change as the patient changes between different posture states. In general, a posture state may refer to a patient posture or a combination of posture and activity. For example, some posture states, such as an upright posture state, may be sub-categorized as upright and active or upright and inactive. Other posture states, such as lying down posture states, may or may not have an activity component. Efficacy may refer, in general, to a combination of complete or partial alleviation of symptoms alone, or in combination with some degree of undesirable side effects.

Changes in posture state may cause changes in efficacy due to changes in distances between electrodes or other therapy delivery elements, e.g., due to temporary migration of leads or catheters caused by forces or stresses associated with different postures of the patient, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient to maintain effective stimulation therapy. Therapy parameters may be adjusted individually and directly or by selecting different programs or groups of programs defining different sets of therapy parameters.

A change in efficacy due to changes in posture state may require the patient to continually manage therapy by manually adjusting certain therapy parameters, such as amplitude, pulse rate, pulse width, electrode combination, or electrode polarity, or selecting different therapy programs to achieve more efficacious therapy throughout many different posture states. In some cases, a medical device may employ a posture state detector that detects the patient posture state. The medical device may subsequently adjust therapy parameters in response to different posture states. Therapy adjustments in response to different posture states may be fully automatic, semi-automatic in the sense that a user may provide approval of proposed changes, or user-directed in the sense that the patient may manually adjust therapy based on the posture state indication.

Stimulation therapy may be provided to a patient in order to relieve symptoms from any number of conditions and diseases. An implantable medical device (IMD) that delivers stimulation therapy may also employ a posture state sensor that is configured to sense which posture state the patient is engaged. The sensed posture state may then be associated with therapy adjustments made manually by the patient, i.e., patient adjustments, during the sensed posture state or multiple instances of the sensed posture state to allow a user to review the associations and modify stimulation parameters to better treat the patient.

When the patient makes a patient therapy adjustment, i.e., a change to one of the stimulation parameters that define the stimulation therapy, the therapy adjustment is intended for a particular posture state. Although most therapy adjustments may be made and intended for the posture state currently occupied by the patient, sometimes the patient may anticipate the next posture state and make the manual patient adjustment prior to moving to the intended posture state. Therefore, the system must associate the therapy adjustment with the anticipated posture state that the patient intends to occupy.

To accomplish this association, the system may implement a posture search timer for each instance of a sensed posture state, i.e., each time that a posture state is sensed. The posture search timer may have a search period and a posture stability timer may have a stability period that, when used together, allow the system to associate a therapy adjustment to a later posture state. The therapy adjustment is only associated with the final posture state if the final posture state is sensed within the search period of the posture state timer and continues for at least the stability period of the posture stability timer. In this sense, the system may correctly associate therapy parameters with posture states that the patient intended without making unintended associations.

In another example, the system may enter a record mode that stores associations between therapy adjustments and posture states. The record mode may permit monitoring of patient therapy adjustments for multiple posture states over a period of time to aid in selection of automated therapy adjustments for use in delivery of posture-responsive therapy. Even when a therapy adjustment is made for a therapy program and posture state in which a therapy adjustment has already been made, all previously stored therapy adjustments may be maintained in memory to populate the therapy adjustment information used in the record mode. Association of a therapy adjustment with a posture state may permit a user to identify the posture state for which the patient intended to make the therapy adjustment.

An external programmer, such as a clinician programmer, may present the therapy adjustment information to the user via an output device of a user interface. For example, the presented therapy adjustment information may include minimum and/or maximum amplitude values from the therapy adjustments, the average amplitude value of the therapy adjustments, or the quantified number of therapy adjustments for each therapy program in each posture state. The user may then modify therapy parameters for one or more programs or program groups of programs based upon the presented information.

In other examples, the associations of therapy adjustments to posture states also may allow the user to quickly program stimulation parameters for therapy. An output device of the user interface of an external programmer, e.g., the clinician programmer, may present stimulation parameters, or a nominal therapy parameter, for each of the plurality of therapy programs from the therapy adjustments. The nominal therapy parameter may be a therapy parameter selected from the therapy adjustments stored in the IMD. The nominal therapy adjustment may not be weighted or calculated according to an algorithm. An input device of the user interface may then allow the user to set the presented nominal therapy parameter to all therapy programs by receiving just one confirmation input from the user. The nominal therapy parameter may be the minimum amplitude of the therapy adjustments or the last therapy adjustments used, for example.

An output device of the user interface may also present a suggested therapy parameter based upon the therapy adjustments for each of the individual therapy programs. The user may then select or confirm the suggested therapy parameters for all of the plurality of therapy programs with one confirmation input via an input device of the user interface. Specifically, the suggested therapy parameter may be generated from a guided algorithm created to find the most efficacious therapy for the patient, instead of just a therapy adjustment stored in the IMD. The guided algorithm may implement any one or more of weighted averages, therapy adjustment trends, safe guards to protect against overstimulation, or any other factors. In this manner, the clinician may not be burdened with the time needed to find the most efficacious therapy parameters for the patient, and each time the patient enters a different posture state, the therapy programs will deliver therapy with the most appropriate therapy parameters.

An input device and output device may be referred to collectively as a user interface. In some cases, the input and output devices may be associated with different devices. For example, in some cases, therapy adjustments may be made by a patient via a user interface associated with a patient programmer. Some information, such as information relating to therapy adjustments, postures, and the like, may be presented to a user via a clinician programmer or other device. In other cases, the input and output device may be associated with the same programmer. For example, a clinician programmer may present information relating to therapy adjustments and postures via an output device, and receive programming information from a user via an input device.

In addition, a programmer may be capable of associating therapy adjustments that have been intended by the patient for only a particular posture state. If the programmer recognizes that a received therapy adjustment is outside of a historical range of the prior stored therapy adjustments, the programmer may not make the association of the therapy adjustment to the posture state. However, the programmer may prompt the user to confirm the association and only make the association once the confirmation is received.

Various aspects of the techniques described in this disclosure may be provided in an implantable medical device (IMD), an external programmer for the IMD or a combination of both. For example, processors in the implantable medical device and external programmer may perform various functions such as recording of therapy adjustment associations with particular programs and posture states.

In cases where association is performed by the IMD, therapy adjustments may be transmitted to the IMD from the programmer for not only adjustment of therapy delivered by the IMD, but also for use by the IMD in associating the adjustments with pertinent programs and postures states to support a recording mode for collection of such associations. In cases where association is performed by the external programmer, sensed posture states may be transmitted to the programmer from the IMD for not only recording and presentation of posture states, but also for use by the programmer in associating the adjustments with pertinent programs and postures states to support a recording mode for collection of such associations.

Hence, in many instances, functionality described in this disclosure may be performed by the IMD, the programmer, or a combination of both. Therefore, examples that described particular functionality in the IMD or programmer should not be considered limiting of the techniques, devices and systems, as broadly described in this disclosure.

FIG. 1A is a schematic diagram illustrating an implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1A, system 10 includes an IMD 14 and external programmer 20 shown in conjunction with a patient 12. In the example of FIG. 1A, IMD 14 is an implantable electrical stimulator configured for spinal cord stimulation (SCS), e.g., for relief of chronic pain or other symptoms. Again, although FIG. 1A shows an implantable medical device, other embodiments may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16. The target tissue may be any tissue affected by electrical stimulation energy, such as electrical stimulation pulses or waveforms. Such tissue includes nerves, smooth muscle, and skeletal muscle. In the example illustrated by FIG. 1A, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 may deliver stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a multiple of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, leads 16 may migrate toward IMD 14 when patient 12 bends over, resulting in displacement of electrodes and possible disruption in delivery of effective therapy. Stimulation energy transferred to target tissue may be reduced due to electrode migration, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may need to be decreased to avoid causing patient 12 additional pain or unusual sensations, which may be considered undesirable side effects that undermine overall efficacy.

Also, posture state changes may present changes in symptoms or symptom levels, e.g., pain level. In some examples, to avoid interruptions in effective therapy, IMD 14 may include a posture state module that detects the patient posture state. The IMD automatically adjusts stimulation according to the detected posture state. For example, the posture state module may include one or more accelerometers that detect when patient 12 occupies a posture state in which it is appropriate to decrease the stimulation amplitude, e.g., when patient 12 lies down. The IMD may automatically reduce stimulation amplitude so that patient 12 does not manually have to do so. Example posture states may include "Upright," "Upright and Active," "Lying Down," and so forth.

As will be described in greater detail below, in some examples, IMD 14 may be configured to automatically decrease stimulation amplitude when it detects that patient 12 lies down. The amplitude adjustment may be configured to be decreased at a rate suitable to prevent undesirable effects, e.g., such as the effects due to the compression of leads 16 towards spinal cord 18 when patient 12 lies down. In some examples, IMD 14 may be configured to decrease the stimulation amplitude to a suitable amplitude value substantially immediately upon detection by IMD 14 that patient 12 is lying down. In other examples, the stimulation amplitude may not be decreased substantially immediately by IMD 14 upon detection of patient 12 lying down, but instead IMD 14 may decrease the stimulation amplitude to a suitable amplitude level at a rate of change that is suitable to prevent patient 12 from experiencing undesirable stimulation effects, e.g., due to increased transfer of stimulation energy in the changed anatomical position. In some examples, IMD 14 may substantially instantaneously decrease the stimulation amplitude to a suitable amplitude value when IMD detects that patient 12 is lying down.

Many other examples of reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically adjust stimulation according to the detected posture state. For example, a posture state module may include a posture state sensor, such as an accelerometer, that detects when patient 12 lies down, stands up, or otherwise changes posture.

In response to a posture state indication by the posture state module, IMD 14 may change a program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. The user interface may include an output device for presentation of information, and an input device to receive user input. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

During the delivery of stimulation therapy, patient 12 may make patient therapy adjustments, i.e., patient adjustments to one or more parameters of a therapy via an input device of a user interface of a programmer, to customize the therapy either after patient 12 moves to a different posture state or in anticipation of the next posture state. In examples where IMD 14 is in a record mode to store all patient therapy adjustments associated with a specific posture state, IMD 14 may implement a method to ensure that patient therapy adjustments are associated with the correct posture state intended by patient 12 when the therapy adjustment was made. The patient 12 may occupy the posture state multiple times such that there are multiple instances of the sensed posture state.

Each time the patient 12 occupies the posture state, the patient may enter one or more therapy adjustments. Hence, the multiple therapy adjustments may be obtained over multiple instances of the sensed posture state, i.e., multiple, different times at which the patient occupies the posture state over a time interval, and associated with the posture state.

IMD 14 may use a posture search timer having a search period and a posture stability timer having a stability period after any therapy adjustment in order to match the therapy adjustment to the appropriate posture state. The therapy adjustment is associated with a final posture state only when a final posture state began within the search period of the posture search timer and lasts beyond the stability period of the posture stability timer. In this manner, therapy adjustments are not associated with a posture state that does not remain constant or is not occupied soon enough after the therapy adjustment.

In some cases, external programmer 20 may be characterized as a physician or clinician programmer if it is primarily intended for use by a physician or clinician. In other cases, external programmer 20 may be characterized as a patient programmer if it is primarily intended for use by a patient, e.g., for entry of patient input to specify patient adjustments to one or more therapy parameters. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use, either manually or via other user input media.

External programmer 20 may present posture state data stored in IMD 14 from the detected posture states of patient 12. The posture state data may be acquired by external programmer 20 to generate posture state information, e.g., therapy adjustment information. IMD 14 may also store any associations between the therapy adjustments and the posture states for which the therapy adjustments were intended during a record mode, i.e., therapy adjustment information. By recording all therapy adjustments made for a program in each of the posture states, including each of the multiple instances of the sensed posture states, external programmer 20 may be able to present therapy adjustment information to the user that indicates patient 12 desired stimulation parameters based upon parameter use. For example, the user may be able to identify the most recent stimulation parameters desired by patient 12, the minimum and maximum allowable amplitudes, or even the quantified number of therapy adjustments to indicate that patient 12 is either satisfied with a program or cannot readily find suitable parameters for a program with many therapy adjustments.

The therapy adjustment information stored during the record mode may be presented in any number of different manners. For example, an output device of the user interface may present each program of a group and the respective number of therapy adjustments and the range of such amplitudes defined by the therapy adjustments. Alternatively, an output device of the user interface may also, or instead, present the last (i.e., most recent) amplitude used by patient 12 to deliver therapy with each program. In any manner, the therapy adjustment information may be presented in a graphical, numerical, or textual mode on external programmer 20. The user may be able to customize the presentation of the therapy adjustment information in other examples.

In some examples, external programmer 20 may utilize the associations of the therapy adjustments to posture states in order to further minimize time needed to program all therapy programs. When presenting the amplitude ranges of the therapy adjustments for each therapy program, the user may be able to provide a single confirmation input that sets the amplitude for all programs to some nominal therapy parameter, for example. The nominal therapy parameter may be a minimum amplitude associated with the program and posture state, the last amplitude associated with the program and posture state, or some other therapy parameter already stored by IMD 14 in association with each therapy program and posture state. The therapy parameter may be referred to as nominal in the sense that it refers to a parameter value by a name that is descriptive of the value, rather than to a specific, absolute parameter value. In cases where a program has not been associated with any therapy adjustment, no new stimulation parameter may be programmed to the program.

In other examples, external programmer 20 may generate a suggested therapy parameter based upon the therapy adjustment information and a guided algorithm. The suggested therapy parameter may be a specific therapy parameter value that is visible to the user, but is signified as being suggested by the guided algorithm. The guided algorithm may be an equation, set of equations, look-up table, or other technique for generating a suggested therapy parameter that may define stimulation therapy effective to patient 12. In this manner, external programmer 20 analyzes the therapy adjustment information for the most appropriate stimulation parameters that fit the desires of the user. The guided algorithm may generate a low or high weighted average, a safe average that minimizes the chances of overstimulation, a trend target that weights more recent patient adjustments to therapy greater than older therapy adjustments, or even an intergroup average that looks to therapy adjustments to programs in different groups that provide stimulation therapy. In any case, the user may be able to program the plurality of programs with each suggested therapy parameter with the selection of a single confirmation input.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal tips of leads 16 are one or more electrodes (not shown) that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Figure 1B:
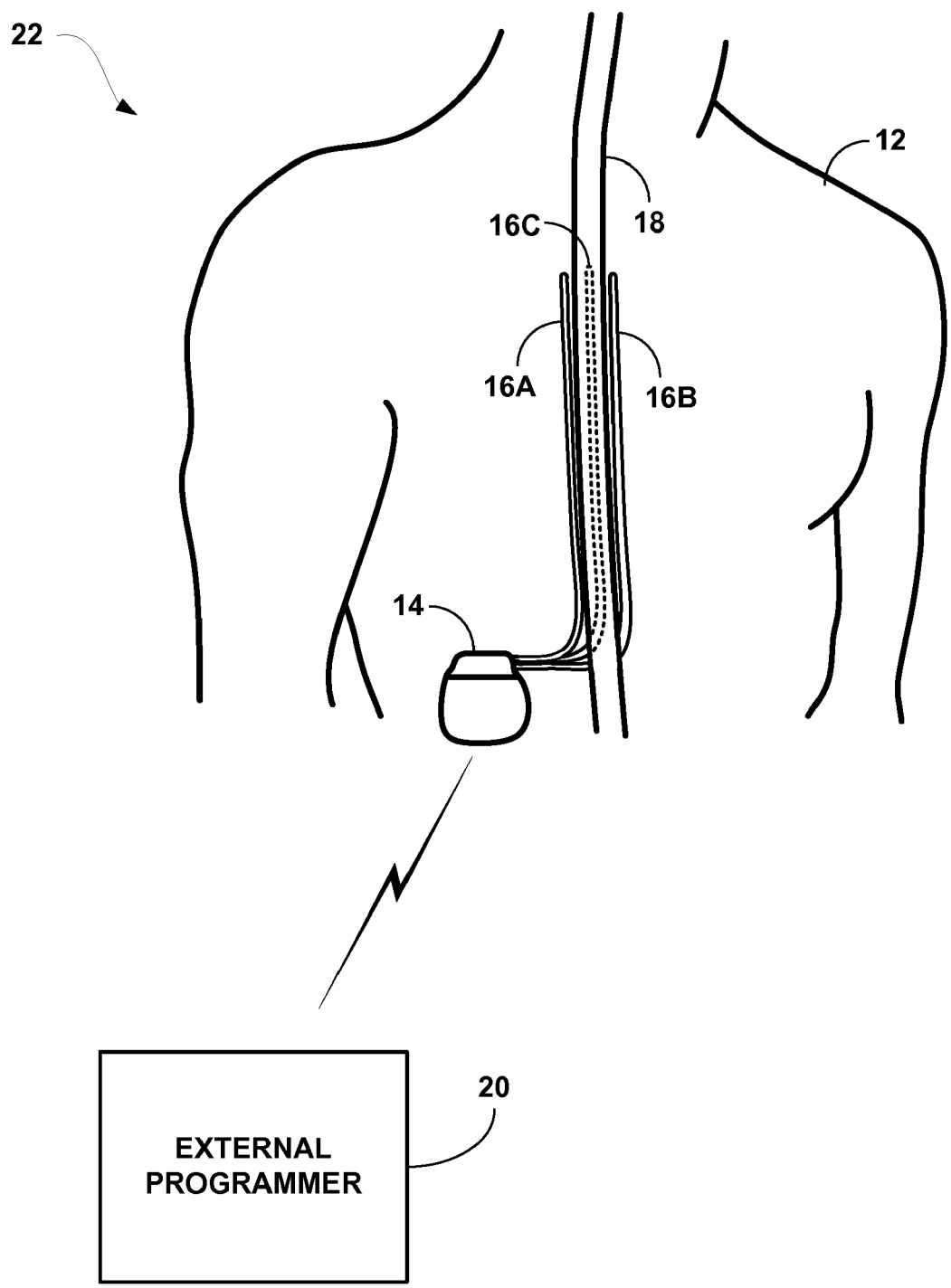
FIG. 1B is a conceptual diagram illustrating an implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead along spinal cord 18. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. External programmer 20 may be initially told the number and configuration of leads 16 in order to appropriately program stimulation therapy.

For example, leads 16A and 16B could include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
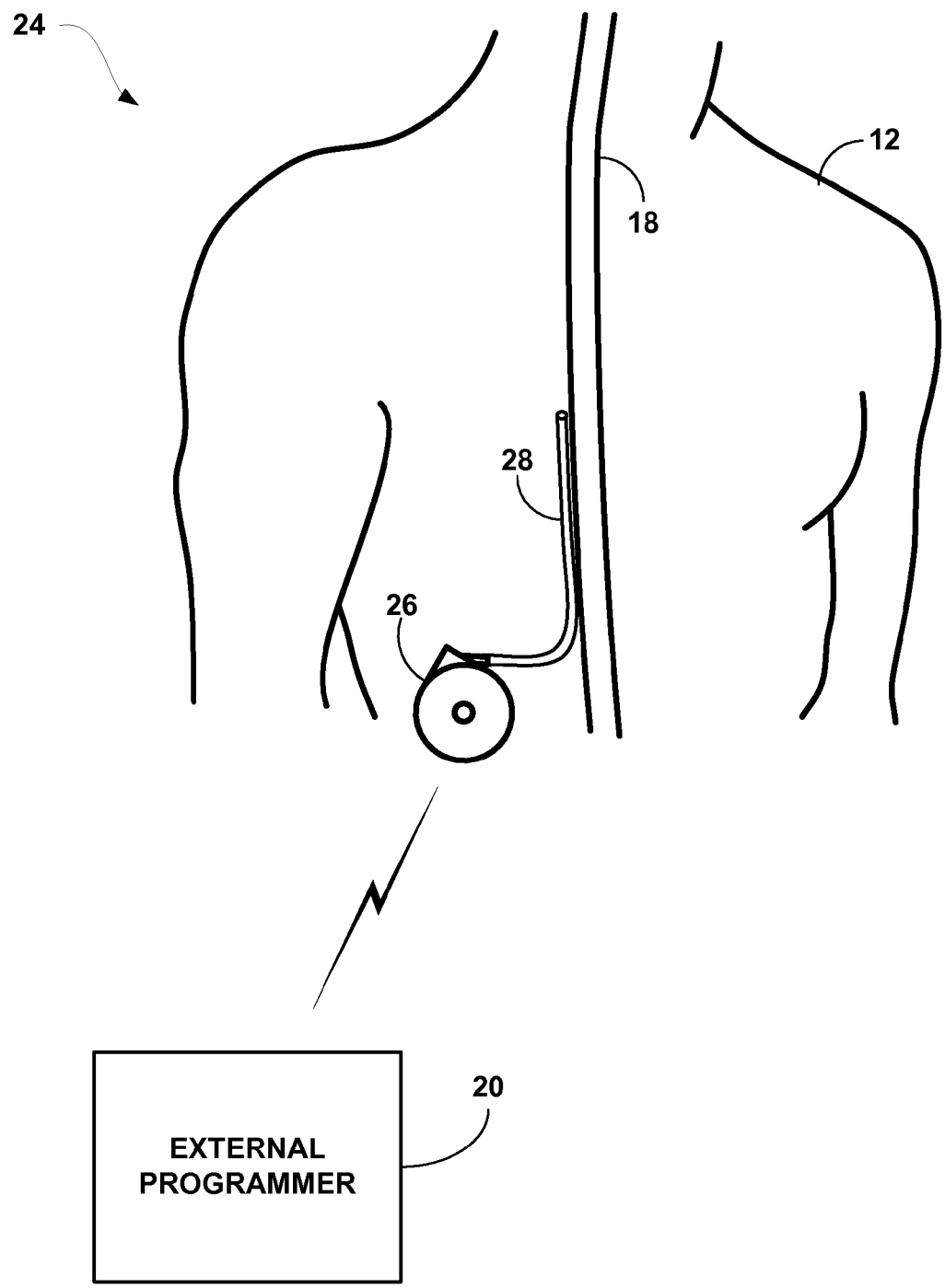
FIG. 1C is a conceptual diagram illustrating an implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of drug stimulation therapy instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some embodiments, IMD 26 may be an external device which includes a percutaneous catheter that forms catheter 28 or that is coupled to catheter 28, e.g., via a fluid coupler. In other embodiments, IMD 26 may include both electrical stimulation as described in IMD 14 and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Similar to IMD 14, IMD 26 may include a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Figure 2:
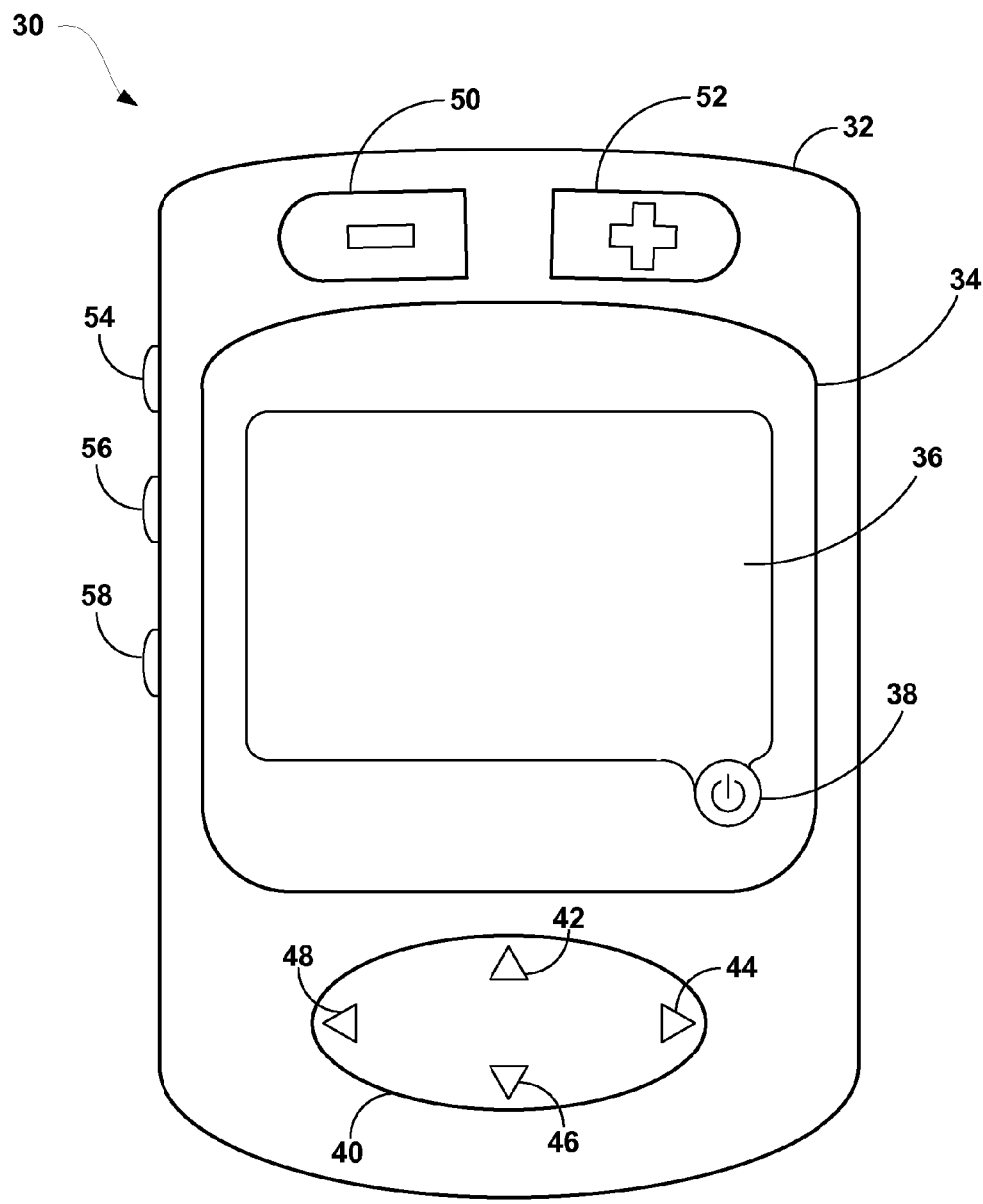
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an implantable medical device. Patient programmer 30 is an example embodiment of external programmer 20 illustrated in FIGS. 1A, 1B and 1C and may be used with either IMD 14 or IMD 26. In alternative embodiments, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, which may form part of an output device of a user interface, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which forms part of an input device of a user interface and allows a user to navigate through items displayed on display 36 in the direction of arrows 42, 44, 46, and 48. In some embodiments, the buttons and pad 40 may take the form of soft keys (e.g., with functions and contexts indicated on display 36), with functionality that may change, for example, based on current programming operation or user preference. In alternative embodiments, display 36 may be a touch screen in which patient 12 may interact directly with display 36 without the use of control pad 40 or even increase button 52 and decrease button 50.

In the illustrated embodiment, patient programmer 30 is a hand held device. Patient programmer 30 may accompany patient 12 throughout a daily routine. In some cases, patient programmer 30 may be used by a clinician when patient 12 visits the clinician in a hospital or clinic. In other embodiments, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52. In some embodiments, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may be a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36.

Display 36 may present a visible posture state indication. In addition, display 36 may present therapy adjustment information stored during the record mode of IMD 14 and even present nominal or suggested therapy parameters for a plurality of programs. Patient 12 may then selectively set the plurality of programs to the respective nominal or suggested therapy parameters via a single confirmation input. As described herein, patient programmer 30 may be configured to perform any tasks described with respect to clinician programmer 60 (described below in reference to FIG. 3) or another external programmer 20.

Control pad 40 allows patient 12 to navigate through items displayed on display 36. Patient 12 may press control pad 40 on any of arrows 42, 44, 46, and 48 in order to move to another item on display 36 or move to another screen not currently shown on the display. In some embodiments, pressing the middle of control pad 40 may select any item highlighted in display 36. In other embodiments, scroll bars, a scroll wheel, individual buttons, or a joystick may perform the complete or partial functions of control pad 40. In alternative embodiments, control pad 40 may be a touch pad that allows patient 12 to move a cursor within the user interface displayed on display 36 to manage therapy or review posture state information.

Decrease button 50 and increase button 52 provide an input mechanism for patient 12. In general, decrease button 50 may decrease the value of a highlighted stimulation parameter every time the decrease button is pressed. In contrast, increase button 52 may increase the value of a highlighted stimulation parameter one step every time the increase button is pressed. While buttons 50 and 52 may be used to control the value of any stimulation parameter, buttons 50 and 52 may also control patient feedback input. When either of buttons 50 and 52 is selected, patient programmer 30 may initialize communication with IMD 14 or 26 to change therapy accordingly.

When depressed by patient 12, stimulation ON button 54 directs programmer 30 to generate a command for communication to IMD 14 that turns on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some embodiments, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display 36 brightness and contrast, or other similar options. In alternative embodiments, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative embodiments of patient programmer 30 may include other input mechanisms such as a keypad, microphone, camera lens, or any other media input that allows the user to interact with the user interface provided by patient programmer 30.

In alternative embodiments, the buttons of patient programmer 30 may perform different functions than the functions provided in FIG. 2 as an example. In addition, other embodiments of patient programmer 30 may include different button layouts or different numbers of buttons. For example, patient programmer 30 may even include a single touch screen that incorporates all user interface functionality with a limited set of buttons or no other buttons.

Figure 3:
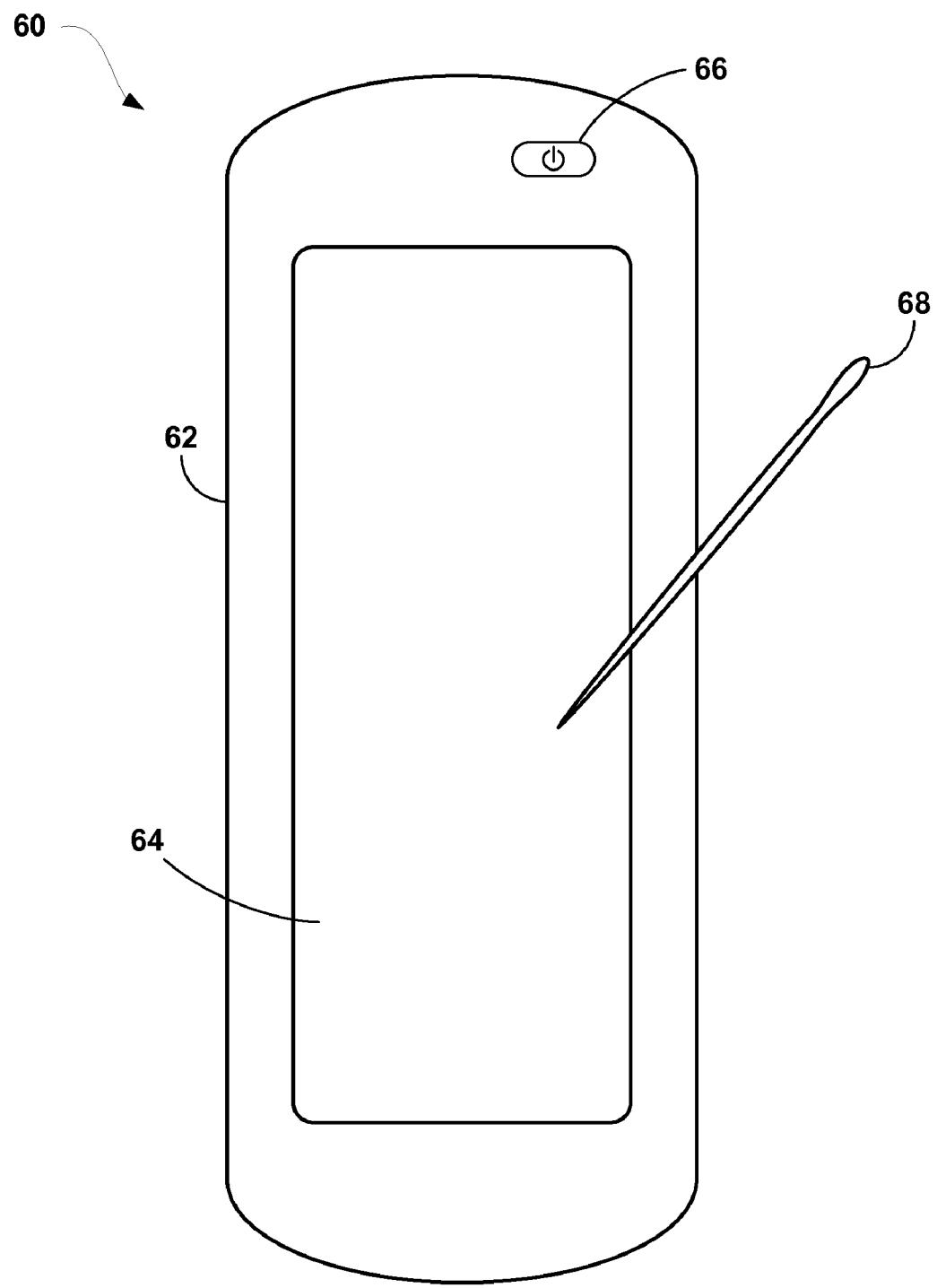
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an implantable medical device. Clinician programmer 60 is an example embodiment of external programmer 20 illustrated in FIGS. 1A, 1B and 1C and may be used with either IMD 14 or IMD 26. In alternative embodiments, clinician programmer 60 may be used with an external medical device. As shown in FIG. 3, clinician programmer 60 provides a user interface (not shown) for a user, such as a clinician, physician, technician, or nurse, to manage and program stimulation therapy. In addition, clinician programmer 60 may be used to review objective posture state information to monitor the progress and therapy efficacy of patient 12. Clinician programmer 60 is protected by housing 62, which encloses circuitry necessary for clinician programmer 60 to operate.

Clinician programmer 60 is used by the clinician or other user to modify and review therapy to patient 12. The clinician may define each therapy parameter value for each of the programs that define stimulation therapy. The therapy parameters, such as amplitude, may be defined specifically for each of the posture states that patient 12 will be engaged in during therapy. In addition, the clinician may use clinician programmer 60 to define each posture state of patient 12 by using the posture cones described herein or some other technique for associating posture state sensor output to the posture state of patient 12.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some embodiments, the user may be able to touch display 64 with a finger, pen, or any other pointing device. In alternative embodiments, clinician programmer 60 may include one or more buttons, keypads, control pads, touch pads, or other devices that accept user input, similar to patient programmer 30.

In the illustrated embodiment, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some embodiments, clinician programmer 60 may be a larger device that may be less portable, such as a notebook computer, workstation, or event a remote computer that communicates with IMD 14 or 26 via a remote telemetry device.

Most, if not all, of clinician programmer 60 functions may be completed via the touch screen of display 64. The user may program stimulation therapy, modify programs or groups, retrieve stored therapy data, retrieve posture state information, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Clinician programmer 60 may also allow the clinician to view historical therapy adjustment information stored in IMD 14 during therapy. As mentioned previously, the therapy adjustment information includes any associations created between therapy parameter value adjustments and posture states for each program that delivers automatic posture responsive stimulation. The clinician may initially orient IMD 14 to patient 12 and enable the record mode for IMD 14 to store any associations as therapy adjustment information. Clinician programmer 60 may then acquire the therapy adjustment information from IMD 14 and present the information to the clinician in order to allow continued effective therapy modifications.

In some examples, clinician programmer 60 may also allow the clinician to adjust the search period of the posture search timer and the stability period of the posture stability timer. The posture search timer and the posture stability timer enable IMD 14 to determine the posture state with which a therapy adjustment should be associated. Depending upon the condition of patient 12 or the clinician preferences, the clinician may desire to adjust the search period and stability period to most accurately reflect the intentions of patient 12. For example, if patient 12 has a habit of adjusting therapy long before making a change to the posture state or patient 12 takes a long time to assume a desired posture state, the clinician may desire to increase the search period and stability period in order to properly associate the therapy adjustment with the intended posture state. In some examples, clinician programmer 60 may suggest appropriate search periods and stability periods for patients diagnosed with particular conditions that may hinder their movement or involve multiple oscillations in posture state before settling on the final posture state.

In addition, clinician programmer 60 may present nominal and suggested therapy parameters to the clinician based upon the stored therapy adjustment information in IMD 14. In one example, clinician programmer 60 may simply present an amplitude range determined by the therapy adjustments for each program and posture state. The clinician may then set the amplitude of each program to a nominal therapy parameter presented on display 64 of clinician programmer 60. For example, the nominal therapy parameter may be the minimum amplitude used by patient 12 for each program. Alternatively, clinician programmer 60 may present the last therapy adjustment for each program and posture state, or an average therapy adjustment. Clinician programmer 60 may then set the therapy parameter for all displayed programs with a single confirmation input from the clinician. This single input may decrease clinician programming time and overall programming complexity.

Further, clinician programmer 60 may present a suggested therapy parameter to the clinician for each program and posture state that is based upon the therapy adjustment information. The suggested therapy parameter may or may not be a parameter that was used from a therapy adjustment. Clinician programmer 60 may utilize a guided algorithm that attempts to generate a suggested therapy parameter that the clinician desires to free the clinician from manually determining the best therapy parameter for each program. Clinician programmer 60 may utilize one algorithm or receive a guided algorithm input from the clinician that customizes how clinician programmer 60 generates the suggested therapy parameters. For example, clinician programmer 60 may use a target trend guided algorithm that weights more recent therapy adjustments so that the suggested therapy parameters are more representative of recent patient 12 response to stimulation therapy.

In some cases, all processing may be performed in IMD 14 and distributed to clinician programmer 60 only for presentation to the clinician. Alternatively, IMD 14, clinician programmer 60, patient programmer 30, or another computing device may share in the processing duties of therapy adjustment information and any other data prior to presenting the information on clinician programmer 60. In other embodiments, IMD 14 may simply transfer raw data to an external programmer 20 or other computing device for data processing necessary to perform the tasks described herein. Accordingly, methods described in this disclosure may be implemented within IMD 14, programmer 30, programmer 60, or within a combination of such components.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
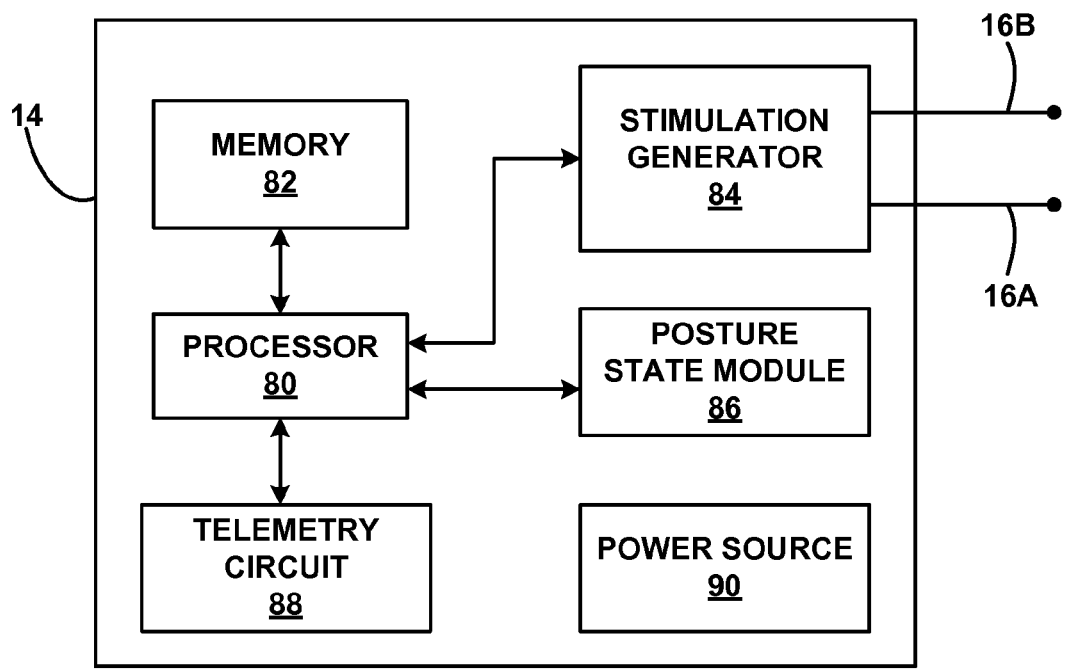
FIG. 4 is a functional block diagram illustrating various components of an implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. The stimulation generator 84 forms a therapy delivery module. Memory 82 may store instructions for execution by processor 80, stimulation therapy data, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, therapy adjustment information, program histories, and any other data that may benefit from separate physical memory modules.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other embodiments, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other embodiments, rather than rewriting a single memory location, processor 80 may make use of two or more memory locations.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and 1200 Hz, more preferably between approximately 5 Hz and 250 Hz, and still more preferably between approximately 30 Hz and 130 Hz.
2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage that is delivered. For example, the range of current amplitude may be between approximately 0.1 milliamps (mA) and 50 mA.
3. Pulse Width: between about 10 microseconds and 5000 microseconds, more preferably between approximately 100 microseconds and 1000 microseconds, and still more preferably between approximately 180 microseconds and 450 microseconds.

In other applications, different ranges of parameter values may be used. For deep brain stimulation (DBS), as one example, alleviation or reduction of symptoms associated with Parkinson's disease, essential tremor, epilepsy or other disorders may make use of stimulation having a pulse rate in the range of approximately 0.5 to 1200 Hz, more preferably 5 to 250 Hz, and still more preferably 30 to 185 Hz, and a pulse width in the range of approximately 10 microseconds and 5000 microseconds, more preferably between approximately 60 microseconds and 1000 microseconds, still more preferably between approximately 60 microseconds and 450 microseconds, and even more preferably between approximately 60 microseconds and 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 may include one or more posture state sensors, e.g., one or more accelerometers such as three-axis accelerometers, capable of detecting static orientation or vectors in three-dimensions. Example accelerometers may include micro-electro-mechanical accelerometers. In other examples, posture state module 86 may alternatively or additionally include one or more gyroscopes, pressure transducers or other sensors to sense the posture state of patient 12. Posture state information generated by posture state module 86 and processor 80 may correspond to an activity, posture, or posture and activity undertaken by patient 12 or a gross level of physical activity, e.g., activity counts based on footfalls or the like.

Posture state information from posture state module 86 may be stored in memory 82 to be later reviewed by a clinician, used to adjust therapy, presented as a posture state indication to patient 12, or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture defined within memory 82. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture state-responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

As described herein, the posture state data, or raw data of the posture state information, is stored by system 10 to be used at a later time. The posture state information may also be used in addition to the therapy adjustment information when the user desires to view more detailed information related to the posture states engaged by patient 12. Memory 82 may store all of the posture state data detected during therapy or use of IMD 14, or memory 82 may periodically offload the posture state data to clinician programmer 60 or a different external programmer 20 or device. In other examples, memory 82 may reserve a portion of the memory to store recent posture state data easily accessible to processor 80 for analysis. In addition, older posture state data may be compressed within memory 82 to require less memory storage until later needed by external programmer 20 or processor 80.

A posture state parameter value from posture state module 86 that indicates the posture state of patient 12 may constantly vary throughout the daily activities of patient 12. However, a certain activity (e.g., walking, running, or biking) or a posture (e.g., standing, sitting, or lying down) may include multiple posture state parameter values from posture state module 86. In this manner, a posture state may include a broad range of posture state parameter values. Memory 82 may include definitions for each posture state of patient 12. In one example, the definitions of each posture state may be illustrated as a cone in three-dimensional space. Whenever the posture state parameter value, e.g., a sensed coordinate vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture state-responsive stimulation may allow IMD 14 to implement a certain level of automation in therapy adjustments. Automatically adjusting stimulation may free patient 12 from the constant task of manually adjusting therapy parameters each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. Alternatively, patient 12 may be unable to manually adjust the therapy if patient programmer 30 is unavailable or patient 12 is preoccupied. In some embodiments, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other embodiments, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some embodiments, to confirm or reject changes in sensed posture state that may result from vibration, patient travel (e.g., in an aircraft, car or train), or some other false positive of posture state.

In some embodiments, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some embodiments, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion, or activity. This activity may involve a level, direction of motion, or acceleration of the patient.

One method for determining the activity is an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count." The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

Processor 80 may monitor the posture state of patient 12 and associate any therapy adjustments that patient 12 makes to the posture state currently occupied by patient 12. However, processor 80 may also employ techniques that allow a therapy adjustment to be associated with a later posture state in cases when patient 12 makes a therapy adjustment in anticipation of changing the posture state. Patient 12 may desire to make this preemptory adjustment to avoid being over-stimulated or under-stimulated when the patient assumes the new posture state.

Processor 80 may employ multiple timers that monitor therapy adjustments and when a new posture state occurs, as a result of a posture state transition. Processor 80 may use a posture search timer having a search period, where the search timer begins upon the detection of the therapy adjustment and expires when the search period lapses. The posture search timer allows a certain amount of time, or the search period, for patient 12 to finally engage in the intended posture state. In addition, processor 80 uses a posture stability timer, where the posture stability timer begins upon the sensing of a different posture state and requires a certain amount of time, the stability period, to elapse while patient 12 is in the same posture state before the posture state can be considered the final posture state. A therapy adjustment is only associated with a posture state when the final posture state is started, i.e., the stability timer is started, prior to the expiration of the search period and the final posture state lasts at least as long as the stability period. Any other therapy adjustments are either associated with the initial posture state patient 12 was engaged in when the therapy was adjusted or not associated with any posture state, depending upon the instructions stored in memory 82.

Although external programmer 20 may perform any processing on the therapy adjustment information, such as the association of therapy adjustments to posture states, processor 80 of IMD 14 may be configured to analyze the information and generate desired information. For example, processor 80 may generate nominal therapy parameters or suggested therapy parameters based upon the therapy adjustment information stored in memory 82. In this manner, IMD 14 may transmit the nominal or suggested therapy parameters directly to external programmer 20 for presentation to the user. Any other shared processing between IMD 14 and external programmer 20 is also contemplated.

Wireless telemetry in IMD 14 with external programmer 20, e.g., patient programmer 30 or clinician programmer 60, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Figure 5:
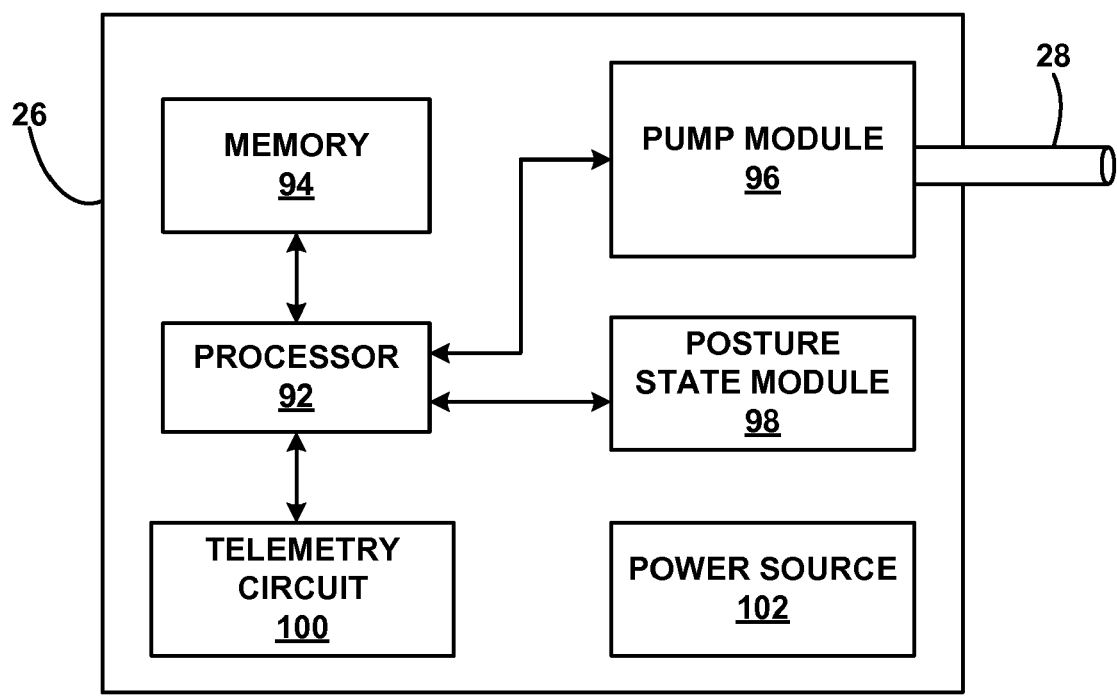
FIG. 5 is a functional block diagram illustrating various components of an implantable drug pump.

FIG. 5 is a functional block diagram illustrating various components of an IMD 26 that is a drug pump. IMD 26 is a drug pump that operates substantially similar to IMD 14 of FIG. 4. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 may control pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state module 98 to adjust drug delivery therapy when patient 12 changes posture states, e.g., adjusts his or her posture. In alternative embodiments, system 10 may be employed by an implantable medical device that delivers therapy via both electrical stimulation therapy and drug delivery therapy as a combination of IMD 14 and IMD 26.

Figure 6:
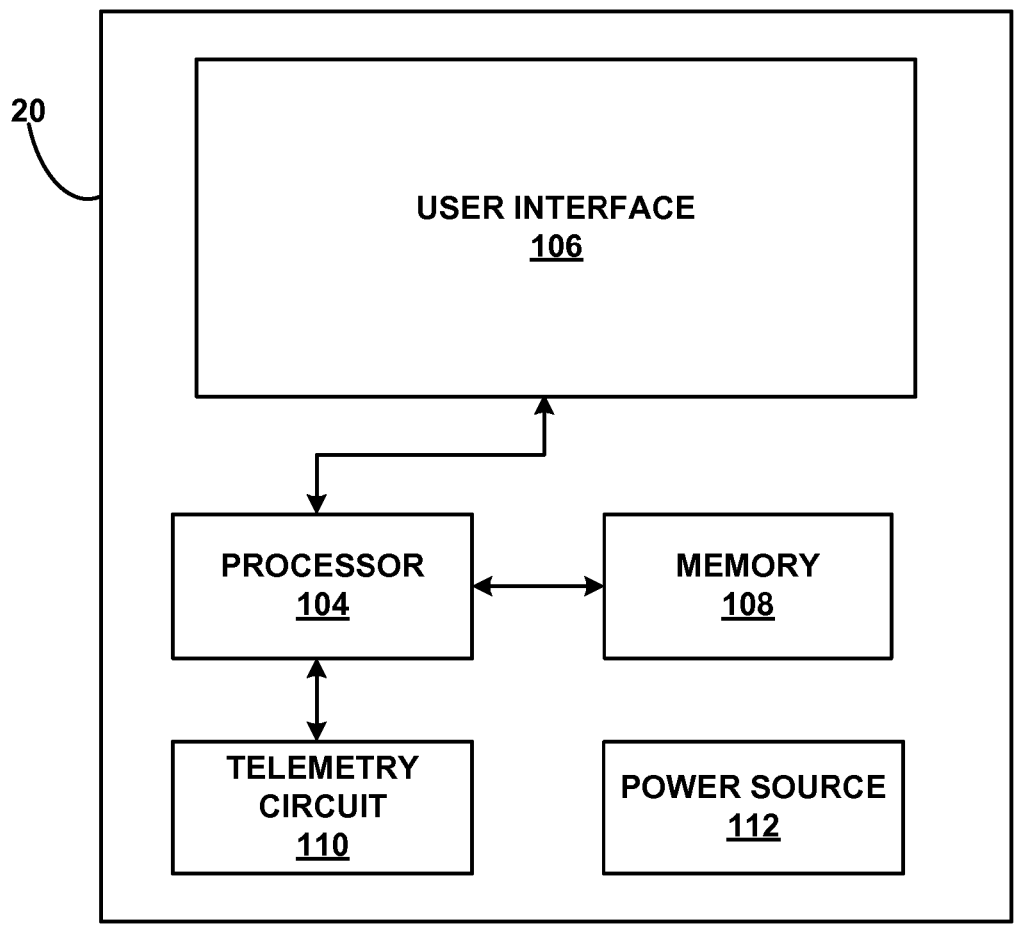
FIG. 6 is a functional block diagram illustrating various components of an external programmer for an implantable medical device.

FIG. 6 is a functional block diagram illustrating various components of an external programmer 20 for IMDs 14 or 26. As shown in FIG. 6, external programmer 20 includes processor 104, memory 108, telemetry circuit 110, user interface 106, and power source 112. External programmer 20 may be embodied as patient programmer 30 or clinician programmer 60. A clinician or patient 12 interacts with user interface 106 in order to manually change the stimulation parameters of a program, change programs within a group, turn posture responsive stimulation ON or OFF, view therapy information, view posture state information, or otherwise communicate with IMDs 14 or 26.

User interface 106 may include a screen and one or more input buttons, as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 106 may include a touch pad, increase and decrease buttons, emergency shut off button, and other buttons needed to control the stimulation therapy, as described above with regard to patient programmer 30. Processor 104 controls user interface 106, retrieves data from memory 108 and stores data within memory 108. Processor 104 also controls the transmission of data through telemetry circuit 110 to IMDs 14 or 26. Memory 108 includes operation instructions for processor 104 and data related to patient 12 therapy.

User interface 106 is configured to present therapy adjustment information to the user for monitoring adjustments made by patient 12 and allowing single input and guided programming options for the user. After IMD 14 has associated therapy adjustments to posture states, user interface 106 of external programmer 20 may present the associations to the user as a range of therapy adjustments, maximum and minimum values of the adjusted parameters, last adjustments made, number of adjustments made for each program and posture state, or any other details of the associations. The number of patient therapy adjustments may be recorded based on the cumulative number of adjustments made by the patient 12 over the course of a therapy session when the patient may occupy each of the posture states multiple times. In particular, the number of adjustments may be a cumulative number of adjustments over multiple instances of the sensed posture state, i.e., multiple times in which the patient occupied the posture state. In addition, user interface 106 may display the therapy adjustment information as graphical bar graphs or charts, numerical spread sheets, or any other manner in which information may be displayed. Further, user interface 106 may present nominal or suggested therapy parameters that the user may accept for all programs by making one confirmation input to user interface 106.

The therapy adjustment information may also be stored within memory 108 periodically during therapy, whenever external programmer 20 communicates within IMD 14, or only when the user desired to use the therapy adjustment information. Memory 108 may include a separate memory for therapy adjustment information as opposed to other posture state information or operational instructions. In addition, if memory 108 does store posture state information from patient 12, memory 108 may use one or more hardware or software security measures to protect the identify of patient 12. For example, memory 108 may have separate physical memories for each patient or the user may be required to enter a password to access each patient's posture state data.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. The techniques described herein may be communicated between IMD 14 via any type of external device capable of communication with IMD 14.

Figure 7:
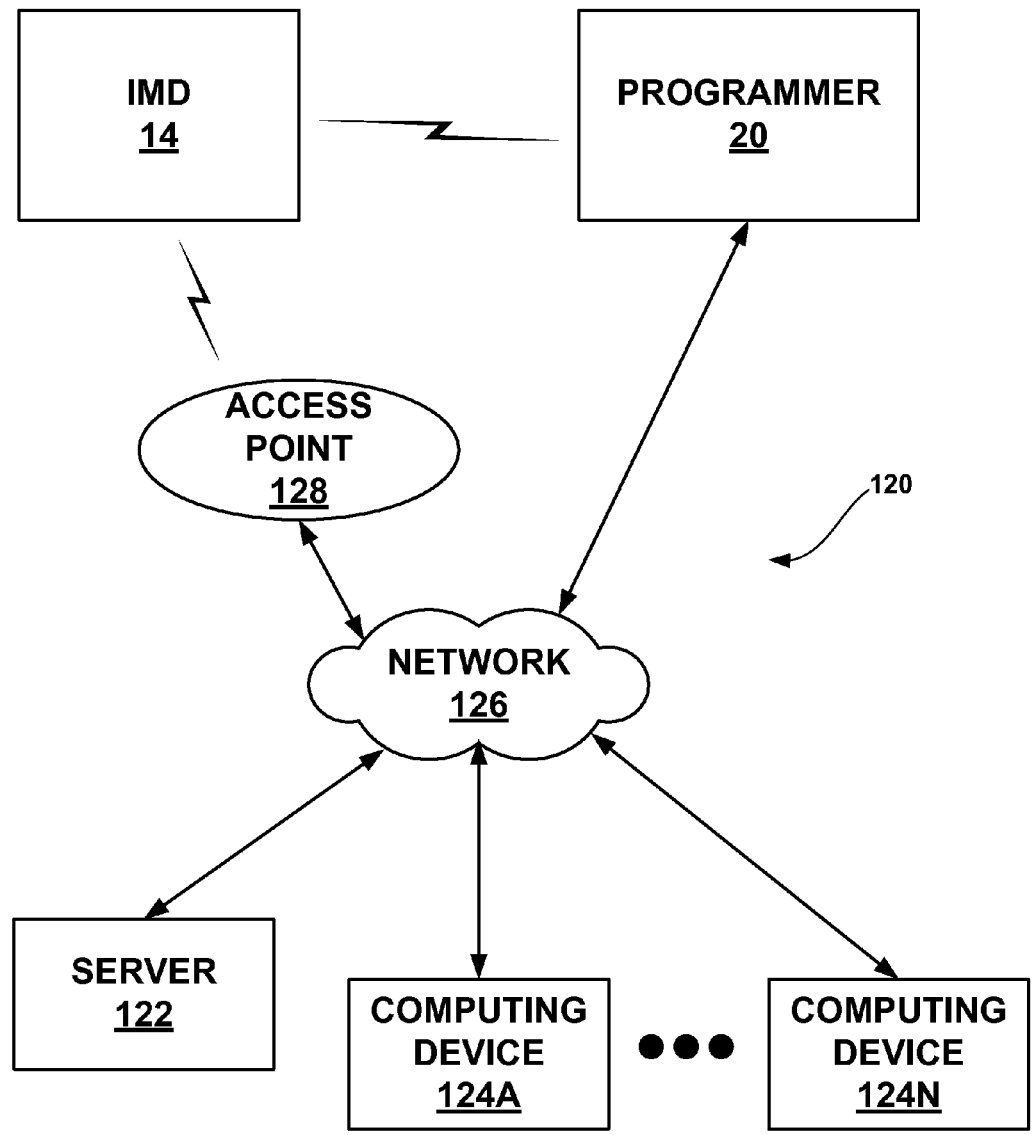
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, digital signal processors (DSPs), application specific integrated circuits (ASICs), field programmable gate arrays (FPGAs), programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other embodiments, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the posture state of patient 12, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed. Further, server 122 may process therapy adjustment information and generate suggested therapy parameters for each program and posture state based upon the therapy adjustment information. If a guided algorithm is computationally intensive, server 122 may be best suited for generating the necessary parameters for therapy.

Using system 120 of FIG. 7, a clinician, physician, technician, or even patient 12, may review therapy adjustment information from the record mode of IMD 14. The user may remotely monitor the progress and trends of patient 12, limiting the number of times that patient 12 may need to physically visit the clinician. This monitoring may also reduce the time needed to find efficacious therapy parameters by allowing the clinician to more frequently monitor how patient 12 is using patient programmer 30 and how often changes to therapy must be made. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients. Further, posture state detection may also be used to provide notifications, such as providing notification via a wireless link to a care giver that a patient has potentially experienced a fall.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
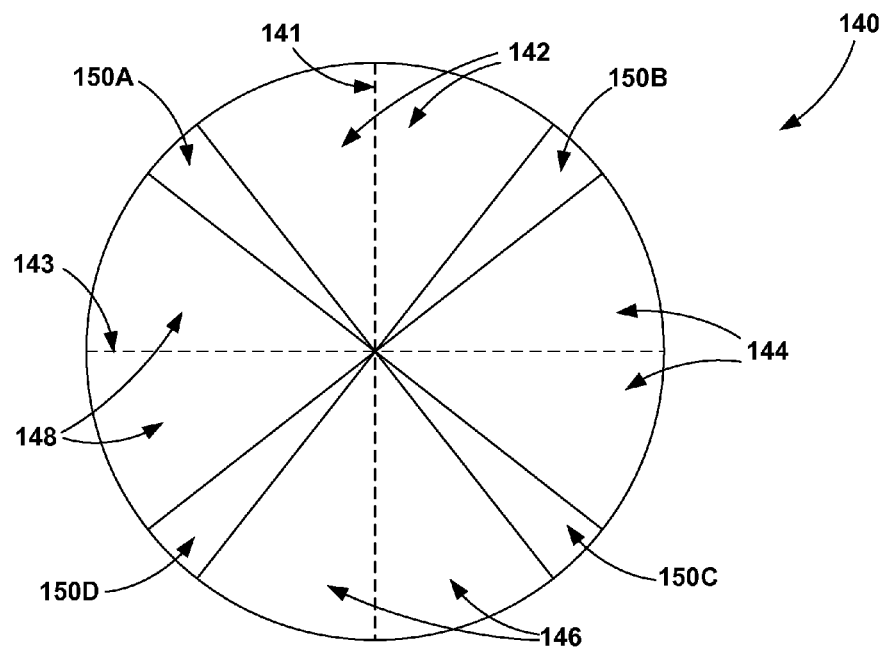
FIGS. 8A-8C are conceptual illustrations of posture cones that may be used to define a posture state of a patient based on signals sensed by a posture state sensor.
Figure 8B:
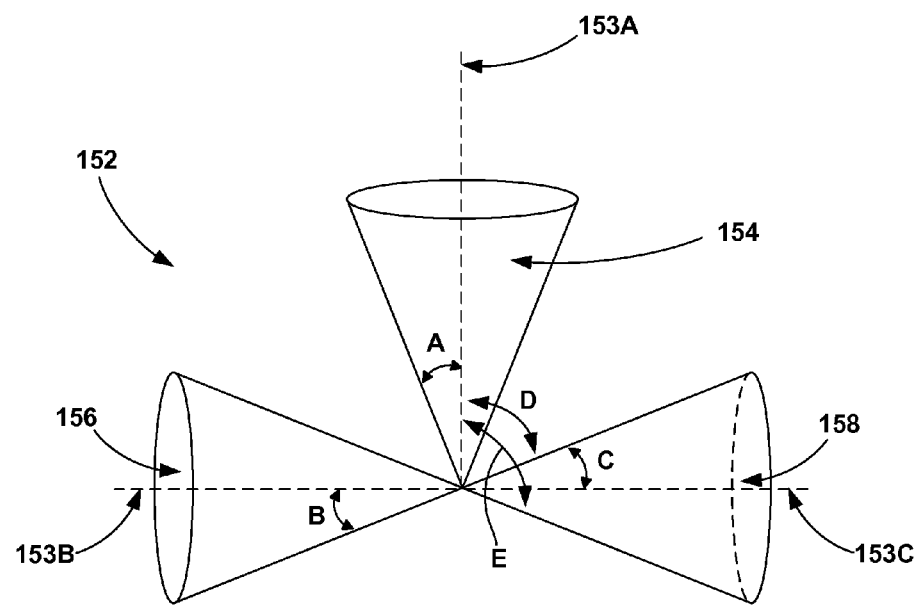
Figure 8C:
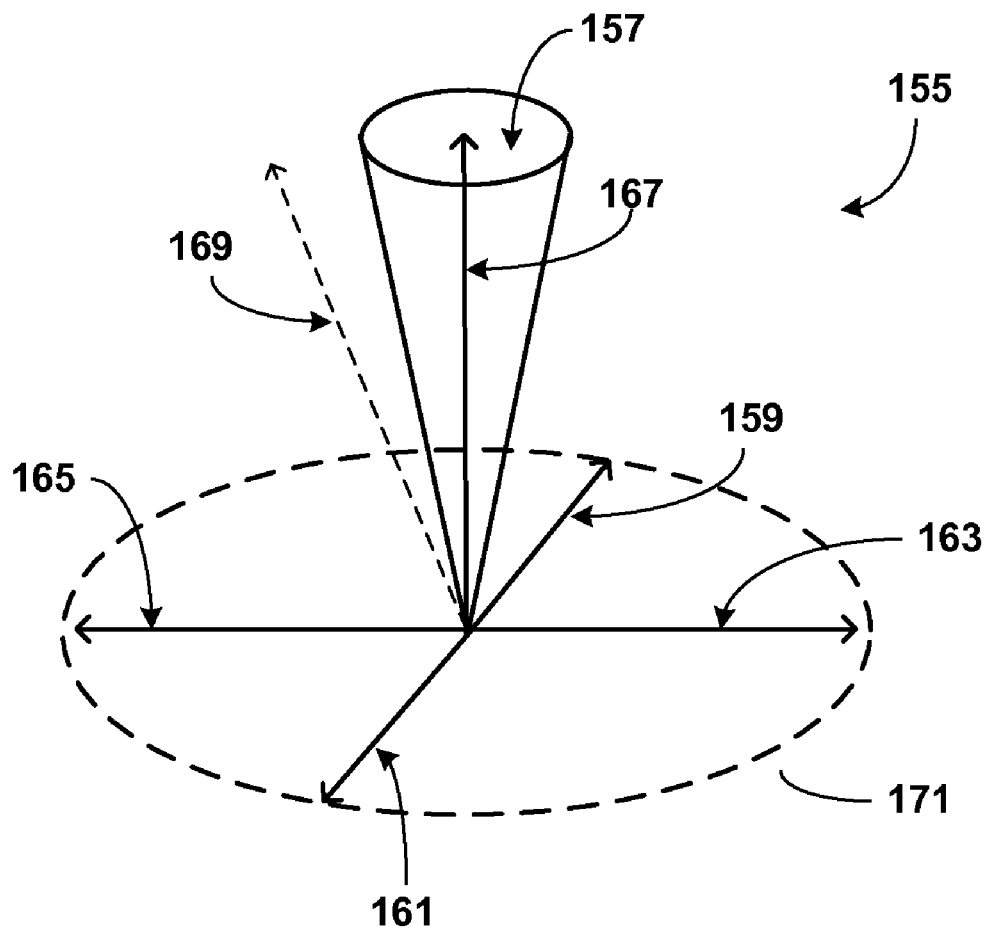

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors.

While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone may be positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Moreover, the reference coordinate vectors need not reside in the same plane. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other, and need not even reside within the same plane. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another, and need not reside within a same plane.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E' may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
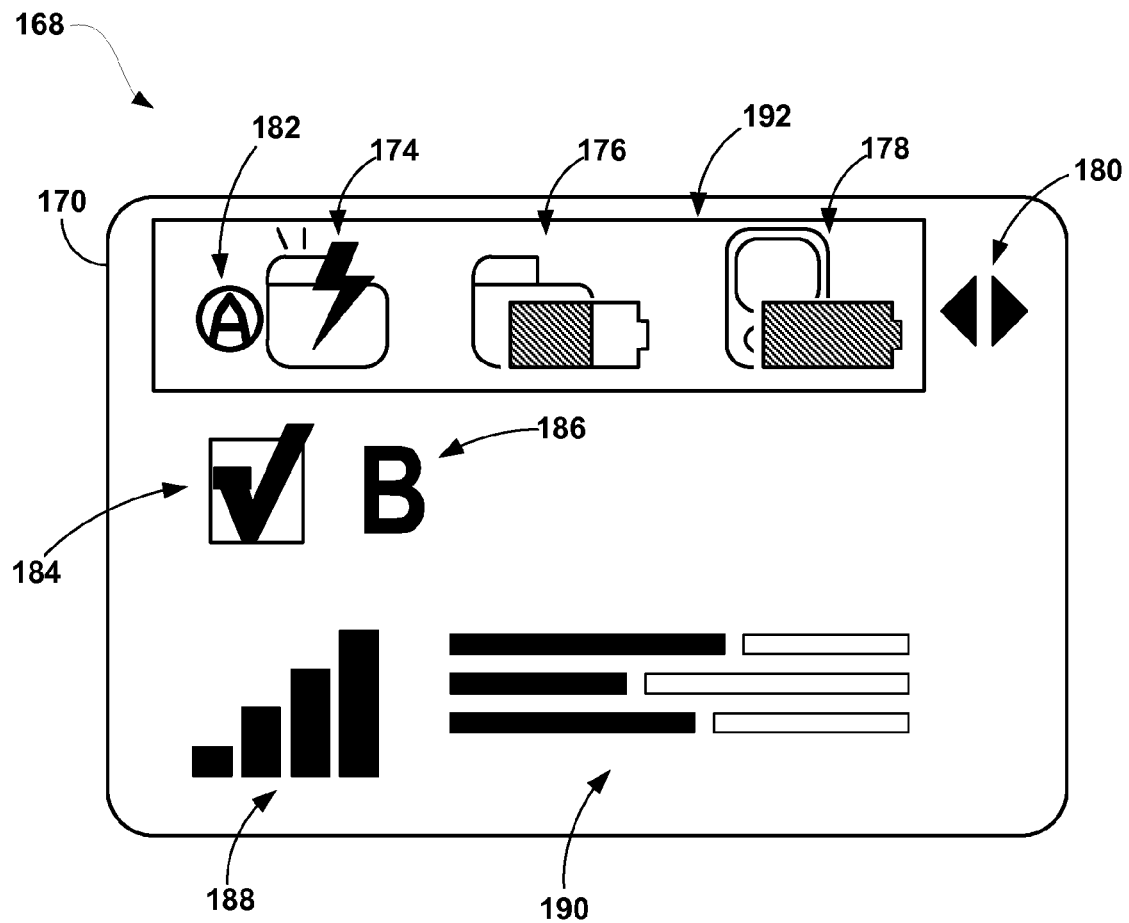
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be shown on clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some embodiments, numerical values of each program's amplitude may be shown in addition to or in place of amplitude graph 190. In other embodiments of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that IMD 14 is generally activated to automatically change therapy to patient 12 based upon the posture state detected by posture state module 86. In particularly, automatic posture responsive therapy may involve adjusting one or more therapy parameter values, selecting different programs or selecting different program groups based on the detected posture state of the patient. However, automatic posture response icon 182 is not present next to group identifier 186. Therefore, group "B" does not have automatic posture responsive therapy activated for any of the programs within group "B."

Some groups or individual programs in groups may support automatic posture responsive therapy. For example, automatic adjustment of one or more therapy parameters in response to posture state indication may be selectively activated or deactivated based on settings entered by a clinician, or possibly patient 12. Hence, some programs or groups may be configured for use with posture responsive therapy while other programs or groups may not be configured for use with posture responsive therapy. In some cases, if posture responsive therapy supported by the automatic posture response feature is desired, patient 12 may need to switch therapy to a different group that has automatic posture responsive therapy activated for IMD 14 to adjust therapy according to the patient 12 posture state.

Figure 10:
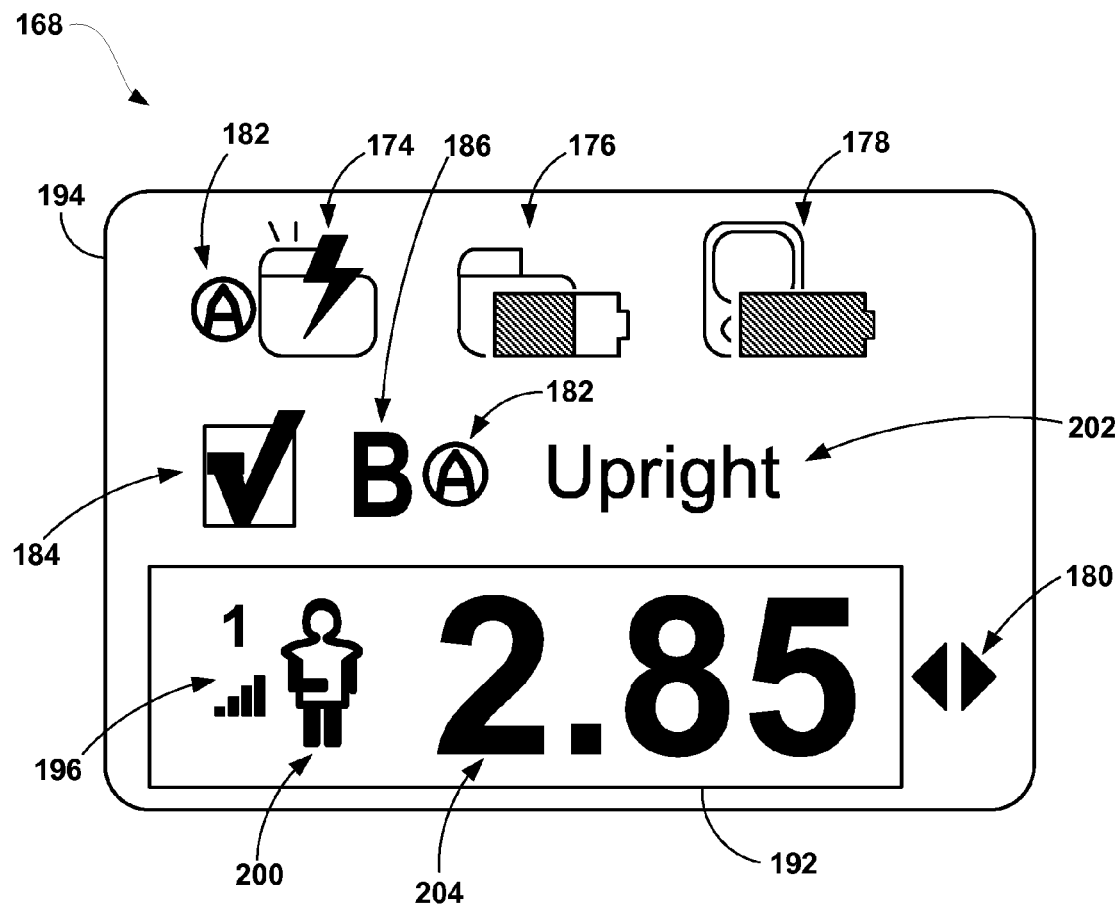
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or patient 12.

Group identifier 186 indicates that group "B" is active, and automatic posture response icon 182 indicates group "B" (containing one or more programs) is activated to allow IMD 14 to automatically adjust therapy according to the posture state of patient 12. Specifically, the posture state of patient 12 is the posture state in the example of FIG. 10. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 has detected that patient 12 is in the upright or standing posture. Supplementary posture state indication 202 supplements posture state indication 200 by illustrating in words to patient 12 the exact posture being detected by posture state module 86 of IMD 14. Posture state indication 200 and supplementary posture state indication 202 change according to the sensed, or detected, posture state detected by IMD 14. The posture state may be communicated to external programmer 20 immediately when IMD 14 detects a posture change, or communicated periodically or non-periodically by IMD 14 unilaterally or upon receiving a request from programmer 20. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 208. Selection box 192 may be moved to select other screen levels with control pad 40 in order to navigate through other stimulation groups or adjustable elements of the therapy. When patient 12 selects a different program with control pad 40, program identifier 196 will change number to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, different numbers of vibratory pulses delivered in sequence or vibratory pulses of different lengths, amplitudes, or frequencies.

Figure 11A:
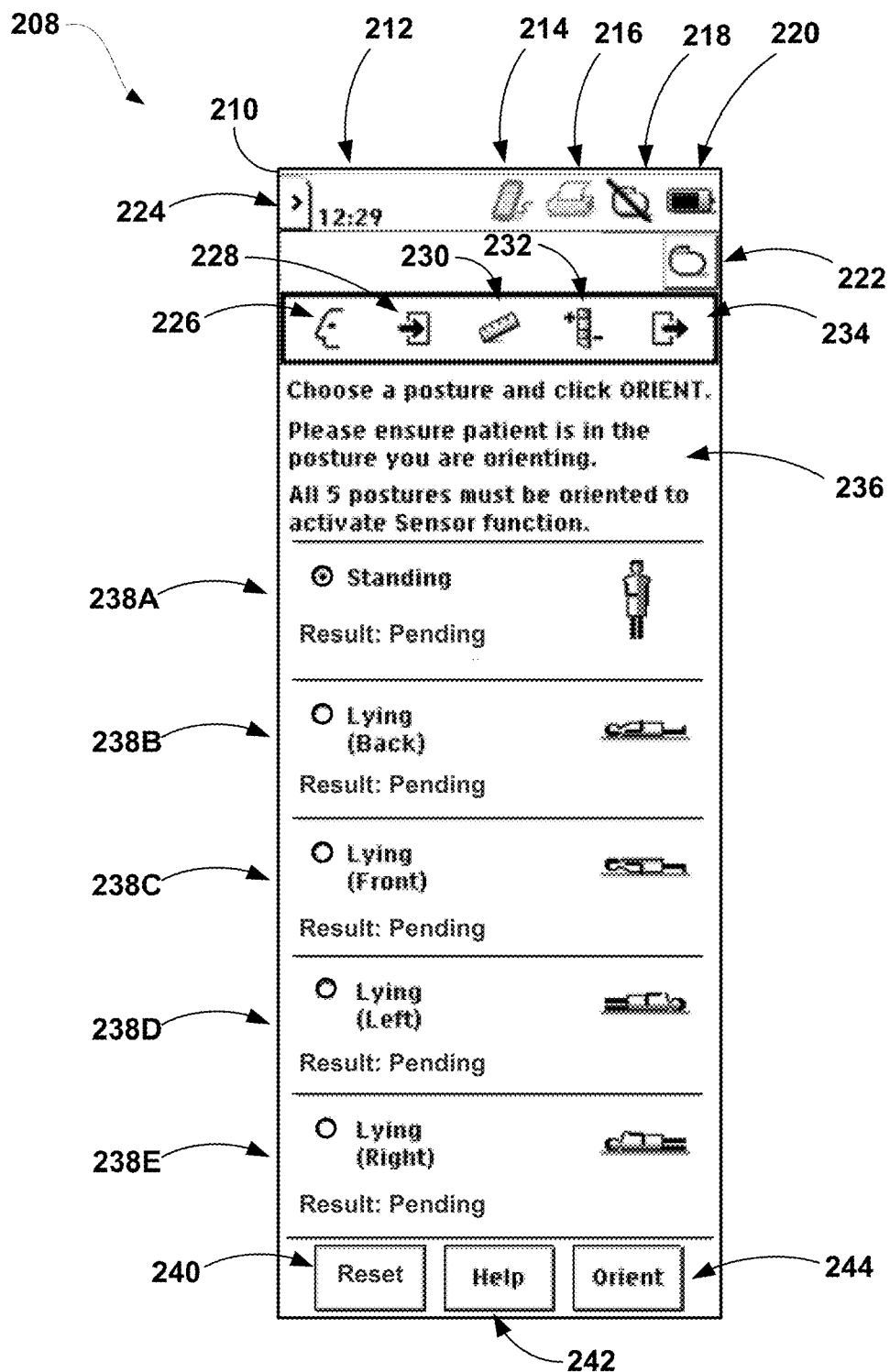
FIGS. 11A and 11B are conceptual diagrams illustrating an example user interface for orienting an implantable medical device with patient posture states prior to diagnostic or therapy use of the implantable medical device.

FIG. 11A is a conceptual diagram illustrating an example user interface 208 for orienting the implantable medical device prior to diagnostic or therapy use. User interface 208 is described as generally being displayed by clinician programmer 60. However, user interface 208 may also be displayed by patient programmer 30 or some other external programmer 20 or remote device. In any case, user interface 208 displays information related to sensing posture states, automatic posture response, reviewing recorded therapy adjustment information, and suggested therapy parameters to increase therapy efficacy.

In the example of FIG. 11A, screen 210 of user interface 208 presents orient information 236, operational menu 224, networking icon 214, printer icon 216, IMD communication icon 218, programmer battery icon 220, stimulation status icon 222, patient data icon 226, data recording icon 228, device status icon 230, programming icon 232, and data reporting icon 234. In addition, screen 210 includes posture state selections 238A, 238B, 238C, 238D, and 238E (collectively "posture state selections 238"), reset button 240, help button 242, and orient button 244. Screen 210 may be accessed by selecting programming icon 232 to open a drop down menu that allows the user to select one of multiple different screens. The user may select "orient device" or some other text or icon that symbolizes access to the process for initializing the orientation of the posture state sensor within IMD 14.

Screen 210 includes multiple menus and icons common to other screens of user interface 208. Operational menu 224 is a button that the user may select to view multiple options or preferences selectable by the user. Operational menu 224 may provide preferences for clinician programmer 60 instead of therapy specific information. Networking icon 214 is shown as grayed out to indicate that clinical programmer 60 is not currently connected to a network. When networking icon 214 is shown fully, clinician programmer 60 is connected to a network. Printer icon 216 indicates when clinician programmer 60 is connected to a printer. When printer icon 216 is grayed out as shown in FIG. 11A, there is no printer connected to clinician programmer 60.

Further, IMD communication icon 218 is shown as indicating that clinician programmer is not in communication with IMD 14 because the icon includes a slash through the IMD representation. The slash is removed when clinician programmer 60 has established a communication link to IMD 14. In addition, programmer battery icon 220 indicates the current charge level of the battery contained within clinician programmer 60. Stimulation status icon 222 indicates to the user when stimulation is being delivered to patient 12. Stimulation is not currently being delivered, but stimulation status icon 222 may include an electrical bolt through the IMD representation when stimulation is delivered.

Screen 210 also provides menu options related to stimulation therapy of patient 12. Patient data icon 226 allows the user to enter and review data related to the status of and the condition of patient 12. Data recording icon 228 allows the user to navigate to other screens to enter data recording preferences and review stored data. Device status icon 230 allows the user to view operational status of components of IMD 14, such as electrodes, leads, batteries, and any discovered problems. Programming icon 232 allows the user to navigate to programming screens that define the stimulation therapy parameters used to deliver stimulation to patient 12. In addition, data reporting icon 234 allows the user to view and print reports of patient 12 progress and other therapy information.

Specific to screen 210 of user interface 208, the clinician may initialize the orientation of the posture state sensor of IMD 14 by helping patient 12 assume each of posture state selections 238 and setting the output of the posture state sensor to that particular posture state selection. Orient information 236, while not necessary in all examples, is provided to instruct the clinician on how to orient IMD 14 to patient 12. For example, FIG. 11A shows that the clinician has selected posture state selection 238A. Once patient 12 has assumed the standing position, the clinician would select orient button 244 to have IMD 14 set the posture state sensor output to the standing posture state. The clinician would repeat this process for each of posture state selections 238, in any order that the clinician chooses. In other examples, the clinician may not need to orient IMD 14 to each of the five posture state selections 238. IMD 14 may only require three posture state selections, such as standing, one of lying back or lying front, and one of lying left and lying right.

The step of orienting IMD 14 may be necessary before IMD 14 is capable of accurately sensing or detecting any posture state engaged by patient 12. Therefore, user interface 208 may prevent the clinician from entering the record mode with IMD 14, for example, unless the clinician has oriented IMD 14 to patient 12. In this manner, any recorded associations between therapy adjustments and posture states or automatic posture response therapy is completed appropriately.

Figure 11B:
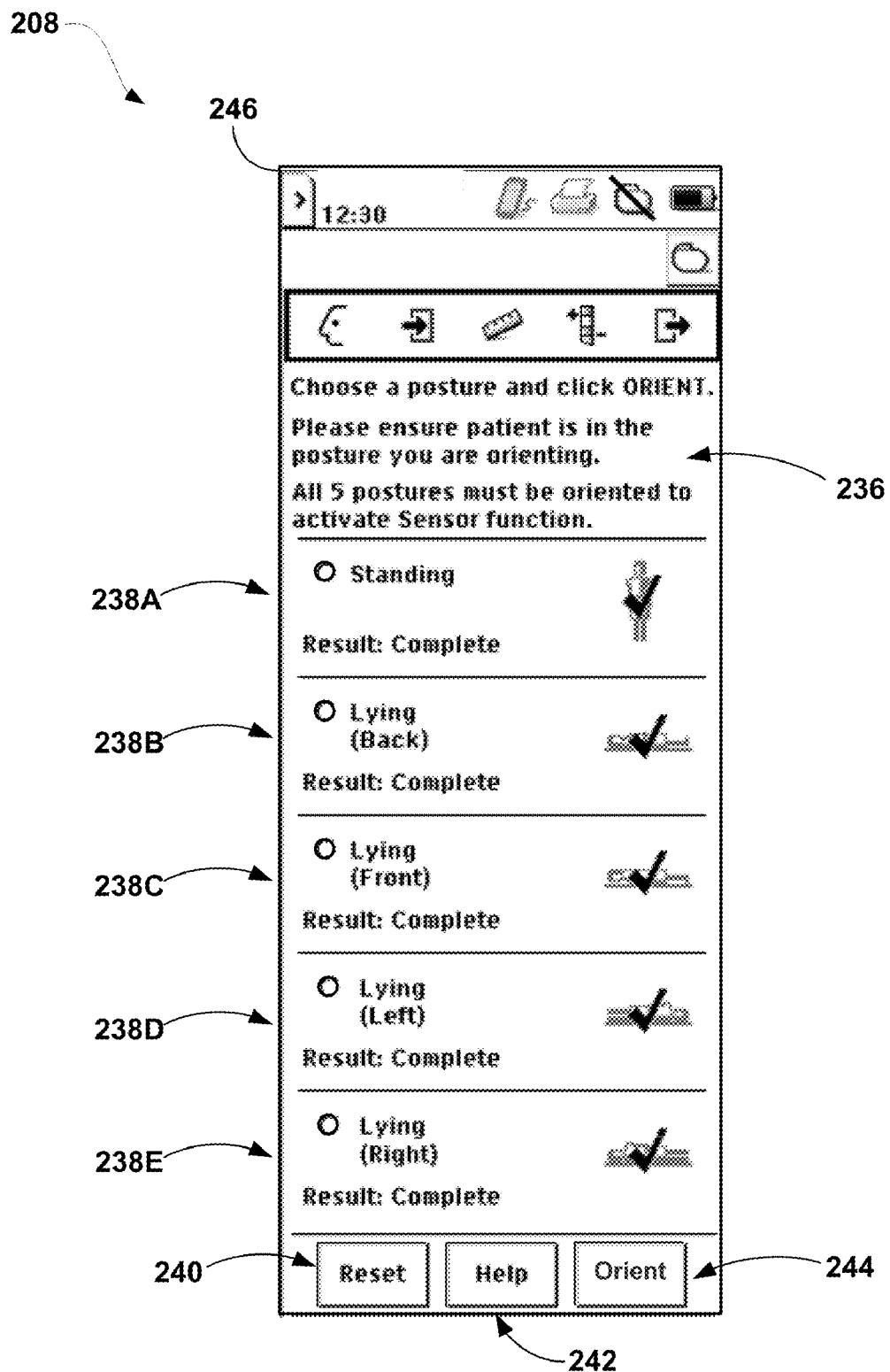

FIG. 11B is a conceptual diagram illustrating an example user interface 208 showing the user that orientation of the implantable medical device is complete. As shown in FIG. 11B, screen 246 of user interface 208 indicates to the clinician that orientation of IMD 14 has been completed for each of the posture state selections 238 as described in FIG. 11A. Each of the posture state selections 238 has a check mark through the graphical posture state indication on the right side of screen 246 to indicate that each posture state selection 238 has been oriented. Further, orient button 244 has been grayed out so that the clinician cannot select it. Once clinician programmer 60 is presented with screen 246, the clinician may move on to start the record mode, set programs for each posture state, or any other programming task that requires sensing of the posture state of patient 12. In alternative examples, clinician programmer 60 may automatically begin the record mode and any other posture state related applications once IMD 14 has been oriented to patient 12. For example, objectification and record modes may be automatically turned on once the orientation process is completed.

Figure 12A:
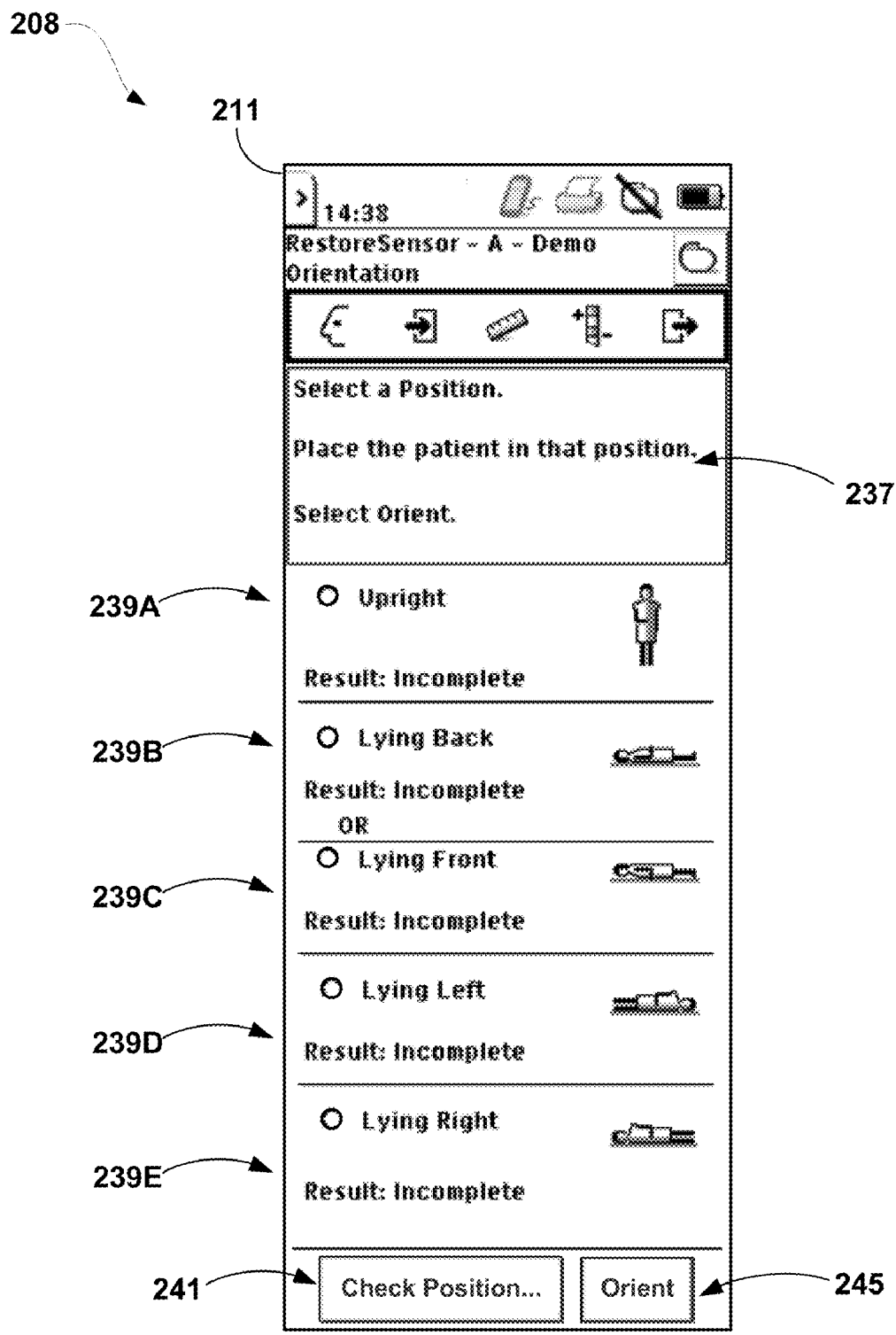
FIGS. 12A and 12B are conceptual diagrams illustrating an example user interface to determine orientation of an implantable medical device without requiring each posture state for orientation.
Figure 12B:
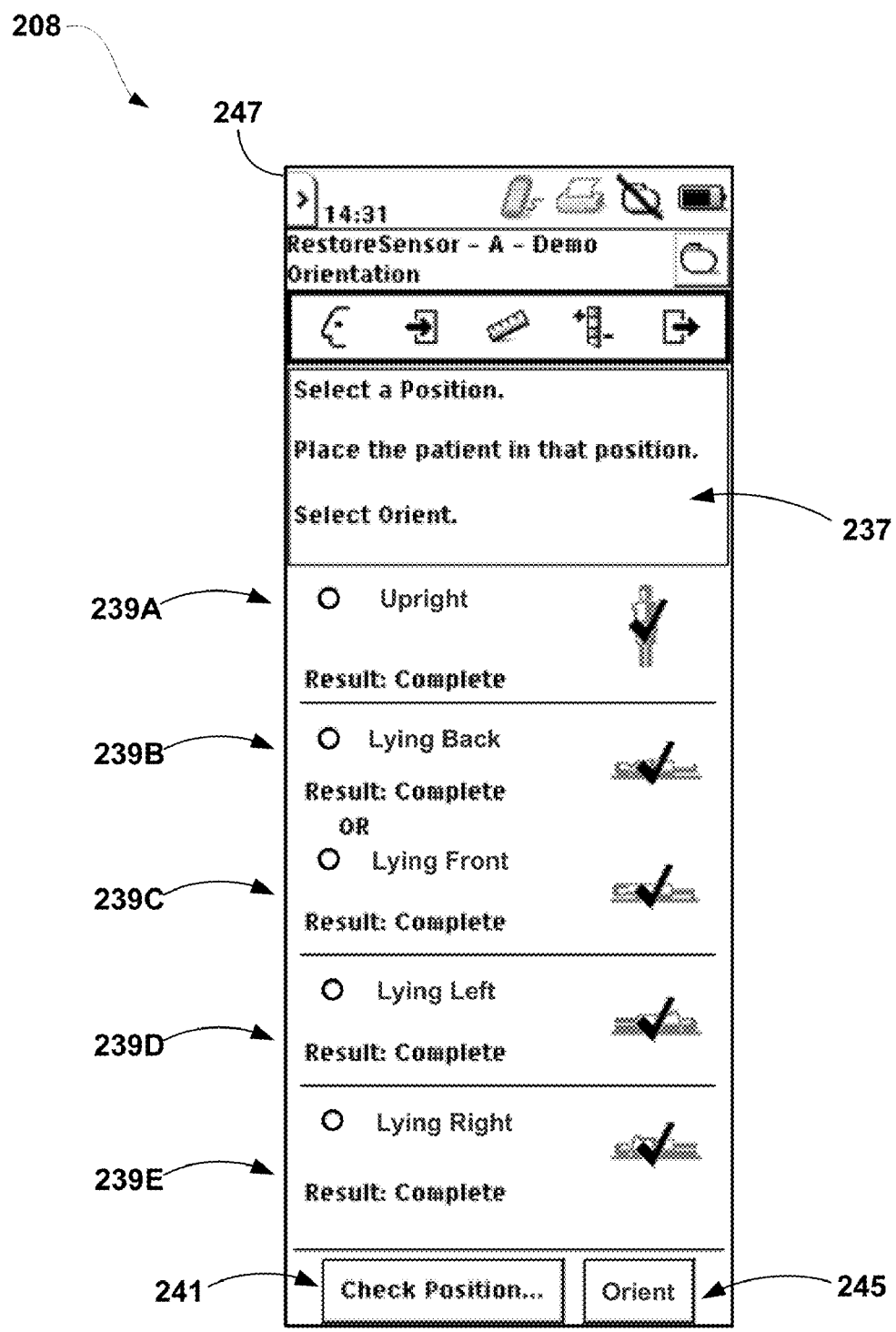

FIGS. 12A and 12B are conceptual diagrams illustrating an example user interface to determine orientation of an implantable medical device without requiring a patient to occupy each posture state for orientation. FIGS. 12A and 12B illustrate example screens 211 and 247 of user interface 208 that are substantially similar to screens 210 and 246 of FIGS. 11A and 11B. However, the example of FIGS. 12A and 12B only require that patient 12 assumes four posture states of the possible five posture states in order to orient IMD 14 to patient 12.

As shown in FIG. 12A, screen 211 of user interface 208 presents orient information 237, posture state selections 239A, 239B, 239C, 239D, and 239E (collectively "posture state selections 239"), position button 241, and orient button 245. The user may select "orient device" or some other text or icon that symbolizes access to the process for initializing the orientation of the posture state sensor within IMD 14.

Screen 211 allows the clinician to initialize the orientation of the posture state sensor of IMD 14 by helping patient 12 assume some of the possible posture states that IMD 14 may detect. Once patient 12 has assumed the appropriate types of posture states indicated by posture state selections 239, the posture state sensor of IMD 14 will be oriented, or calibrated, with pertinent reference coordinate vectors to function as described in this disclosure.

The reference coordinate vectors may be used to define posture cones for different posture states for some posture detection techniques. In some examples, a reference coordinate vector may be used to define an upright cone, and then lying reference coordinate vectors for each of the lying posture states may be used to define lying posture cones, or simply used directly as vectors for cosine- or angle-based proximity testing in some posture detection techniques.

In the example of FIG. 12A, the clinician has not selected the posture state that patient 12 will first assume. Although there are five possible posture states, screen 211 only requires that patient 12 assume four of the five posture states. In any particular order, the clinician orients IMD 14 to the upright position indicated by posture state selection 239A, just one of the lying back or lying front posture states indicated by posture state selections 239B and 239C, the lying left posture state indicated by posture state selection 239D, and the lying right posture state indicated by posture state selection 239E.

The clinician may orient each of these posture states by clicking on the appropriate posture state selection 239, ensuring that patient 12 has assumed that particular posture state, and selecting orient button 245. A sensed coordinate vector is then assigned to the posture state selection as a reference coordinate vector for use in posture detection according to any of the posture detection techniques described in this disclosure. At any time, the clinician may check in which posture state that IMD 14 is detecting patient 12 by selecting position button 241. Upon selecting position button 241, user interface 208 may provide an indication of the current posture state of patient 12. Once each of these posture states is oriented, therapy may proceed as described in this disclosure.

As shown in FIG. 12B, screen 247 of user interface 208 indicates to the clinician that orientation of IMD 14 has been completed for each of the posture state selections 239 as described in FIG. 12A. Each of the posture state selections 239 has a check mark through the graphical posture state indication on the right side of screen 247 to indicate that each posture state selection 239 has been oriented. It should be noted that in an example wherein a lying back posture state is an "opposite" of the lying front posture sate, once either the lying back or lying front posture state has been oriented, both posture state selections 239B and 239C will be checked as completed.

In particular, in an example wherein the reference coordinate vectors for the lying back and lying front posture states are in exactly opposite directions from one another, once a reference coordinate vector is obtained for one of the lying front or lying back posture states, the inverse of that reference coordinate vector may be used for the other of the lying front or lying back posture states. For example, if the reference coordinate vector is obtained for the lying front posture state, then the reference coordinate vector for the lying back posture state is simply the inverse of the lying front reference coordinate vector, and the actual reference coordinate vector for the lying front posture state need not be obtained. Further, as shown in FIG. 12B, orient button 245 has been grayed out so that the clinician cannot select it.

Once clinician programmer 60 is presented with screen 247, the clinician may move on to start the record mode, set programs for each posture state, or any other programming task that requires sensing of the posture state of patient 12. In alternative examples, clinician programmer 60 may automatically begin the record mode and any other posture state related applications once IMD 14 has been oriented to patient 12. For example, objectification and record modes may be automatically turned on once the orientation process is completed.

Figure 13:
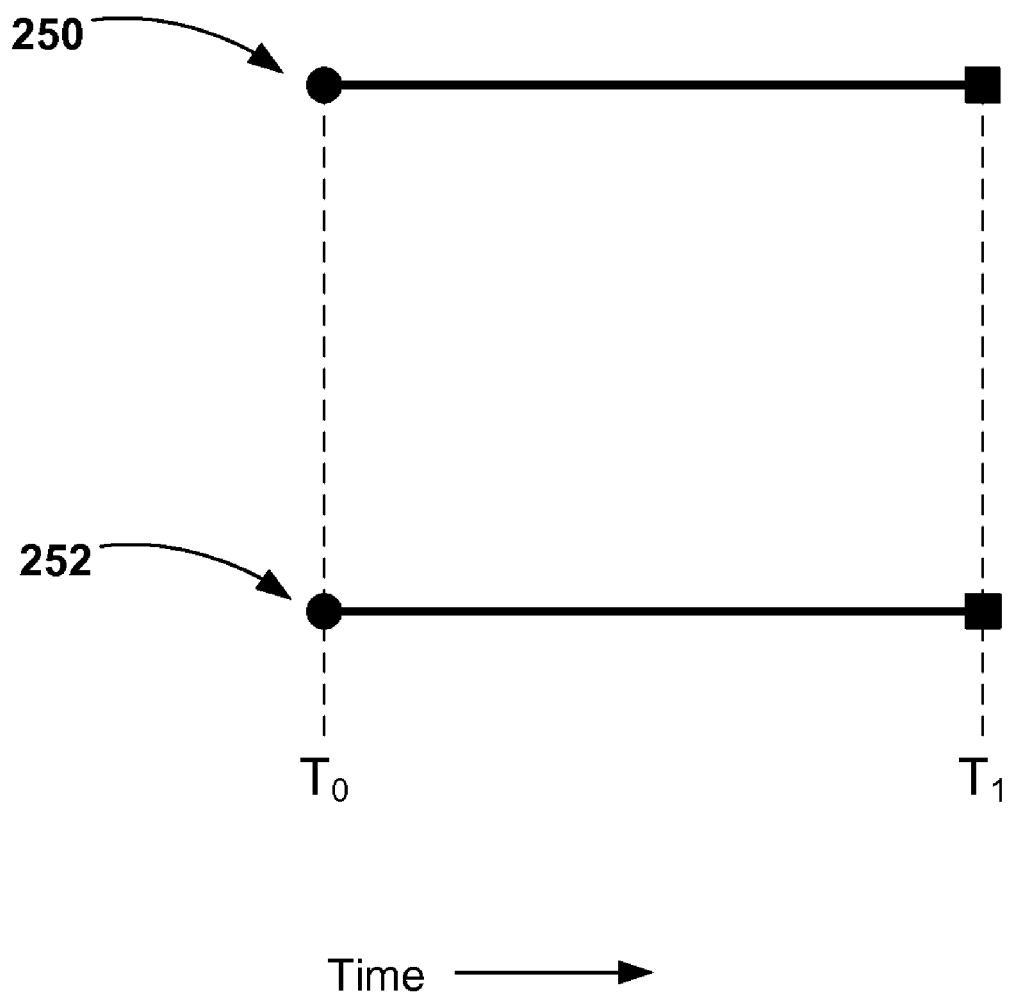
FIG. 13 is a conceptual diagram illustrating example posture search and posture stability timers with only one posture state.

FIG. 13 is a conceptual diagram illustrating example posture search timer 250 and posture stability timer 252 when patient 12 remains in one posture state. As described herein, IMD 14 must be able to correctly associate each therapy adjustment with a therapy parameter to the intended posture state of patient 12 when the therapy adjustment was made. For example, patient 12 may make therapy adjustments to customize the therapy either after patient 12 moves to a different posture state or in anticipation of the next posture state. IMD 14 may employ posture search timer 250 and posture stability timer 252 to track therapy adjustments and the current posture state of patient 12. Although IMD 14 may associate therapy adjustments of any therapy parameter to a posture state, some examples of IMD 14 may only allow the association of amplitude changes. In this manner, patient 12 may change different therapy parameters such as pulse width, pulse rate, or electrode configuration, but IMD 14 will not store these therapy adjustments as being associated to any posture state in some examples.

Posture search timer 250 has a search period that is a set amount of time that patient 12 has from the time the therapy adjustment is made, when posture search timer 250 starts, to when the final posture state must begin, prior to the expiration of the search period. In other words, the therapy adjustment will not be associated with a posture state entered after the search period has expired. In addition, posture stability timer 252 has a stability period that is a set amount of time that patient 12 must remain within the final posture state for the therapy adjustment made to be associated with the final posture state. Posture stability timer 252 restarts at any time that patient 12 changes posture states. In order to associate a therapy adjustment with a posture state, the stability timer for the posture state must start before the end of the search period, and the posture state must not change during the stability period. Therefore, the search period and stability period must overlap for the therapy adjustment to be associated with a posture state not currently engaged by patient 12 when the therapy adjustment was made.

In the example of FIG. 13, patient 12 made a therapy adjustment to one of the therapy parameters, such as voltage or current amplitude, at time $T_0$. Therefore, posture search timer 250 starts at $T_0$ and runs for a predetermined search period until time $T_1$. When the therapy adjustment is made, posture stability timer 252 also starts at time $T_0$ in the current posture state of patient 12 and runs for the stability period. In the example of FIG. 13, the stability period is the same as the search period. Since patient 12 has not changed to any different posture states between times $T_0$ and $T_1$, the stability period also ends at $T_1$. The therapy adjustment made by patient 12 at time $T_0$ is associated with the posture state sensed between times $T_0$ and $T_1$ because both the search period and stability period overlap. In the example of FIG. 13, posture search timer 250 and posture stability timer 252 may not be needed, but their purpose may become clearer in the following examples.

The search period of posture search timer 250 may be of any time duration desired by a device manufacturer, and the clinician may or may not be permitted to set the search period to a desired value or within a predetermined search range. Generally, the search period may be between approximately 30 seconds and 30 minutes, but it may be set to any time desired, including a time that is outside of that range. More specifically, the search period may be between approximately 30 seconds and 5 minutes, or more preferably 2 minutes to 4 minutes in order to provide a reasonable amount of time for patient 12 to be situated in the final desired posture state. In some examples, and as described in the examples of FIGS. 13-17, the search period is approximately 3 minutes. In other cases, shorter search periods may be used, e.g., approximately 1 second to 60 seconds, or approximately 5 seconds to 20 seconds.

In addition, the stability period of posture stability timer 252 may be of any time duration desired by the manufacturer or clinician, where the clinician may or may not be permitted to set the stability period. Generally, the stability period is between approximately 30 seconds and 30 minutes, but it may be set to any time desired, including times outside of that range. More specifically, the stability period may be between approximately 30 seconds and 5 minutes, and more preferably 2 minutes to 4 minutes, in order to ensure that patient 12 is situated in the final desired posture state for a reasonable amount of time and that the final posture state is not just some transitional or interim posture state. In some examples, and as described in the examples of FIGS. 13-17, the stability period is approximately 3 minutes. Although the search period and stability period may have the same duration, they may be different in other examples. In other cases, shorter stability periods may be used, e.g., approximately 1 second to 60 seconds, or approximately 5 seconds to 20 seconds.

As one illustration, reliable association results may be achieved using a search period of approximately 10 to 30 minutes, and a stability period of approximately 2 to 4 minutes, and more preferably approximately 3 minutes. Search and stability periods in these ranges should be effective in supporting reliable associations of patient therapy adjustments with posture states over a range of typical patient behavior. However, other ranges of stability period and search period may be used and, in some cases, search and stability timer ranges may be customized for individual patients.

As described herein, associating therapy adjustments with intended posture states allow the user to review the types of therapy adjustments patient 12 made while assuming, or transitioning to, each posture state. However, the associations may also be used to update therapy parameters used by programs and groups to define the stimulation therapy delivered to patient 12, instead of, or in addition to, simply storing the multiple associations for later review. For example, IMD 14 may determine that a therapy adjustment made by patient 12 to increase the amplitude of the current program is associated with the next posture state assumed by patient 12. IMD 14 may then update and set the program to the associated therapy parameter.

In this case, the next time patient 12 engages in the same posture state as the association, IMD 14 will deliver stimulation therapy according to the increased amplitude made by patient 12 due to the association. Therefore, IMD 14 may use posture search timer 252 and posture stability timer 254 to learn or update program therapy parameters such that IMD 14 remembers the previous therapy parameters of therapy delivery for subsequent delivery according to the engaged posture state. In general, upon detection of a patient adjustment to electrical stimulation therapy delivered to the patient, and sensing of a posture state of the patient, the adjustment is associated with the sensed posture state if the sensed posture state is sensed within a search period following the detection of the adjustment and if the sensed posture state does not change during a stability period following the sensing of the sensed posture state.

Figure 14:
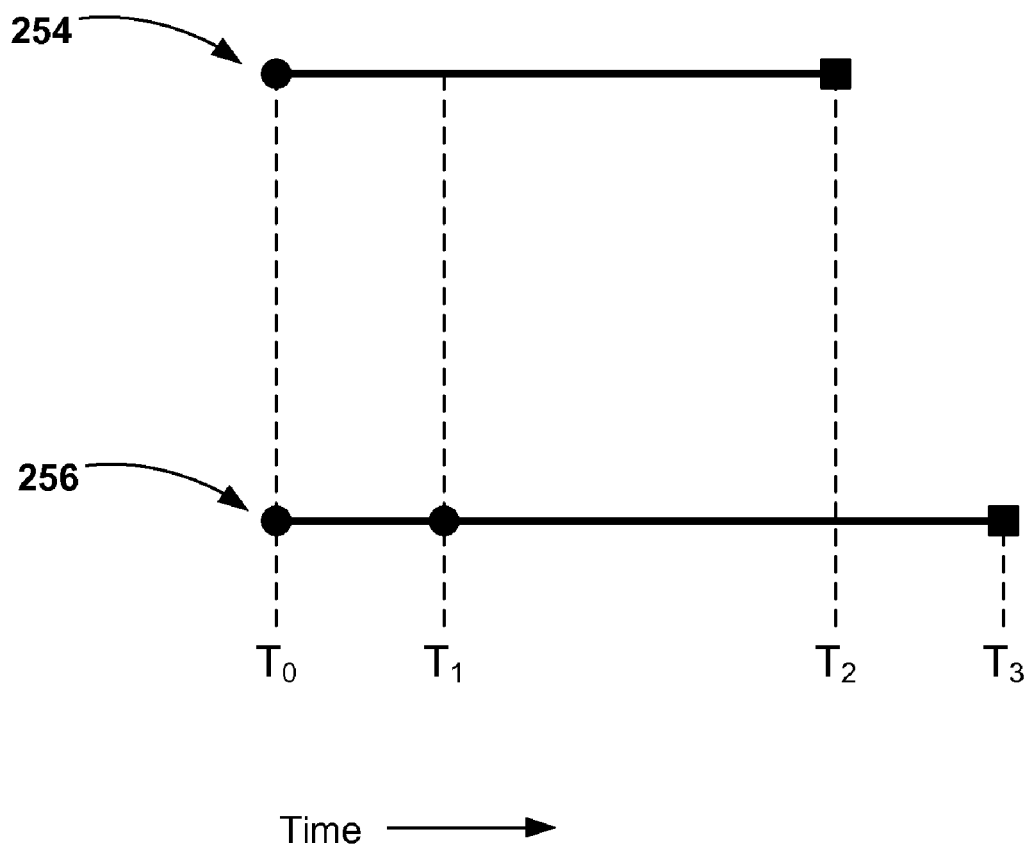
FIG. 14 is a conceptual diagram illustrating example posture search and posture stability timers with one change in posture state.

FIG. 14 is a conceptual diagram illustrating example posture search timer 254 and posture stability timer 256 with one change in posture state. As shown in FIG. 14, patient 12 makes an anticipatory therapy adjustment for the next posture state that patient 12 does not currently occupy. In other words, patient 12 makes a therapy adjustment that the patient may believe is desirable for a given posture in anticipation of transitioning to that posture on an imminent or near-term basis. Posture search timer 254 and posture stability timer 256 start at time $T_0$ when patient 12 makes a therapy adjustment in a current posture state occupied at time $T_0$. At time $T_1$, patient 12 changes to a second posture state that is different than the initial posture state occupied at time $T_0$. Therefore, posture stability timer 256 restarts at time $T_1$, with the change to the new posture state, still within the search duration of posture search timer 254.

In general, patient therapy adjustments received during the search period restart the search period. As a result, a series of patient therapy adjustments that are entered closely in time are, in effect, clustered together such that intermediate adjustments are not associated with the posture state. Instead, the last adjustment in a series of closely spaced (in time) adjustments may be associated with the posture state to represent the final adjustment that brought the parameter to a level or value deemed appropriate by the patient 12 for the given posture state. If the search period is three minutes, for example, and the patient 12 makes four adjustments in voltage amplitude within three minutes of one another, e.g., 4.6 volts to 4.8 volts, 4.8 volts to 5.0 volts, 5.0 volts to 5.1 volts, 5.1 volts to 5.3 volts, then the final adjustment value of 5.3 volts may be associated with the posture state. Each time that a new adjustment is entered within the search period, the search period is reset. Once the final adjustment is made, however, if there are no further adjustments for another three minutes, and the stability period is satisfied for the detected posture state, then the final adjustment is associated with the posture state.

Time $T_2$ indicates the end of posture search timer 254. Consequently, the only posture state that processor 80 of IMD 14 will associate with the therapy adjustment is the second posture state as long as the second posture state satisfies the stability period of posture stability timer 256, i.e., the patient occupies the second posture state for the stability period. At time $T_3$, patient 12 is still in the second posture when the stability period ends, and the therapy adjustment is associated then to the second posture state because the stability period overlapped with the search period.

It should be noted that patient 12 may make additional therapy adjustments within the search period. If this occurs, any previous therapy adjustments made before the search period or stability period is completed are not associated to any posture state. Therefore, both the search period and stability period must lapse, i.e., expire, in order for a therapy adjustment to be associated with a posture state. However, in some examples, IMD 14 may allow therapy adjustments to be associated with posture states as long as the search period has lapsed or no different posture state was sensed during the search period.

Figure 15:
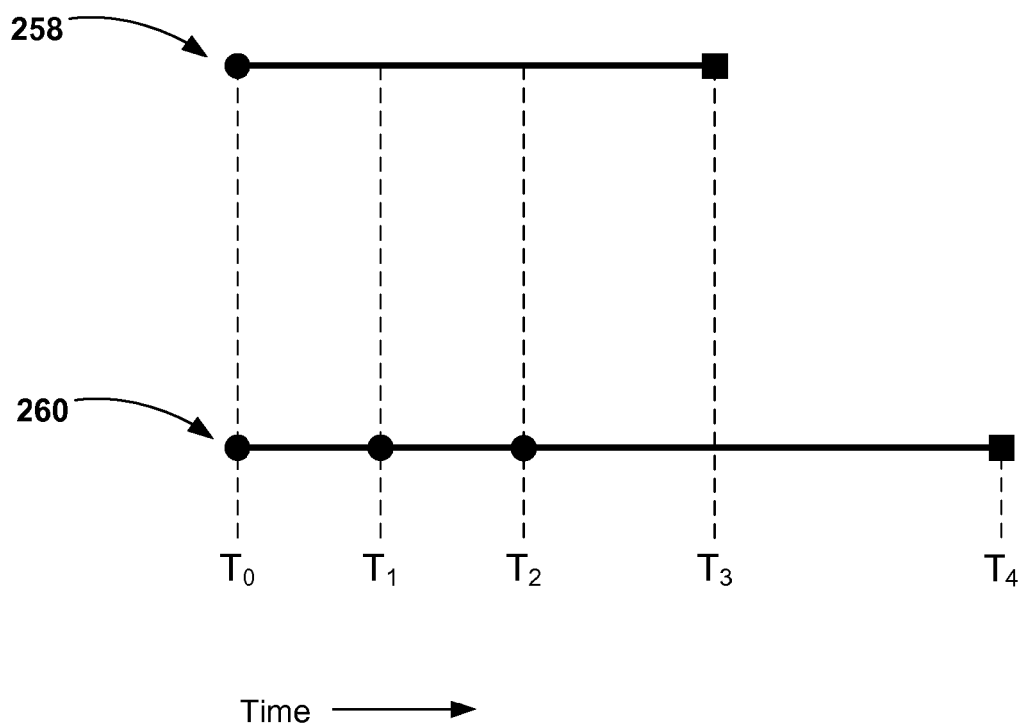
FIG. 15 is a conceptual diagram illustrating example posture search and posture stability timers with two changes in posture states.

FIG. 15 is a conceptual diagram illustrating example posture search timer 258 and posture stability timer 260 with two changes in posture states. As shown in FIG. 15, patient 12 makes an anticipatory therapy adjustment but is engaged in an interim posture state before settling into the final posture state. Posture search timer 258 and posture stability timer 260 both start at time $T_0$ when patient 12 makes a therapy adjustment in a current posture state engaged at time $T_0$.

At time $T_1$, patient 12 changes to a second posture state, or an interim posture state, that is different than the initial posture state engaged at time $T_0$. Therefore, posture stability timer 260 restarts at time $T_1$, still within the search duration of posture search timer 258. At time $T_2$, patient 12 changes to a third posture state, and again posture stability timer 260 restarts. Time $T_3$ indicates the end of posture search timer 258, so the only posture state that processor 80 of IMD 14 will associate with the therapy adjustment is the third posture state begun at time $T_2$ as long as the third posture state satisfies the stability period of posture stability timer 260. At time $T_4$, patient 12 is still in the third posture when the stability period ends, and the therapy adjustment is associated then to the third and final posture state because the stability period of the third posture state overlapped with the search period.

Figure 16:
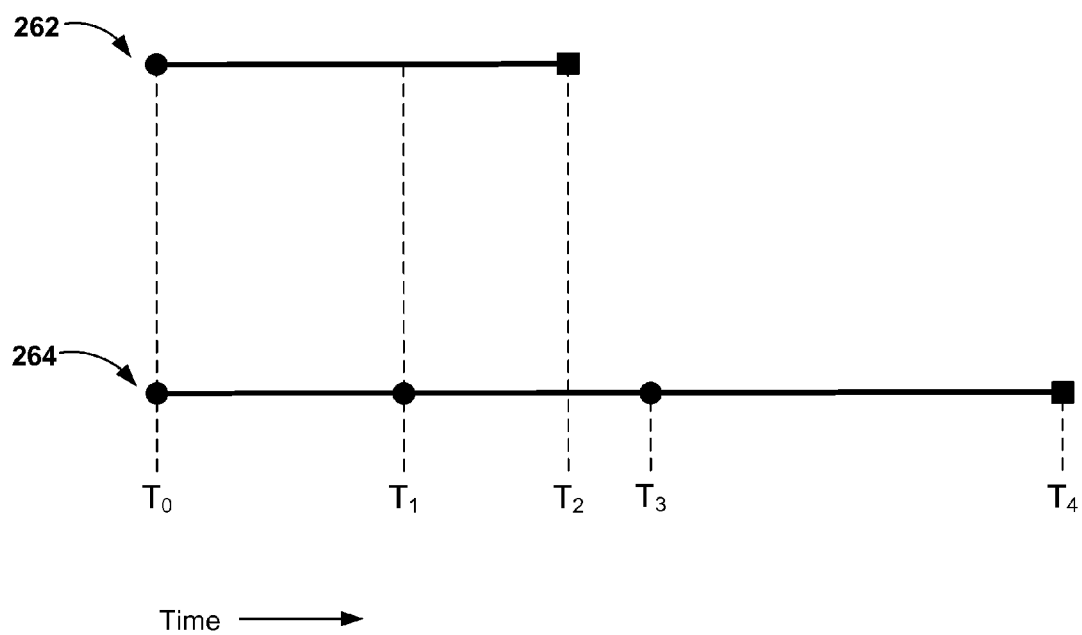
FIG. 16 is a conceptual diagram illustrating example posture search and posture stability timers with the last posture state change occurring outside of the posture search timer.

FIG. 16 is a conceptual diagram illustrating example search timer 262 and posture stability timer 264 with the last posture state change occurring outside of the posture search timer. As shown in FIG. 16, patient 12 makes an anticipatory therapy adjustment but is engaged in an interim posture state too long before settling into the final posture state for the therapy adjustment to be associated with any posture state. Posture search timer 262 and posture stability timer 264 both start at time $T_0$ when patient 12 makes a therapy adjustment in a current posture state engaged at time $T_0$. At time $T_1$, patient 12 changes to a second posture state, or an interim posture state, that is different than the initial posture state engaged at time $T_0$. Therefore, posture stability timer 264 restarts at time $T_1$, still within the search duration of posture search timer 262.

However, the search timer expires at time $T_2$, before patient 12 changes to a third posture state at time $T_3$, when posture stability timer 264 again restarts. The stability period for the third posture state then expires at time $T_4$. Since the third posture state did not start before the search period expired at time $T_2$, the search period and stability period do not overlap and the therapy adjustment from time $T_0$ is not associated to any posture state. In other examples, therapy adjustments may still be associated with the posture state occupied at time $T_0$ when the search period and last stability period do not overlap.

The following is a further illustration of the example described in FIG. 16 to put the example in context of an example patient scenario. Patient 12 may be engaged in the upright posture state when patient 12 makes the therapy adjustment at time $T_0$. In this example, the search duration is three minutes and the stability duration is also three minutes. After two minutes, or at time $T_1$, patient 12 transitions to the lying left posture to cause processor 80 of IMD 14 to restart posture stability timer 260.

If patient 12 remains within the lying left posture for the full three minutes of the stability duration, then the therapy adjustment would be associated with the lying left posture. However, patient 12 leaves the lying left posture after only two minutes, or at time $T_3$, outside of the search duration. At this point the therapy amplitude made at time $T_0$, will not be associated with the next posture state of patient 12. Therefore, the next posture state may be the lying back posture state. Once IMD 14 senses the lying back posture state, IMD 14 may change therapy according to the therapy parameters associated with the lying back posture because IMD 14 is operating in the automatic posture response mode. No new associations with the therapy adjustment would be made in the example of FIG. 16.

Figure 17:
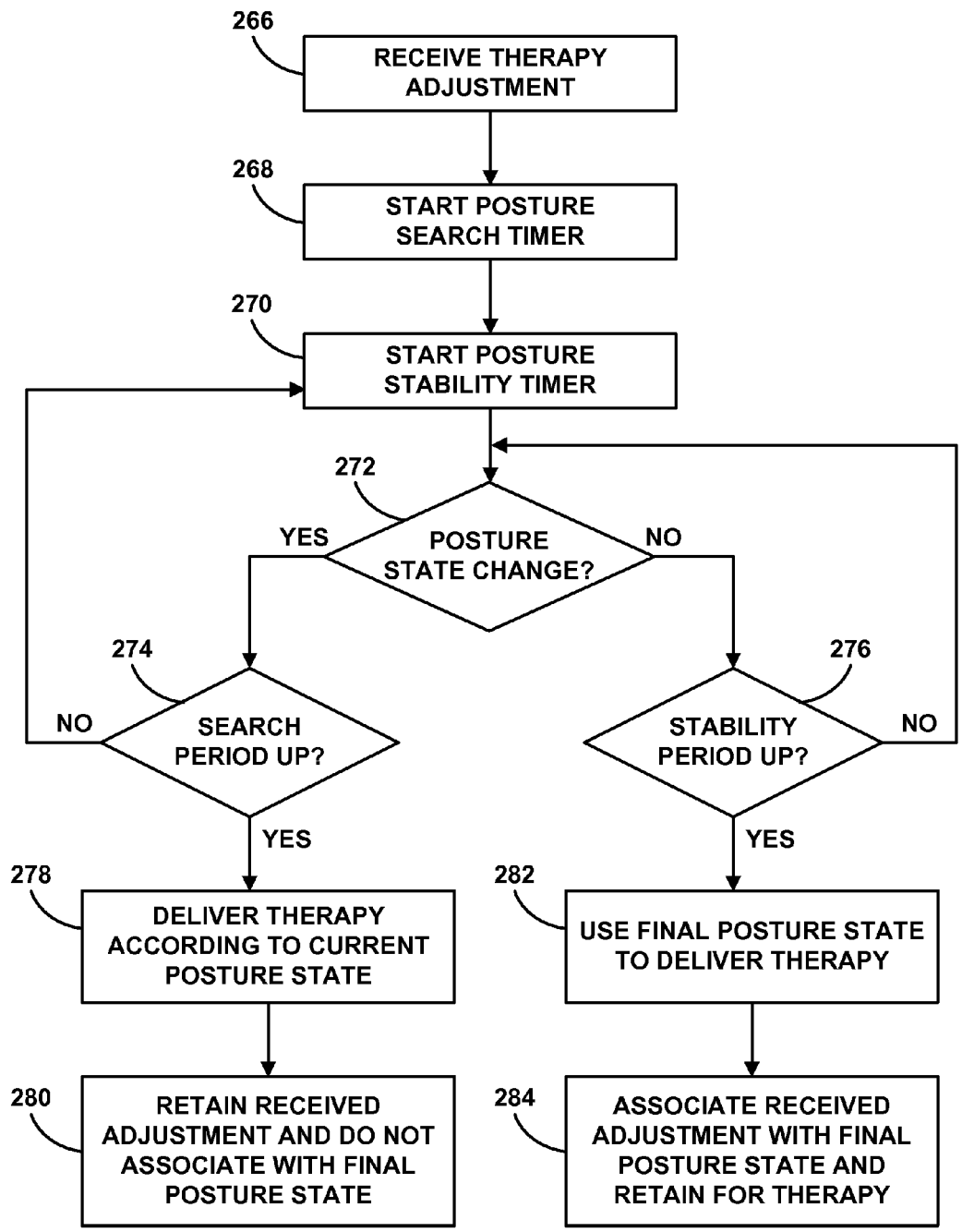
FIG. 17 is a flow diagram illustrating an example method for associating a received therapy adjustment with a posture state.

FIG. 17 is a flow diagram illustrating an example method for associating a received therapy adjustment with a posture state. In general, in a record mode, IMD 14 or an external programmer 20 detecting patient adjustments to electrical stimulation therapy delivered to a patient during multiple instances of a sensed posture state, and associating the detected patient adjustments with the sensed posture state of the patient. The associations can stored in memory for later retrieval to view associations and/or support various programming techniques for programming of therapy parameters for posture state-responsive therapy. Although the example of FIG. 17 will be described with respect to patient programmer 30 and IMD 14, the technique may be employed in any external programmer 20 and IMD or other computing device. As shown in FIG. 17, user interface 106 receives the therapy adjustment from patient 12 (266) and processor 80 of IMD 14 immediately starts the posture search timer (268) and the posture stability timer (270).

If the posture state of patient 12 does not change (272), processor 80 checks to determine if the stability period has expired (276). If the stability period has not expired (276), processor 80 continues to sense for a posture state change (272). If the stability period has expired (276), the processor 80 uses the final posture state, i.e., the currently sensed posture state, to select therapy parameters to deliver therapy (282). Processor 80 then associates the therapy adjustment with the final posture state and retains the therapy adjustment for current therapy (284).

If processor 80 senses a posture state change (272), processor 80 determines if the search period has expired (274). If the search period has not expired (274), then processor 80 restarts the posture stability timer (270). If the search period has expired (274), then processor 80 delivers therapy to patient 12 according to the current posture state (278). Processor 80 retains the therapy adjustment and does not associate the therapy adjustment with the final posture state because the search period did not overlap with the stability period (280). Using the search and stability timers, each of the detected adjustments is associated with a sensed posture state if the sensed posture state is sensed within a search period following the detection of the adjustment and if the sensed posture state does not change during a stability period following the sensing of the sensed posture state.

In some examples, as an alternative, a posture stability timer may be employed without the use of a posture search timer. As described with respect to posture stability timer 260, the posture stability timer may be started after a therapy adjustment and reset each time patient 12 changes posture states prior to expiration of the posture stability timer. When the posture stability timer 260 expires, the therapy adjustment may be associated with the posture state that patient 12 is occupying at that time. In this manner, the therapy adjustment may be associated with the first stable posture state, i.e., the first posture state that remains stable for the duration of the posture stability timer, after the therapy adjustment, regardless of the amount of time that has past since the therapy adjustment. Hence, in some implementations, processor 80 may apply only a stability timer without a search timer. In some cases, the use of only a stability timer, without a search timer, may be approximated by setting the search timer value to a large value, such as 24 hours. The effect of a very large search timer value is to operate with only a stability timer.

It should be noted that, in an example implementation, processor 80 may not change therapy to patient 12 at any time until the stability period expires. In other words, the posture stability timer may run independently of the posture search timer to always track posture states independently of therapy adjustments. Therefore, IMD 14 may not perform any automatic posture state-responsive stimulation until the posture state of patient 12 is stable and the stability period has expired. In this manner, patient 12 may not be subjected to rapidly changing therapy when transitioning between multiple posture states. Alternatively, IMD 14 may employ a separate posture stability timer for changing therapy during automatic posture response from the therapy adjustment related posture stability timer described herein.

Figure 18:
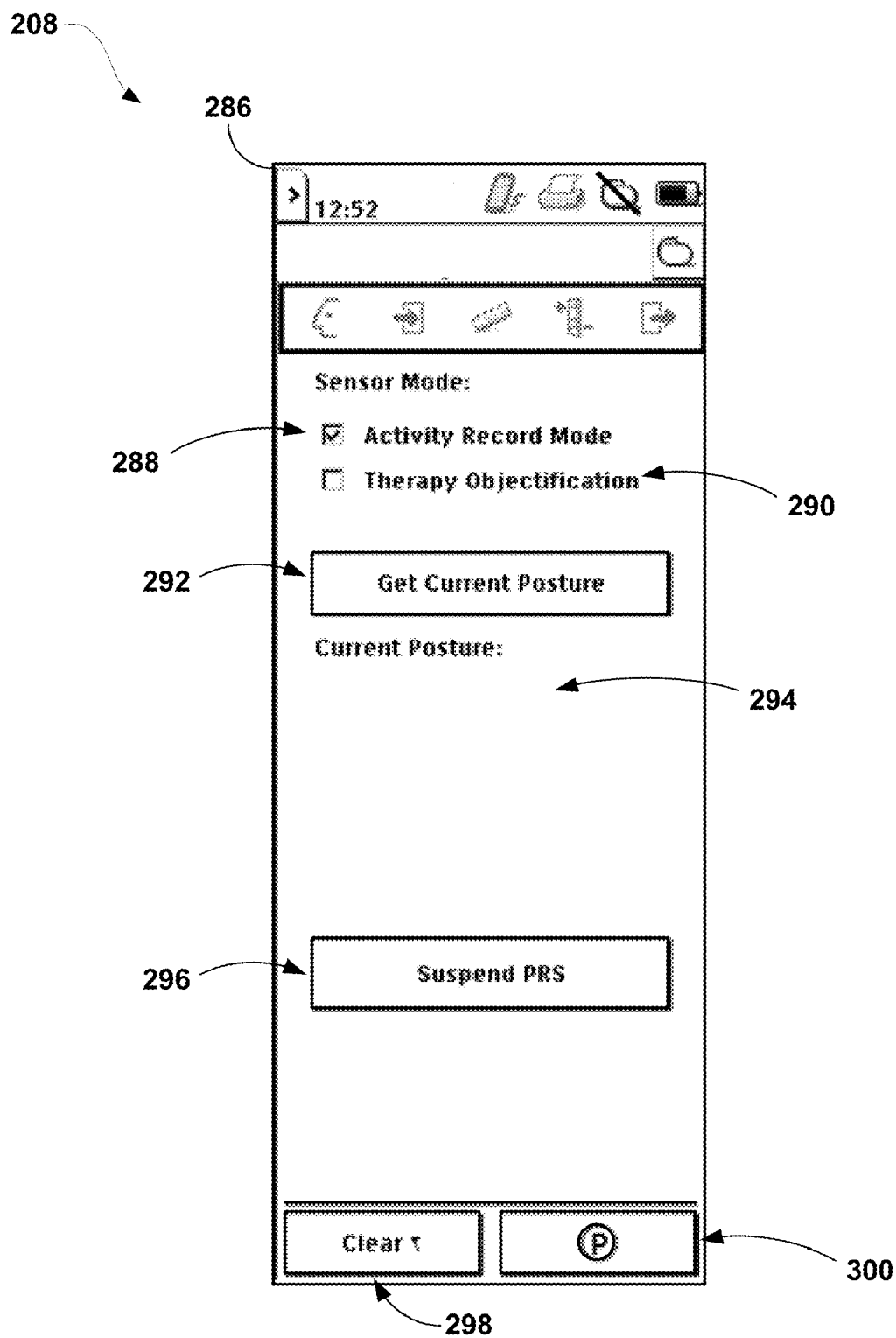
FIG. 18 is a conceptual diagram illustrating an example user interface for initiating the record mode that stores therapy adjustments for each posture state.

FIG. 18 is a conceptual diagram illustrating an example user interface 208 for initiating the record mode that stores therapy adjustments for each posture state. As shown in FIG. 18, screen 286 of user interface 208 allows the clinician to initiate or enable the record mode that associates therapy adjustments to posture states and stores the associations within IMD 14 and/or external programmer 20. FIG. 18 is an example of clinician programmer 60 displaying user interface 208, but any programmer 20 may be used. Record mode selection 288 is checked to show that the clinician desires to initiate the record mode. The clinician also has the opportunity in screen 286 to enable and store objectification data related to posture state information. As mentioned previously, objectification data may be automatically stored unless the clinician turns off that application. For example, objectification and/or record modes may be automatically turned on once the orientation process is completed.

Screen 286 may also allow the clinician to check the orientation of the posture state sensor of IMD 14 by selecting posture button 292. The current posture would then be displayed in posture field 294. In some examples, the posture state of patient 12 may be presented as a picture or icon of the patient body, posture state, the posture cone used, a two dimensional or three dimensional vector illustrating the position of the body of the patient 12 relative to the cones, or simply the current output coordinates of the posture state sensor. The clinician may also be able to turn on or suspend the automatic posture responsive stimulation that changes therapy based upon the sensed posture state of patient 12, with posture control button 296. After the clinician checks to enable the record mode selection 288, the clinician may select program button 300 to enable the record mode. Alternatively, the clinician may select clear button 298 to erase any selections on screen 286.

Figure 19:
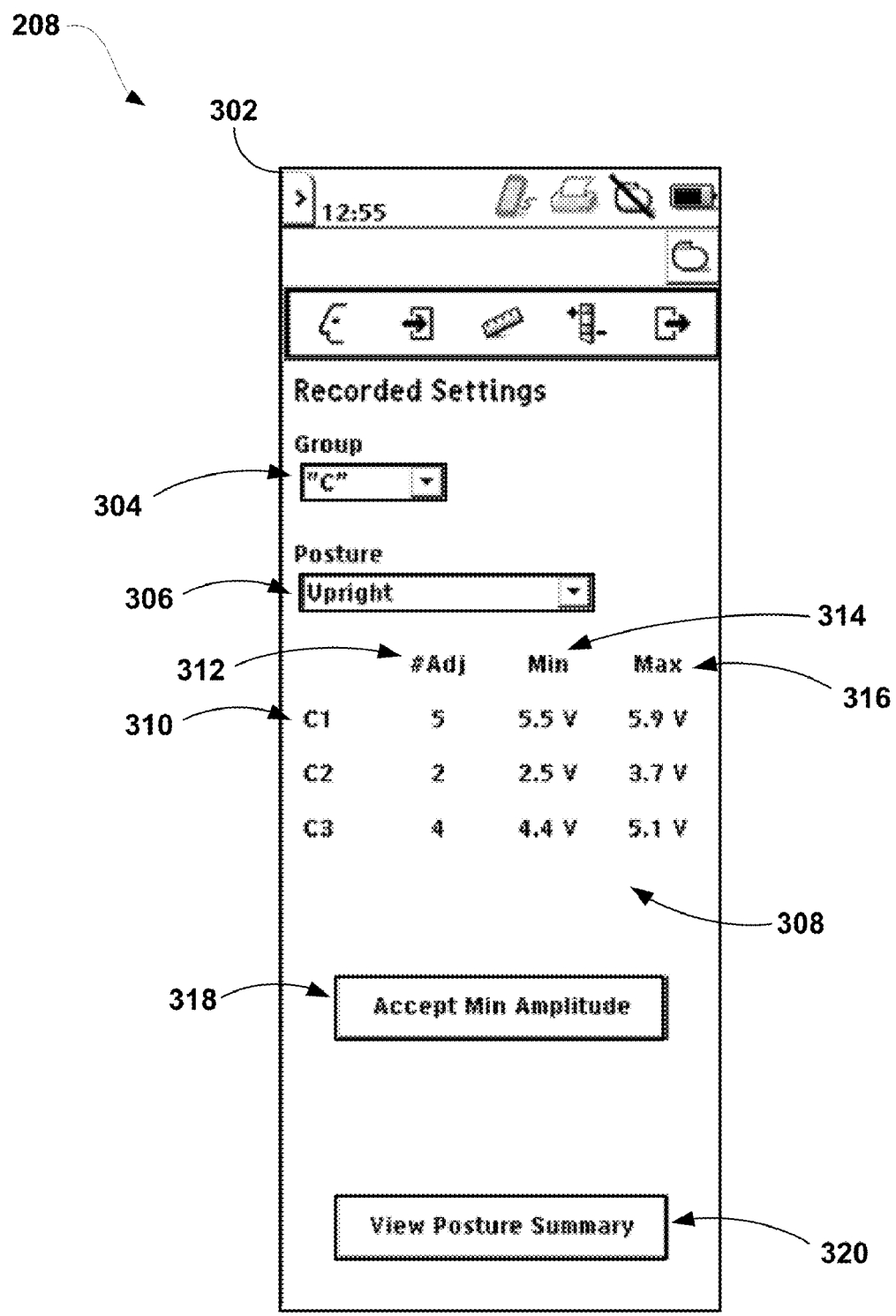
FIG. 19 is a conceptual diagram illustrating an example user interface showing stored adjustment information and allowing one-click programming.

FIGS. 19-26 are directed to clinician programmer 60, but could also be directed to any other external programmer 20. FIG. 19 is a conceptual diagram illustrating an example user interface 208 showing stored adjustment information and allowing programming with a single confirmation input, i.e., one-click programming. As shown in FIG. 19, screen 302 of user interface 208 presents associated therapy adjustment information in addition to allowing the clinician to set a nominal therapy parameter for a plurality of programs with a single confirmation input. Screen 302 includes group menu 304, posture state menu 306, therapy adjustment information 308, confirmation button 318, and summary button 320.

In general, screen 302 presents therapy adjustment information to a user. The therapy adjustment information includes one or more therapy adjustments made by a patient to at least one stimulation parameter of one or more stimulation therapy programs for one or more patient posture states. Upon receiving input from the user that selects one or more nominal therapy parameters for each of the therapy programs and for each of the posture states based on the therapy adjustment information, programmer sets the selected nominal therapy parameters for each of the therapy programs and posture states for use in delivering stimulation therapy to the patient.

Group menu 304 allows the clinician to select the desired group of programs to be displayed on screen 302. The groups presented in group menu 304 may be static and not changeable during a programming session with the clinician. However, some examples of user interface 208 may allow newly added or deleted groups to be shown in updated group menu 304. In addition, group menu 304 may only show groups in which automatic posture response is currently active. If a device with groups A, B and C is interrogated, and then groups D and E are added during a programming session, the group list may not update in some configurations of the programmer and IMD. In other examples, however, the group list could update automatically. The list could be filtered based on which groups are enabled for posture-responsive therapy and which are not.

Currently, in the example of FIG. 19, the clinician has selected program group "C," which is also the group currently selected to deliver stimulation therapy because of the quotation marks around the group letter. Alternatively, the active group could be indicated with any other indication representative that the group currently delivers therapy. Posture state menu 306 also allows the clinician to select the desired posture state so that the therapy adjustment information that is presented is related to the selected posture state. In particular, therapy adjustment information may be displayed to indicate adjustments made by the patient for a particular program while occupying a particular posture state. In FIG. 19, the clinician has selected the upright posture state in posture state menu 306, and group C in the group menu 304. As a result, screen 302 of the programmer 60 presents minimum and maximum values selected by the patient for the individual programs in group C while the patient occupied the upright posture state.

Therapy adjustment information 308 includes multiple fields that include data derived from the therapy adjustment information stored within IMD 14, patient programmer 30, or clinician programmer 60. Program field 310 presents each program (C1, C2, C3) for the selected group (C). Adjustment field 312 presents the quantified number of adjustments (# Adj) patient 12 made for each of the programs for a given posture state (e.g., Upright in FIG. 19). The number of adjustments may be a total or an average over a specific time interval, such as an hour, day, week, or month, or over an open-ended time interval, such as a therapy session running between successive programming sessions, which may be in-clinic or remote programming sessions in which IMD 14 is programmed with updating program parameters.

Minimum field 314 presents the minimum amplitude that patient 12 adjusted for each program, and maximum field 316 presents the maximum amplitude that patient 12 adjusted for each program. Therefore, minimum field 314 and maximum field 316 provide an amplitude range for each program within which patient 12 received stimulation therapy while occupying a particular posture. For example, program C1 was used to deliver stimulation therapy with an amplitude between 5.5 volts (V) and 5.9 V, where 5.5 volts was the minimum amplitude selected by the patient and 5.9 V was the maximum selected by the patient in the relevant time interval while occupying the relevant posture state (e.g., Upright in FIG. 19). The amplitude is provided in volts but IMD 14 alternatively may deliver stimulation as constant current. However, if IMD 14 delivers stimulation with constant current, the amplitude instead may be indicative of a current amplitude displayed in amps.

With therapy adjustment information 308 presented to the clinician, screen 302 also allows the clinician to make changes to the therapy parameters of each of the programs shown on screen 302. In the example of FIG. 19, the nominal therapy parameter for a program is the minimum amplitude of the recorded therapy adjustments for that posture state. The clinician may desire to set all of the programs of group "C" to their minimum amplitudes for the given posture by selecting confirmation button 318, a confirmation input, only one time. The nominal therapy parameter may be a therapy parameter selected from the therapy adjustments stored in the IMD. In other words, in this example, the nominal therapy adjustment is not weighted or calculated according to an algorithm. In this manner, programming time may be decreased because the clinician may be provided with a therapy parameter for programming and the programming of a plurality of programs for a given posture state may be completed with only a single click of confirmation button 318. Upon selecting summary button 320, clinician programmer 60 will present additional posture state information or therapy adjustment information, such as the total number of therapy adjustments associated with each posture state, as shown in FIG. 24.

As illustrated in FIG. 19 and discussed above, by selecting program group via group menu 304 and posture state via posture state menu 306, a user can view a number of adjustments 312 by the patient, minimum values 314 selected by the patient, and maximum values selected by the patient for the programs C1-C3 in the program group and particular posture states in which the adjustments were made. Hence, the user may view this information for different program groups and different posture states, and then apply the pertinent minimum amplitude as the nominal amplitude for the respective program and posture state, e.g., via confirmation button 318. Then, when posture responsive therapy is running, the IMD 14 will deliver stimulation with the pertinent minimum amplitude when the patient is applying the respective program while occupying the respective posture state.

Screen 302 only presents recorded amplitudes that were associated with each posture state for each program, and may not show pulse width, pulse rate and electrode configuration. However, screen 302 may alternatively be configured to show other stimulation therapy parameter values in addition to the amplitudes or provide a link for the user to view the additional therapy parameters. Although only therapy adjustments to amplitude are associated and stored in IMD 14 in this example, other therapy parameter adjustments may also be recorded in some examples. The association of therapy adjustments could be performed for any one or more of the therapy parameter values that define each program, and even non-associated therapy parameters values may be presented to the user via user interface 208. If only amplitude adjustments are used, it may be implied that each amplitude adjustment assumes constant pulse width, pulse rate and electrode configuration for each amplitude adjustment. In other examples, if patient 12 makes a change to pulse width, pulse rate, or electrode configuration during therapy, any associated amplitudes to that changed program may be erased because the association of amplitude are no longer based on the original therapy parameters used when the associations were made.

In addition, screen 302 may not always allow the clinician to confirm therapy parameter changes to groups or programs deleted and re-added to therapy since therapy adjustments were associated. In other words, the groups and programs for which associations were made during use by patient 12 can only be modified using the stored therapy adjustments when the groups and programs presence for therapy is consistent. Further, if any leads, in the case of electrical stimulation, have been reconfigured for therapy, user interface 208 may prevent the clinician from making any changes to the therapy parameters using confirmation button 318. These restrictions of making changes to therapy may be desired to prevent the clinician from making inappropriate changes to therapy.

Although screen 302 only shows the programs for one group at a time, and for one posture state at a time, alternative examples of user interface 208 may provide more than one group of programs and more than one posture state at one time. Then, the clinician may be able to set more of the therapy parameters for multiple groups of programs with a single click of confirmation button 318. In other examples, the clinician may be able to select a global confirmation button (not shown) that sets the nominal therapy parameter for every program within IMD 14 with a single click of the global confirmation button.

Again, it may be implicit that the amplitudes that are recorded and shown have a constant pulse width, pulse rate, and electrode configuration. If, during the course of a programming session, the user changes the electrode configuration, pulse width, pulse rate or any parameter that is not listed on this screen (because it was implicit), the confirmation button 318 may be grayed out for that group only, because the recorded amplitudes only were valid in conjunction with the implicit pulse width, rate, and electrode configuration. If a group is deleted and then re-added (e.g., B is deleted and then re-created), the confirmation button 318 may be grayed for that group. If a program is either added or deleted in a group, confirmation button 318 may be grayed out for that group. If the lead configuration is changed, confirmation button 318 may be grayed out for all groups used for therapy.

Figure 20:
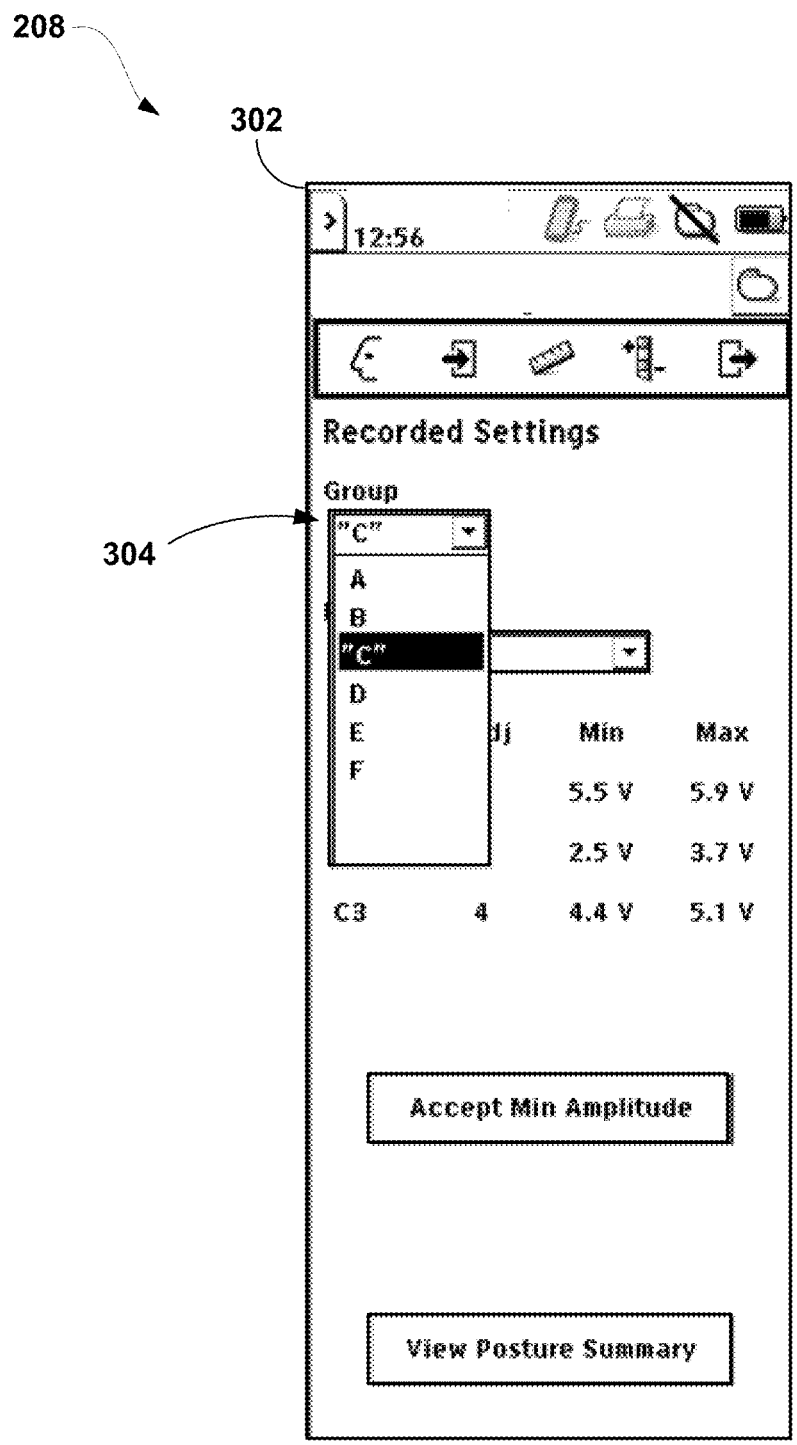
FIG. 20 is a conceptual diagram illustrating an example user interface showing user selection of a program group.

FIG. 20 is a conceptual diagram illustrating an example user interface 208 showing user selection of a program group. As shown in FIG. 20, screen 302 presents the therapy adjustment information from the record mode. Specifically, group menu 304 is shown in the drop-down form that allows the clinician to select which group of programs will be presented on screen 302. In the example of FIG. 20, available groups are A, B, C, D, E, and F, but group menu 304 may have more or less groups depending on how the clinician programmed stimulation therapy. In other examples, group menu 304 may be a scrollable list, a text field for the clinician to enter the desired group, or some other menu that allows the clinician to select the desired group. Alternatively, the clinician may be able to select multiple groups at one time from group menu 304.

Figure 21:
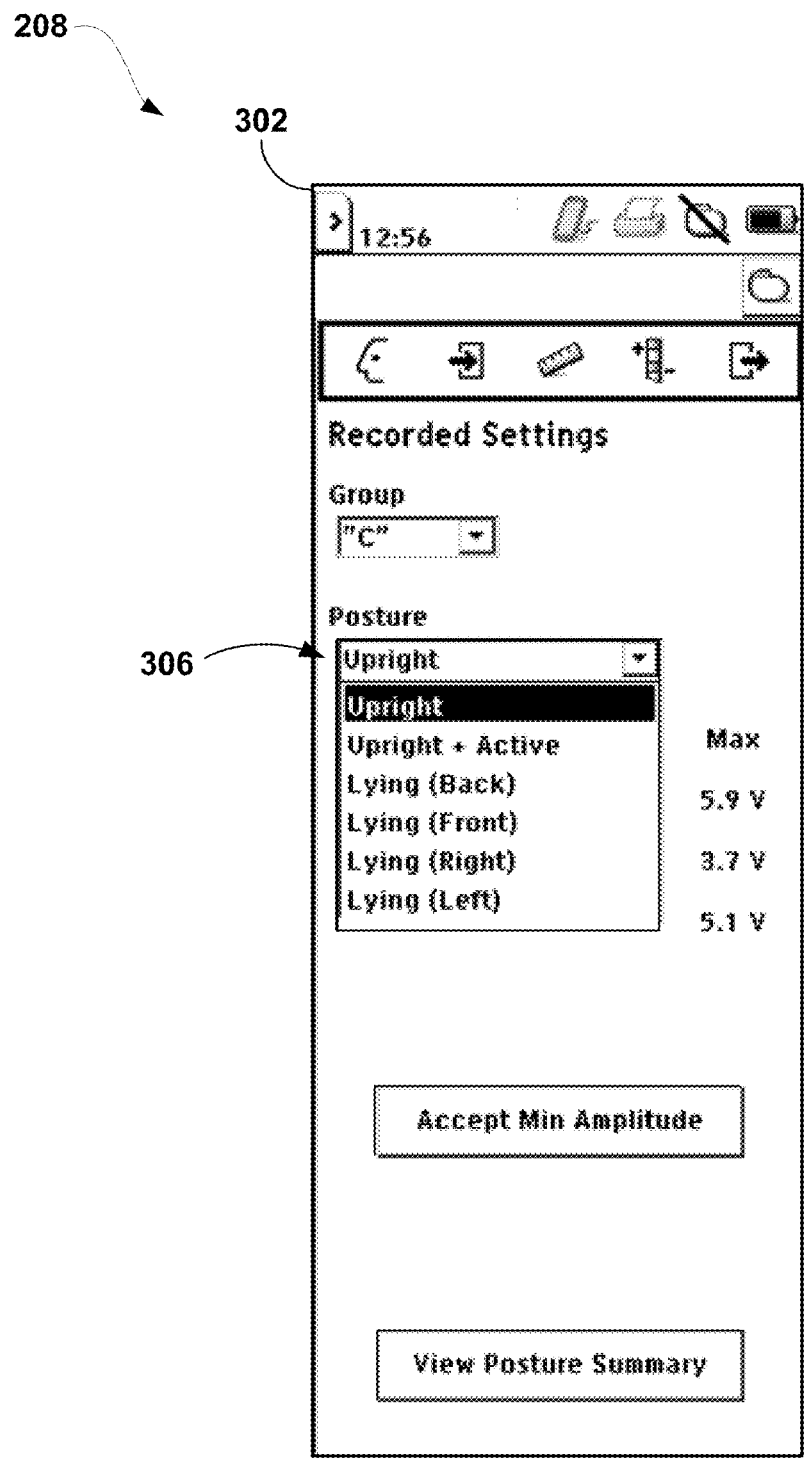
FIG. 21 is a conceptual diagram illustrating an example user interface showing user selection of a posture state.

FIG. 21 is a conceptual diagram illustrating an example user interface 208 showing user selection of a posture state. In the example of FIG. 21, posture state menu 306 of screen 302 is in the drop-down form to allow the clinician to select the desired posture state for which therapy adjustment information will be presented. The available posture states are upright, upright and active, lying back, lying front, lying right, and lying left. In some examples, if any posture states do not have associated therapy adjustments for any programs of the selected group, that posture state may either be grayed out or absent from posture state menu 306. Further, user interface 208 may allow multiple posture states to be selected from posture state menu 306 when multiple posture states can be presented on screen 302. In other examples, posture state menu 306 may be a scrollable list, a text field for the clinician to enter the desired posture state, or some other menu that allows the clinician to select the desired posture state to be presented.

Figure 22:
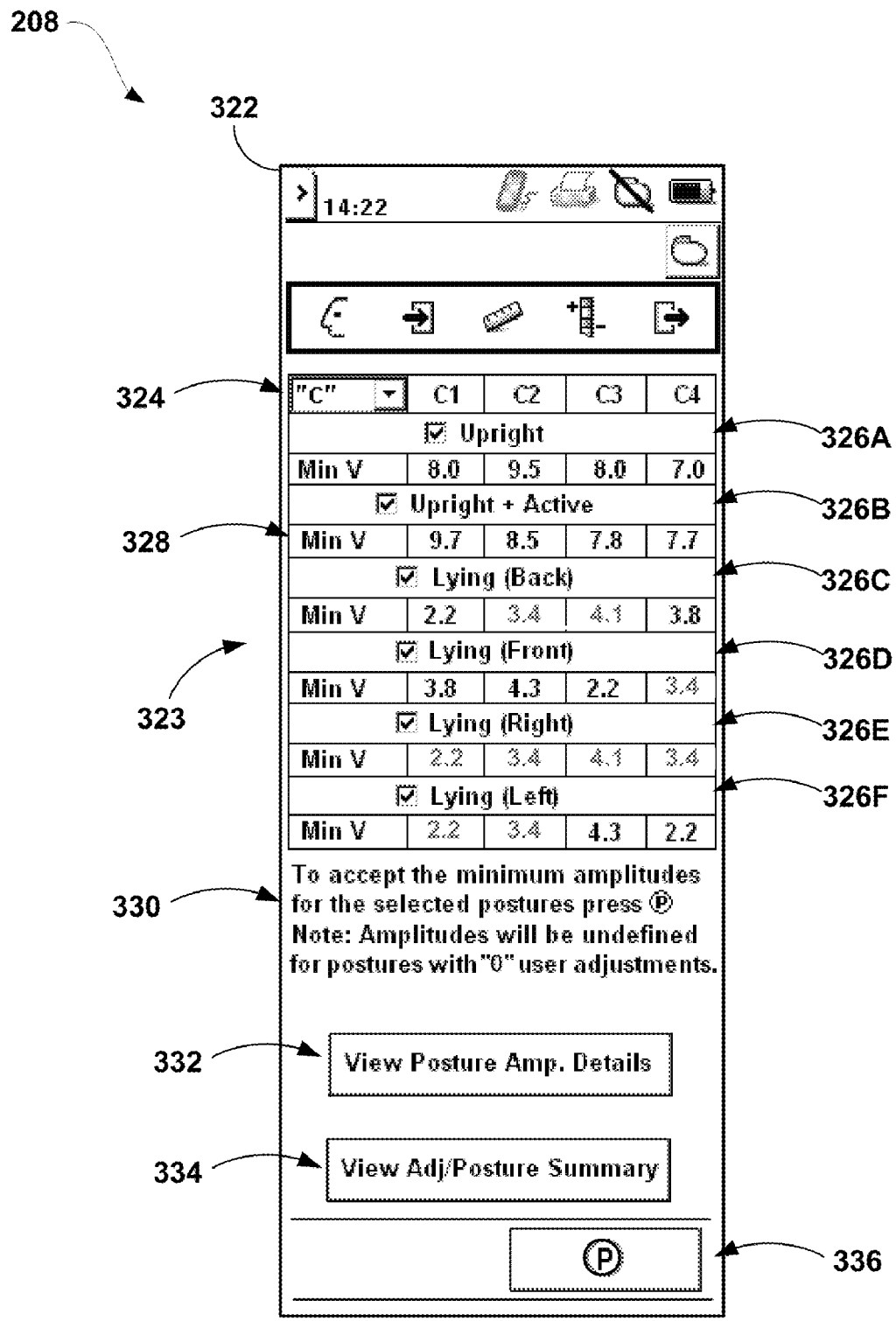
FIG. 22 is a conceptual diagram illustrating an example user interface showing stored adjustment information for all posture states of a program group to allow one-click programming.

FIG. 22 is a conceptual diagram illustrating an example user interface 208 showing stored therapy adjustment information 323 for all posture states and all programs of a program group to allow one-click programming. FIG. 22 is an alternative presentation of therapy adjustment information shown in FIGS. 19-21. As shown in FIG. 22, screen 322 of user interface 208 presents therapy adjustment information 323 stored during the record mode of therapy. Screen 322 includes group menu 324, posture states 326A, 326B, 326C, 326D, 326E, and 326F (collectively "posture state selections 326"), minimum amplitudes 328, programming information 330, detail button 332, and summary button 334, and confirmation button 336.

Group "C" has been selected in group menu 324, so all four programs C1, C2, C3, and C4 are shown for the group. Therapy adjustment information 323 includes the minimum amplitude 328 that patient 12 adjusted for each program of the selected group in relation to each of posture state selections 326. For example, minimum patient-selected amplitudes of 8.0, 9.7, 2.2, and 3.8 volts are shown for program C1 when the patient occupied the upright, upright and active, lying back and lying front posture states, respectively. Grayed out minimum amplitudes of therapy adjustment information 323, e.g., all minimum amplitudes for lying right posture state selection 326E, indicate that no therapy adjustments were made by patient 12 to set the minimum amplitude for that posture state and group. In this manner, the clinician may identify the posture states for which patient 12 has made therapy adjustments. In alternative examples, screen 322 may present a different nominal therapy parameter than minimum amplitudes 328. For example, screen 322 may present maximum amplitudes or the last used amplitudes.

Programming information 330 provides the clinician with information on how to set the nominal therapy parameters of minimum amplitudes 328 to all of the programs. Specifically, the clinician only needs to click on confirmation button 336 to program each of the programs C1-C4 with the presented minimum amplitudes for each posture state. This single click dramatically reduces the amount of time needed to normally program the new stimulation parameter for each of the programs in each posture state. In addition, the clinician may select detail button 332 to view therapy adjustment details, as shown in FIG. 23, and summary button 334 to view the total number of therapy adjustments for each posture state, as shown in FIG. 24.

Figure 23:
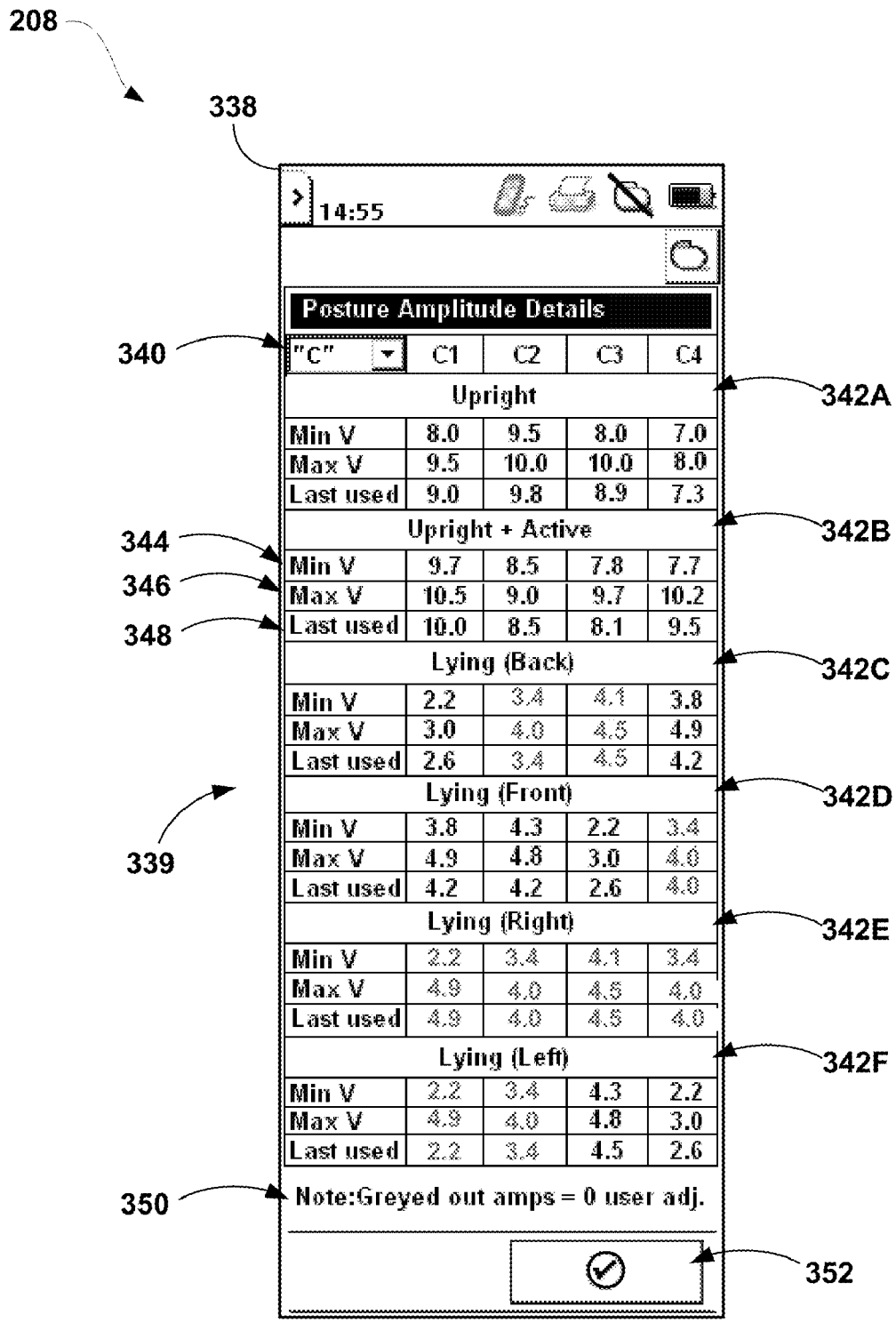
FIG. 23 is a conceptual diagram illustrating an example user interface showing detailed adjustment information associated with FIG. 22.

FIG. 23 is a conceptual diagram illustrating an example user interface 208 showing detailed adjustment information associated with FIG. 22. As shown in FIG. 23, screen 338 of user interface 208 is navigated to by the clinician via selection of detail button 332 of screen 322 or some other menu option of user interface 208. Screen 338 presents therapy adjustment information 339 stored within IMD 14 during the record mode. The clinician may select which group to view via group menu 340 and when to return to screen 322 by selecting return button 352.

For each program of the selected group, screen 338 presents posture states 342A, 342B, 342C, 342D, 342E, and 342F (collectively "posture state selections 342"). Also, for each program and each posture state selection 342, minimum amplitudes 344, maximum amplitudes 346, and last used amplitudes 348 are presented to the clinician. Therefore, the clinician may review the entire range of amplitudes used by patient 12 in addition to the last used amplitude that may indicate which direction the therapy is progressing. As indicated by note 350, grayed out amplitudes may indicate that they have not been adjusted by patient 12. In other examples, screen 338 may present the number of therapy adjustments to each program in each posture state in addition to, or instead of, last used amplitudes 348. Other information related to therapy adjustments and posture state information may also be presented in alternative examples of screen 338.

In other examples, the therapy adjustment information may be arranged differently on screen 338. For example, any unadjusted posture states may be removed from screen 338 because patient 12 has not used those posture states. Alternatively, therapy adjustment information may include a mean or median amplitude for each program and posture state selection 342. Further, upon the selection of an amplitude within therapy adjustment information 339, user interface 208 may display additional data, such as each therapy adjustment, the time and date stamp of each adjustment, the average adjustment for each day within the last week, month, year, or entire therapy, or any other detailed amplitude information. In some examples, therapy information may provide adjustments to other therapy parameters, such as pulse width, pulse rate, or electrode configuration. Of course, any therapy adjustment information related to drug delivery therapy and IMD 26 may be presented to the clinician if drug delivery is used instead of or in addition to electrical stimulation therapy.

Figure 24A:
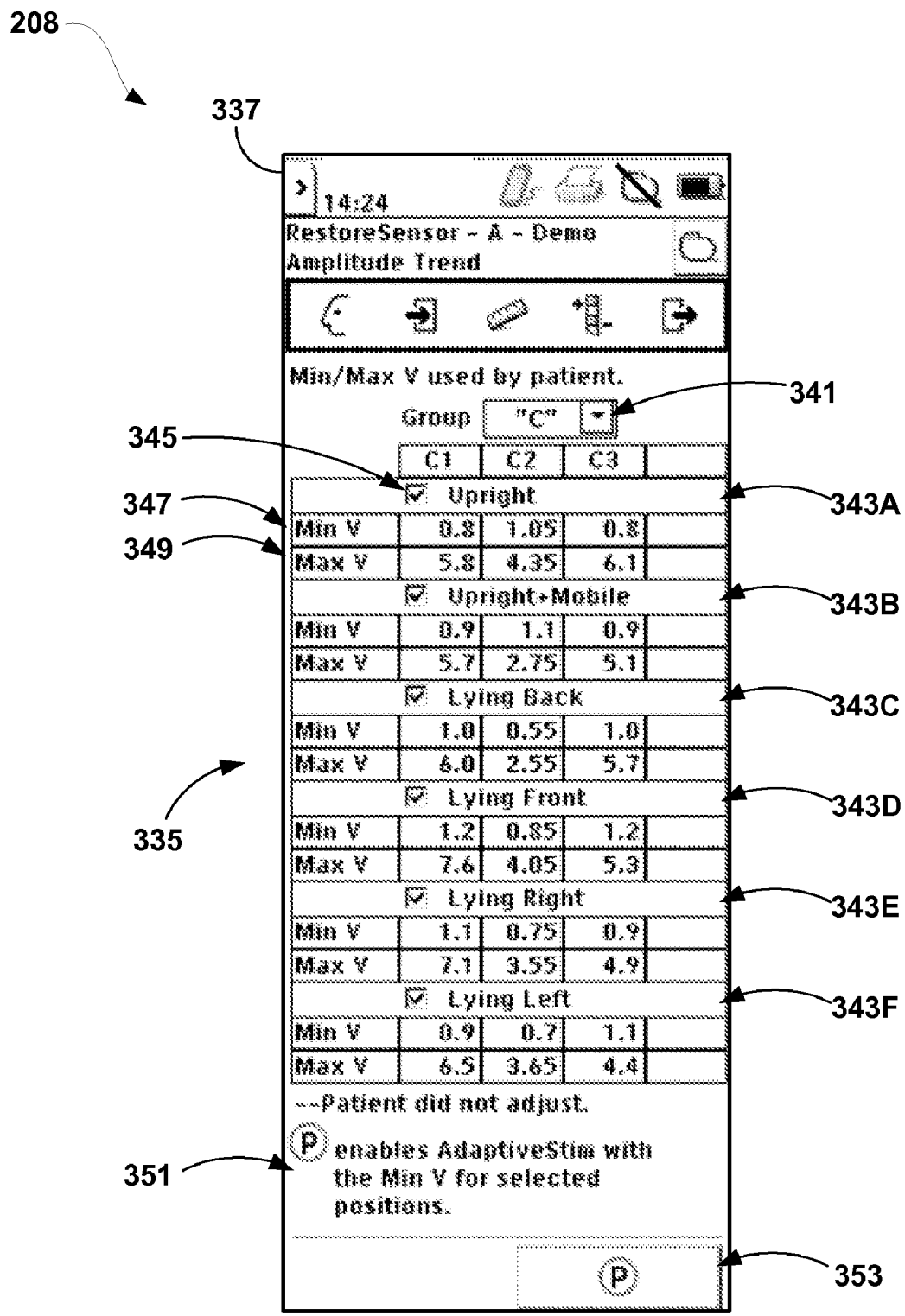
FIGS. 24A and 24B are conceptual diagrams illustrating an example user interface showing maximum and minimum therapy adjustments associated for each posture state.
Figure 24B:
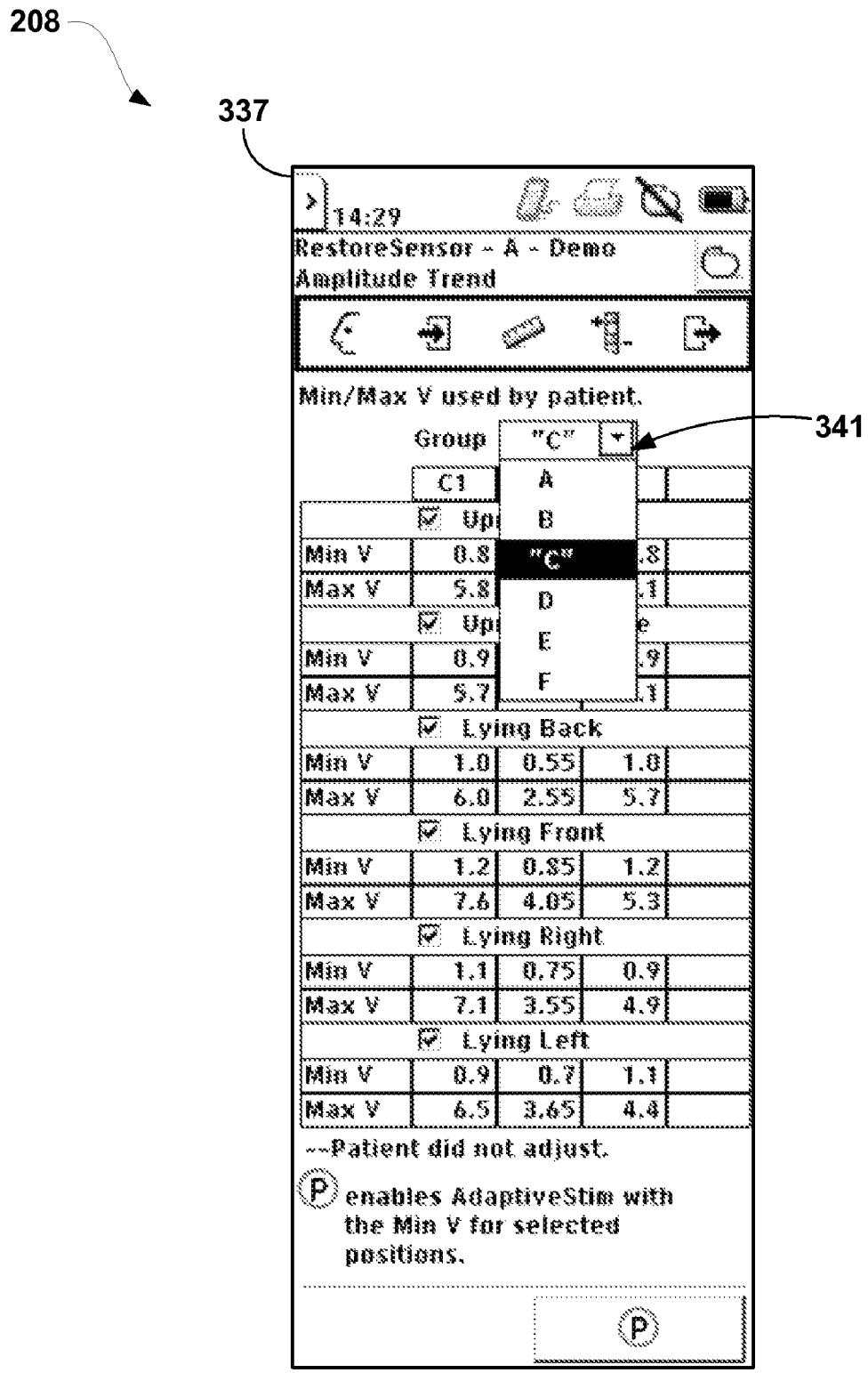

FIGS. 24A and 24B are conceptual diagrams illustrating example user interface 208 that provides maximum and minimum therapy adjustments associated with each posture state in screen 337. Screen 337 of FIG. 24A is similar to screen 336 of FIG. 23. As shown in FIG. 24A, screen 337 provides detailed adjustment information associated with FIG. 22. As shown in FIG. 23, screen 337 of user interface 208 has been accessed by the clinician via selection detail button 332 of screen 322 or some other menu option of user interface 208. Screen 337 presents therapy adjustment information 335 stored within IMD 14 during the record mode, including minimum and maximum amplitude settings selected by a user as adjustments to particular therapy programs when the patient occupied particular posture states. The clinician may select which group to view via group menu 341 and when to return to screen 322 by selecting return button 353. Return button 353 also programs stimulation therapy with the selected therapy values displayed in screen 337.

In the example of FIG. 24A, for each program (C1, C2, C3) of the selected program group (C), screen 337 presents posture states 343A (Upright), 343B (Upright and Mobile), 343C (Lying Back), 343D (Lying Front), 343E (Lying Right), and 343F (Lying Left), collectively posture state selections 343. Upright and Mobile may be similar to or the same as an Upright and Active posture state, described elsewhere in this disclosure. For each program in the selected group and each posture state selection 343A-343F, minimum amplitudes 347 and maximum amplitudes 349 are presented to the clinician. Therefore, the clinician may review the range of amplitudes used by patient 12 for a particular program when the patient occupied a particular posture state. As indicated by note 351, the user is reminded that selecting return button 353 enables posture responsive stimulation for each selected posture state of screen 337 using the respective minimum values of the amplitude settings. In other examples, screen 337 may present the number of therapy adjustments to each program in each posture state. Other information related to therapy adjustments and posture state information may also be presented in alternative examples of screen 337. If a therapy adjustment has not been made in a given program, then no minimum or maximum amplitude value will be provided in therapy adjustment information 335.

As an illustration, using screen 337, a user may view minimum and maximum voltage (Min V and Max V) settings for each of programs C1-C3 of the selected group C, and for each of several posture states. By selecting a posture state, e.g., by checking a box such as box 345 for the Upright posture, the user may indicate whether posture-responsive stimulation (AdaptiveStim) should be delivered with the Min V amplitude setting indicated for the posture state and program. If the patient selects Upright, by checking box 345, and then selects button 353, posture-responsive therapy will be delivered with the Min V amplitude setting indicated for each of the programs C1-C3 when the patient is determined to be in the Upright posture state. By checking all posture states, the pertinent Min V amplitude settings may be delivered for each of programs C1-C3 when the patient is determined to be in the pertinent posture state.

If the user has selected the Upright posture state and then activated button 353, the IMD 14 will be programmed to deliver stimulation with a voltage amplitude of 0.8 volts for the C1 program, 1.05 volts for the C2 program, and 0.8 volts for the C3 program when the patient is in the Upright posture state and the selected program group is group C. Likewise, for any other postures that the user has selected, upon activation of button 353, the programmer will be configured to program the IMD 14 to deliver applicable minimum voltage amplitudes of the programs in the selected group when the patient is in the specified posture states. Again, in this manner, the minimum voltage settings selected patient when a particular program group was applied for a particular posture state will thereafter be applied when the program group is applied and the patient again resides in the posture state. Hence, each posture state will have its own amplitude settings for programs in different program groups, and the amplitude settings are selected based on the minimum settings manually entered by the patient for the programs when the patient was in the posture state.

In other examples, the therapy adjustment information may be arranged differently on screen 337. For example, any unadjusted posture states may be removed from screen 337 because patient 12 has not used those posture states. Alternatively, therapy adjustment information may include a mean or median amplitude for each program and posture state selection 343. Further, upon the selection of an amplitude within therapy adjustment information 335, user interface 208 may display additional data, such as each therapy adjustment, the time and date stamp of each adjustment, the average adjustment for each day within the last week, month, year, or entire therapy, or any other detailed amplitude information. In some examples, therapy adjustment information 335 may provide adjustments to other therapy parameters, such as pulse width, pulse rate, or electrode configuration. Of course, any therapy adjustment information 335 related to drug delivery therapy and IMD 26 may be presented to the clinician if drug delivery is used instead of or in addition to electrical stimulation therapy.

FIG. 24B illustrates how the user may select a desired group of therapy programs within screen 337 of user interface 208. Upon selection of the down arrow of group menu 341, user interface 208 provides the list of all available therapy groups (e.g., A, B, C, etc.). As shown in FIG. 24B, Group C is identified as the current group that defines stimulation therapy. Upon the selection of the desired group from group menu 341, screen 337 changes to show therapy adjustment information associated with the selected group, including minimum and maximum voltage settings for the programs in the selected group when the patient occupied different posture states.

Figure 25A:
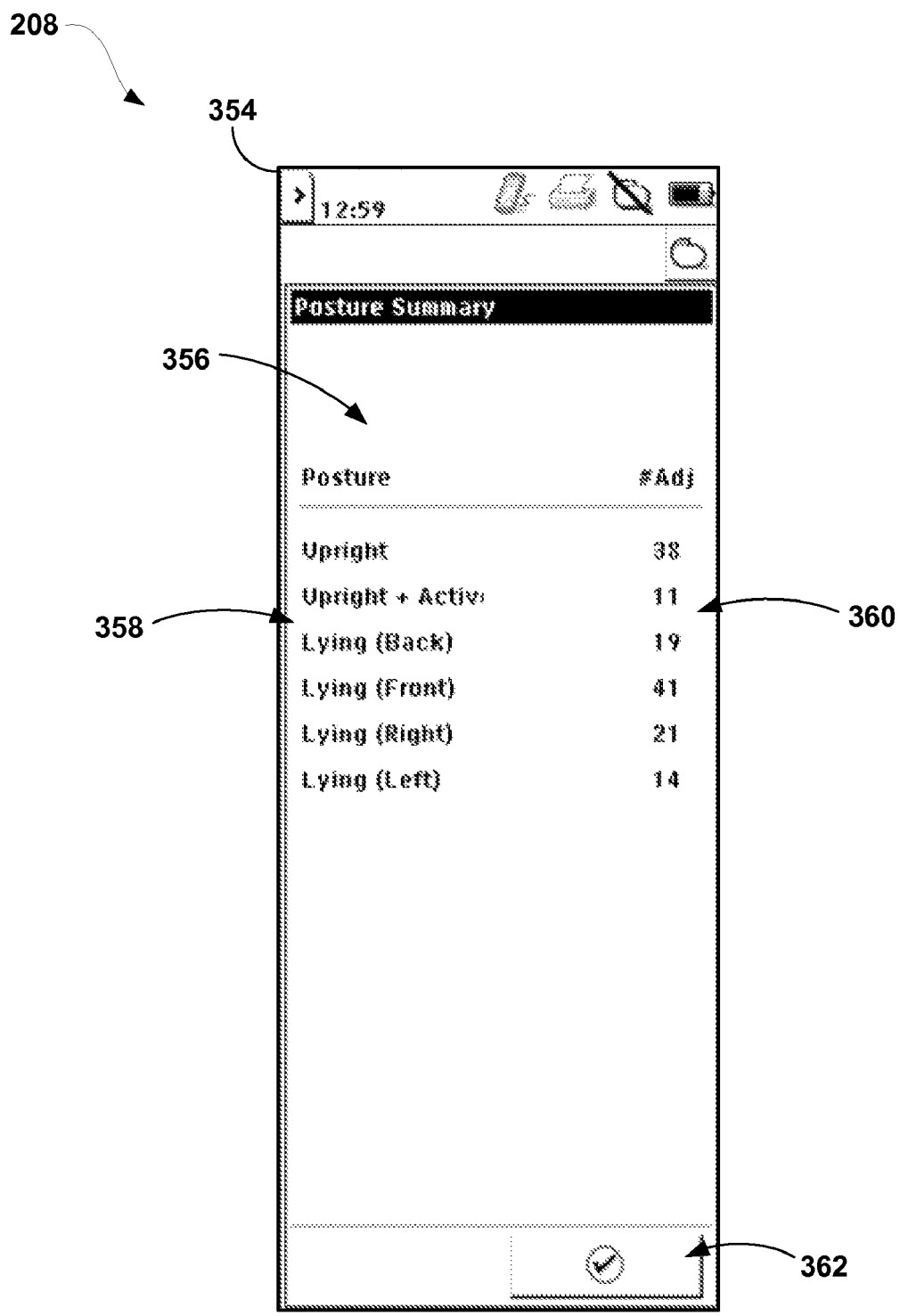
FIG. 25A is a conceptual diagram illustrating an example user interface showing quantified therapy adjustments for each posture state.

FIG. 25A is a conceptual diagram illustrating an example user interface 208 showing quantified therapy adjustments 356 for each posture state 358. Although therapy adjustments 356 shows as cumulative of all therapy programs, in other examples, screen 354 may only present adjustments for programs in a specified therapy group indicated on screen 354. Hence, user interface 208 may present the total number of adjustments for each posture state for all programs delivered while the patient was in the posture state, or show the total number of adjustments for each posture state for each program group delivered while the patient was in the posture state. As shown in FIG. 25A, screen 354 of user interface 208 is navigated to by the clinician via selection of summary button 320 of screen 302, detail button 332 of screen 322, or some other menu option provided by user interface 208. Screen 354 includes quantified therapy adjustments 356 that include posture states 358 and a corresponding adjustment value 360.

For each of the posture states 358, the clinician may desire to view how many therapy adjustments were made during the previous time interval or previous therapy session. Therefore, adjustment values 360 provide the total number of therapy adjustments associated with each of the posture states sensed by IMD 14. Adjustment values 360 may be a total number of adjustments during therapy, or an average number of adjustments per hour, day, week, month, or any other time interval that may or may not be selectable by the clinician. In addition, adjustment values 360 may be averaged over a certain time period by estimating the number of days or weeks over the therapy session of interest. In the example of FIG. 25A, the number of adjustments for the Upright, Upright and Active, Lying Back, Lying Front, Lying Right and Lying Left posture states were 38, 11, 19, 41, 21, and 14, respectively, for a given period.

The quantified therapy adjustments 356 may be useful to the clinician in determining posture states 358 for which patient 12 must manually adjust more often. Fewer adjustments may indicate that patient 12 is manually finding effective therapy often, while greater adjustments may indicate that patient 12 may be having difficulty manually finding therapy parameters that define effective therapy. These may be the appropriate inferences when the range of therapy adjustments indicates a large range of adjustments, e.g., a large range of voltage or current amplitudes. When the quantified number of adjustments indicated by adjustment value 360 is high, the clinician may desire to modify one or more programs to find a different set of therapy parameters that better treat patient 12, including parameters such as pulse width, pulse rate, electrode combination and electrode polarity. In this case, amplitude adjustments alone may be insufficient to provide effective therapy. In addition, screen 354 may provide trend information that shows if patient 12 has been making more or fewer adjustments over time. For example, screen 354 may present a graph or numerical representation of the trend data. The clinician may then adjust the program therapy parameters accordingly. Once the clinician is finished viewing screen 354, selection of return button 362 may bring the clinician back to a previous screen or to a home screen or main menu of clinician programmer 60.

As discussed above, a large number of adjustments may indicate a lack of efficacy when the range of adjustments is large. When the patient receives stimulation that is not posture state-responsive, a large number of adjustments over a small range of adjustments may indicate a situation in which posture state-responsive stimulation should be activated for the patient. In particular, if posture state-responsive stimulation is not enabled, the number of patient therapy adjustments during delivery of regular stimulation is large, and the range of patient therapy adjustments is small, the patient 12 may be a very good candidate for delivery of posture state-responsive stimulation therapy. As an illustration, if patient 12 makes numerous adjustments in a narrow voltage amplitude range of a 4.8 to 5.2 volts for a given posture state, then delivery of posture state-responsive therapy may be desirable for that posture state.

Figure 25B:
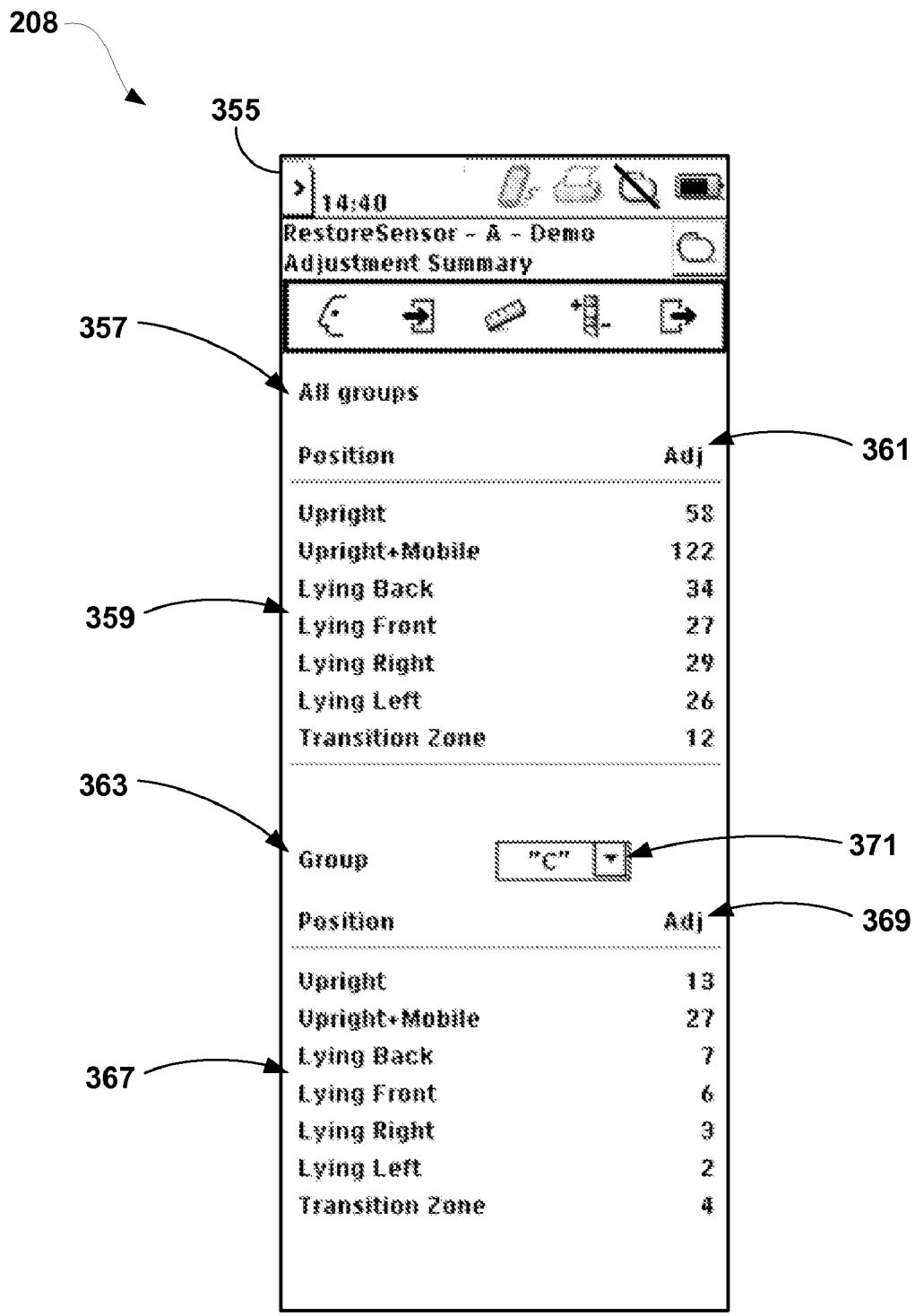
FIG. 25B is a conceptual diagram illustrating an example user interface showing quantified therapy adjustments for each posture state in all groups and a specified group.

FIG. 25B is a conceptual diagram illustrating an example user interface 355 showing quantified therapy adjustments 357 and 363 for each posture state in all groups and a specified group, respectively. Therapy adjustments 357 are provided as a cumulative value for adjustments made during therapy according to all program groups. Therefore, adjustments 361 provides a value for the number of adjustments made while patient 12 was engaged in each of posture states 359, regardless of which program was being used to deliver therapy. The value provided by adjustments 361 may be the number of adjustments over the most recent session, e.g., since the previous clinician visit, or during any other time period. Therapy adjustments 357 may allow the clinician to identify the posture states 359 for which patient 12 is having difficulty finding the appropriate stimulation therapy parameters. Again, large number of adjustments over a large range may indicate that the patient 12 is having difficulty in tuning the stimulation for the posture, whereas a large number of adjustments over a small range may indicate that posture state-responsive therapy is a good fit for the patient for the given posture state.

Quantified therapy adjustments 363 present adjustments that patient 12 has made only during therapy delivered by the selected program group shown in group menu 371. As shown in FIG. 25B, screen 355 presents the number of adjustments 369 for each posture state 367. The user may view therapy adjustments for other program groups by selecting a different group from group menu 371. Therapy adjustments 363 may allow the clinician to identify which group is best tailored to treat patient 12 by identifying the least number of adjustments. Adjustments 369 may provide values that are normalized to the length of time patient 12 received therapy with each group so that the clinician may make comparisons between program groups. In other embodiments, screen 355 may immediately present the group with the most adjustments 369 so that the clinician may begin remedying the ineffective therapy, e.g., by making adjustments to therapy parameters.

As discussed above, the number of patient therapy adjustments can be clustered, e.g., by application of a search timer whereby therapy adjustments that are closely spaced in time reset the search timer and result in a single, final therapy adjustment as the therapy adjustment that is associated with the posture state. In this manner, a number of closely spaced adjustments are presented as a single programming intervention event. Treatment of clustered adjustments as a single programming intervention event may be especially appropriate if the values of the adjustments are also close to one another. In some implementations, rather than clustering therapy adjustments that are received closely in time using a search timer or other technique, it may be desirable to associate all of the individual patient therapy adjustments with a posture state, even if the adjustments are temporally close to one another. Accordingly, some implementations may provide clustering of patient therapy adjustments, while other implementations may not.

Figure 26:
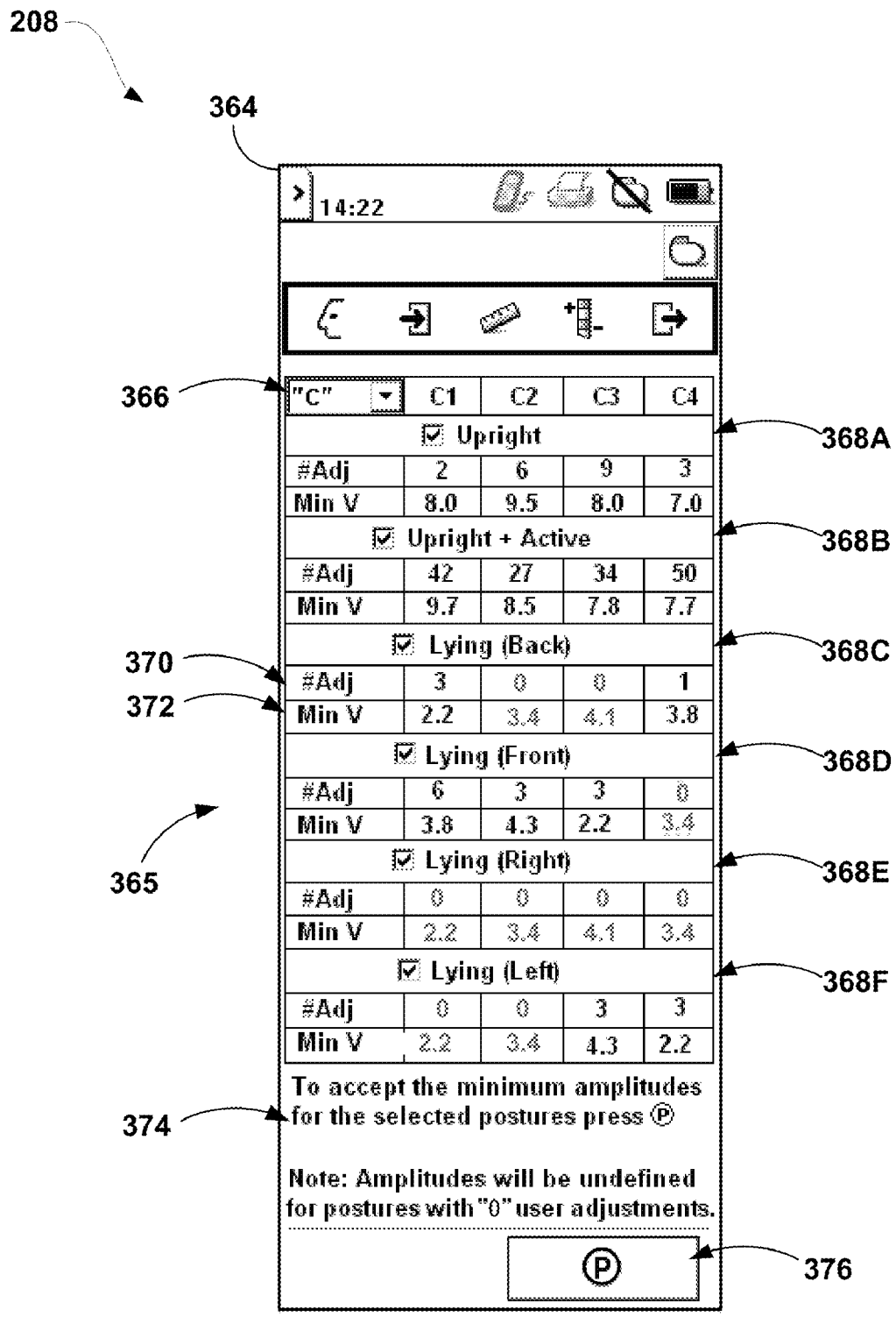
FIG. 26 is a conceptual diagram illustrating an example user interface showing stored adjustment information for all posture states of a program group to allow one-click programming.

FIG. 26 is a conceptual diagram illustrating an example user interface 208 showing quantified therapy adjustment information for all posture states of a program group to allow one-click programming. FIG. 26 is an alternative presentation of therapy adjustment information shown in FIGS. 19-21 or FIGS. 22-25. As shown in FIG. 26, screen 364 of user interface 208 presents therapy adjustment information 365 stored during the record mode of therapy. Screen 365 includes group menu 366, posture states 368A, 368B, 368C, 368D, 368E, and 368F (collectively "posture state selections 368"), adjustment values 370, minimum amplitudes 372, programming information 374, and confirmation button 376.

Once the clinician selects the desired group of programs in group menu 366 (e.g., group C), screen 364 presents the respective therapy adjustment information 365. Specifically, screen 364 provides an adjustment value 370 and minimum amplitude 372 for each of the programs and posture state selections 368. Again, the minimum amplitude 372 represents the minimum value specified by the patient when adjusting the amplitude of a program for a particular posture state. The adjustment value 370 is the number of times that patient 12 adjusted therapy for the specific program and posture state, and any non-adjustment is indicated with a zero and grayed out minimum amplitude 372. By a single click of confirmation button 376, the clinician may set the minimum amplitude as the nominal stimulation parameter to be delivered for each of the respective program and posture state combinations to be used subsequently during therapy. Therapy information 374 reminds the clinician on how to program therapy with confirmation button 376.

Figure 27:
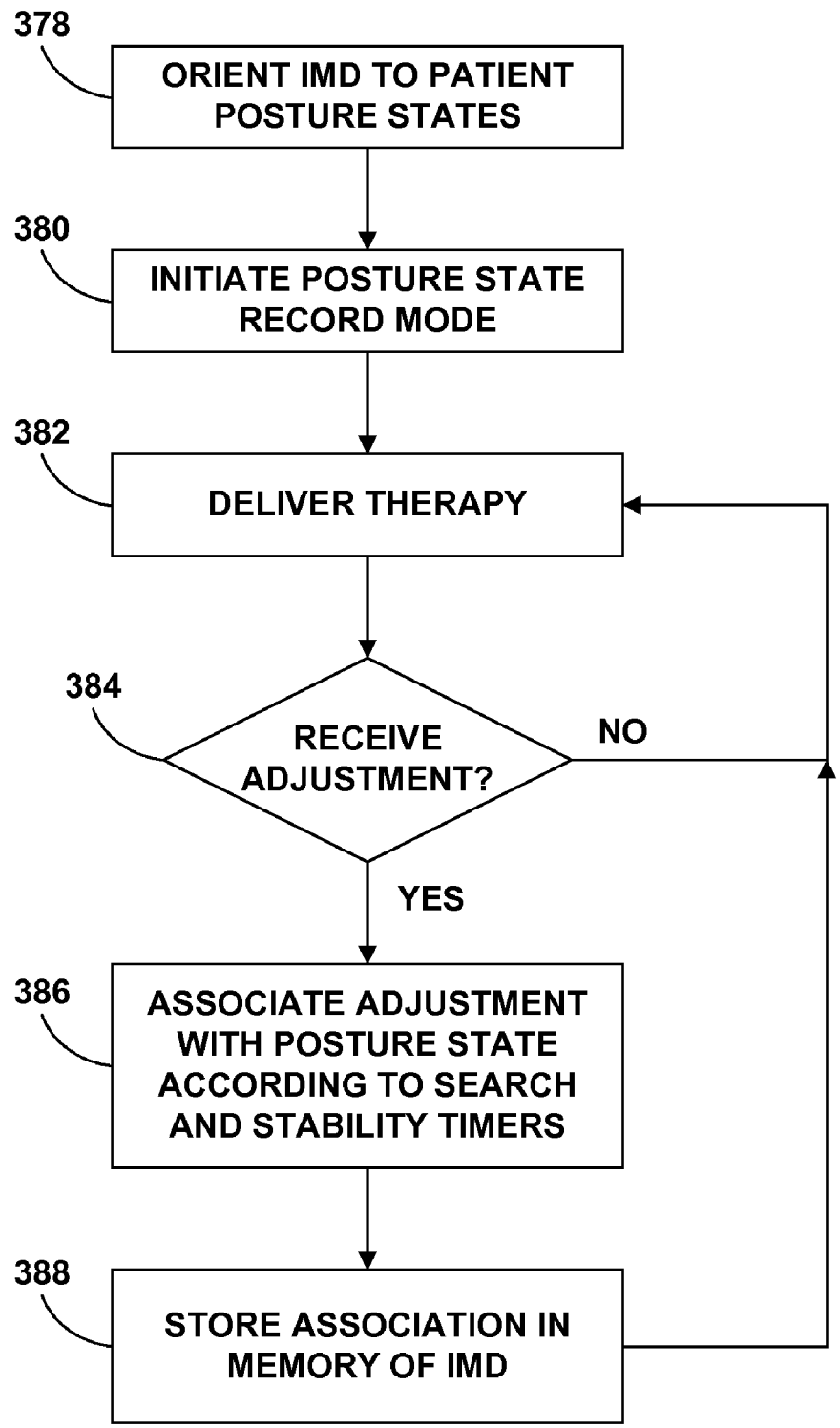
FIG. 27 is a flow diagram illustrating an example method for associating therapy adjustments with posture states during a record mode.

FIG. 27 is a flow diagram illustrating an example method for associating therapy adjustments with posture states during a record mode. As shown in FIG. 27, the clinician uses clinician programmer 60 to orient the posture state sensor in the IMD to posture states of patient 12 (378). For example, sensed vectors can be obtained for each of a plurality of posture states, and used as reference coordinate vectors either alone or to define posture state cones or other volumes, such as lying posture donut- or toroid-like volumes, as described in this disclosure. Next, clinician programmer 60 receives input to initiate the posture state record mode that associates therapy adjustments made by the patient to posture states (380). For example, when a sensed vector indicates a particular posture state, e.g., by reference to cones, vectors, or the like, and a patient makes a therapy adjustment, that therapy adjustment may be associated with the indicated posture state. After all other programming is completed, IMD 14 delivers therapy to patient 12 according to the therapy parameters stored as groups of programs (382).

If IMD 14 does not receive a therapy adjustment from patient 12 via patient programmer 30 (384), IMD 14 continues delivering therapy to patient 12 (382). However, if IMD 14 does receive a therapy adjustment from patient 12 via patient programmer 30 (384), processor 80 of IMD 14 associates the therapy adjustment with the appropriate posture state as determined by the posture search timer and the posture stability timer (386), or only the posture stability timer in other examples. In addition, IMD 14 may immediately modify the therapy based on the patient therapy adjustment, and deliver the therapy to the patient 12. Processor 80 then stores the association in memory 82 of IMD 14 (388) in addition to any other associates made for the same posture state. The stored association may be retrieved by an external programmer for viewing by a user such as a clinician, e.g., for use in analysis of therapeutic efficacy and programming of the IMD. IMD 14 then continues delivering therapy to patient 12 (382). Alternatively, patient programmer 30 may perform the associations and/or store the associations instead of IMD 14. A clinician programmer 60 may retrieve the associations from patient programmer 30.

As a refinement to the process of associating therapy adjustments with posture states during a record mode, IMD 14 and/or an external programmer 20 may be configured to apply a more stringent posture state detection requirement. A posture state detection process may detect a posture state based on any of the processes described in this disclosure, including those described with reference to FIGS. 8A-8C. As one example, a posture state may be detected if a sensed coordinate vector resides within a specified angle, cosine value, or distance of a particular reference coordinate vector for a particular posture state. However, a process for associating therapy adjustments with posture states may require that the sensed coordinate vector be located more closely to the reference coordinate vector. In this case, even if a particular posture is detected based on the location of the sensed coordinate vector within a first tolerance range of the reference coordinate vector, patient therapy adjustments are associated with the detected posture state only if the sensed coordinate vector is located within a second, tighter tolerance range of the reference coordinate vector. The second range for association is smaller than the first range for detection, requiring closer proximity of the sensed coordinate vector to the reference coordinate vector for an association to be made.

Hence, in this alternative implementation, IMD 14 or programmer 20 makes an association between a patient therapy adjustment and a posture state if a more stringent posture detection criteria is met. For example, in the example of a cone-based posture detection scheme, where each posture state is defined by a reference coordinate vector and a cone defining a tolerance angle, a patient may be detected as being in the face up posture state if he is plus or minus 30 degrees from the reference coordinate vector for the face up cone. For purposes of associating patient therapy adjustments with posture state, however, IMD 14 or programmer 20 makes the association only if the patient is detected in the face up posture state, and the patient is within plus or minus 15 degrees from the coordinate reference vector for the face up posture state cone.

In a toroid-based detection scheme, the patient would be classified as lying if he is greater than 60 degrees, for example, away from an upright reference coordinate vector or virtual upright reference coordinate vector. For purposes of association of patient therapy adjustments with posture states, however, IMD 14 or programmer 20 may be configured to only associate a therapy adjustment with a lying posture state if the patient is greater than 75 degrees, for example, from an upright reference coordinate vector or virtual upright reference coordinate vector. In each of these examples, in determining whether to associated patient therapy adjustments with posture states, IMD 14 or programmer 20 applies association criteria or logic with an increasing specificity applying a more conservative tolerance criteria than the posture state detection in general.

Figure 28:
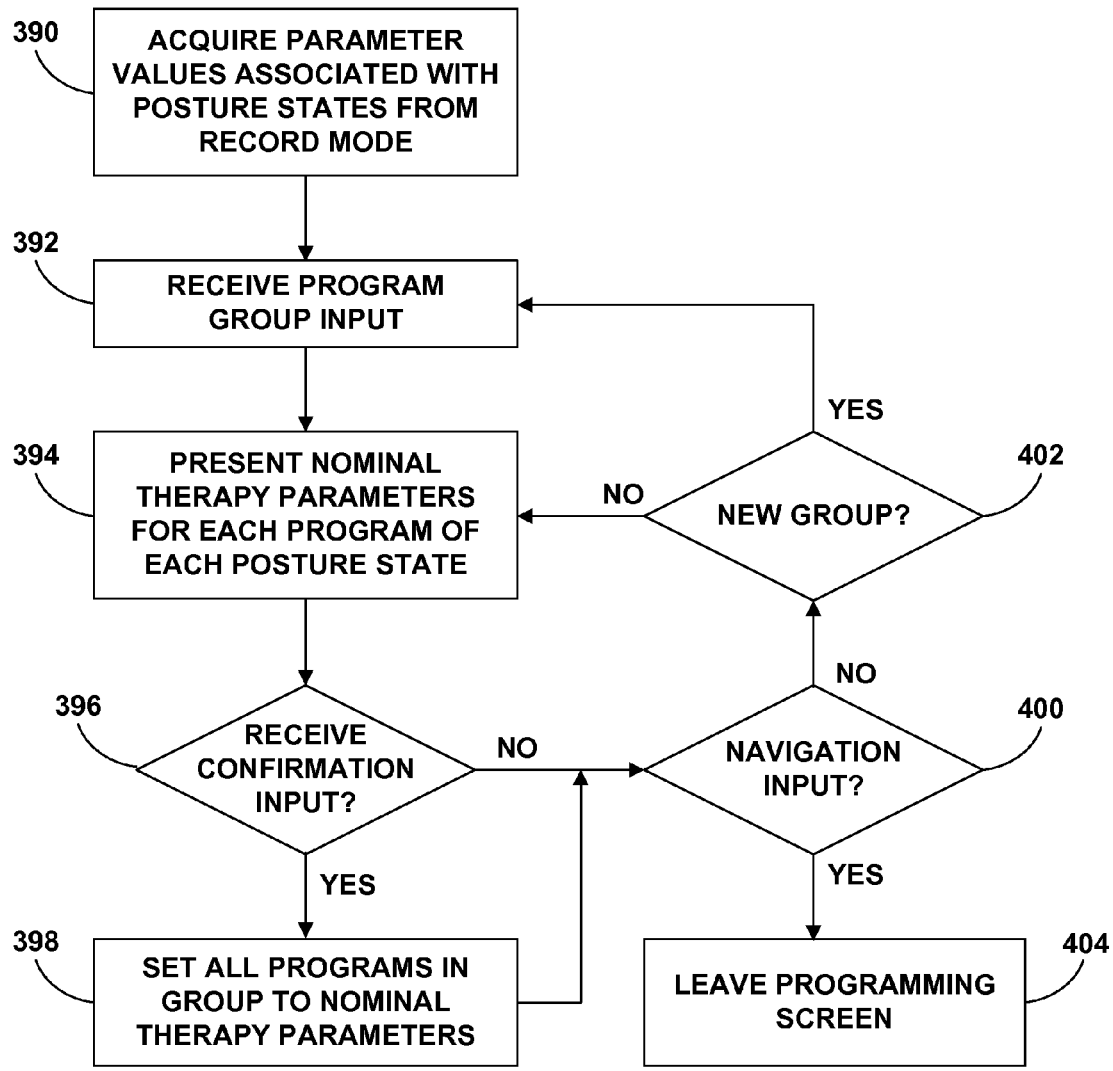
FIG. 28 is a flow diagram illustrating an example method for displaying suggested parameters and receiving an accept input from the user for one-click programming.

FIG. 28 is a flow diagram illustrating an example method for displaying suggested parameters and receiving a confirmation input from the user for one-click programming. Although clinician programmer 60 is described with respect to FIG. 28, any external programmer 20 may be used. As shown in FIG. 28, clinician programmer 60 first acquires the therapy adjustment information from IMD 14 or patient programmer 30, which includes parameter values associated with posture states during the record mode (390). Each parameter value represents the value of the parameter following a therapy adjustment by the patient. Next, user interface 208 of clinician programmer 60 receives group input from the group menu presented on user interface 208 (392). Processor 104 then commands user interface 208 to present the nominal therapy parameters for each program and posture state in a selected group based upon the therapy adjustments made by patient 12 (394). As described herein, the nominal therapy parameters may be a minimum amplitude, a maximum amplitude, the last used amplitude, or some other parameter selected from the therapy adjustment information.

If user interface 208 receives a confirmation input from the clinician accepting the nominal stimulation parameters to be set for all of the programs (396), then processor 104 sets all programs in the selected group according to the nominal therapy parameters for further use during delivery of automatic posture responsive stimulation (398). If there is a navigation input received by user interface 208 (400), the processor 104 commands user interface 208 to leave the programming screen (404) and continue programming. Otherwise, user interface 208 again presents the nominal therapy parameters (394) if there is no new group selected by the clinician (402), or user interface 208 detects that the clinician desires a new group selection (402) and receives the group input from the group menu (392). By presenting nominal values for each program in a group and for each posture state, a clinician may quickly select and apply the nominal values for use in posture-responsive therapy when the patient again occupies the pertinent posture states while the IMD is delivering the pertinent group of programs.

Figure 29:
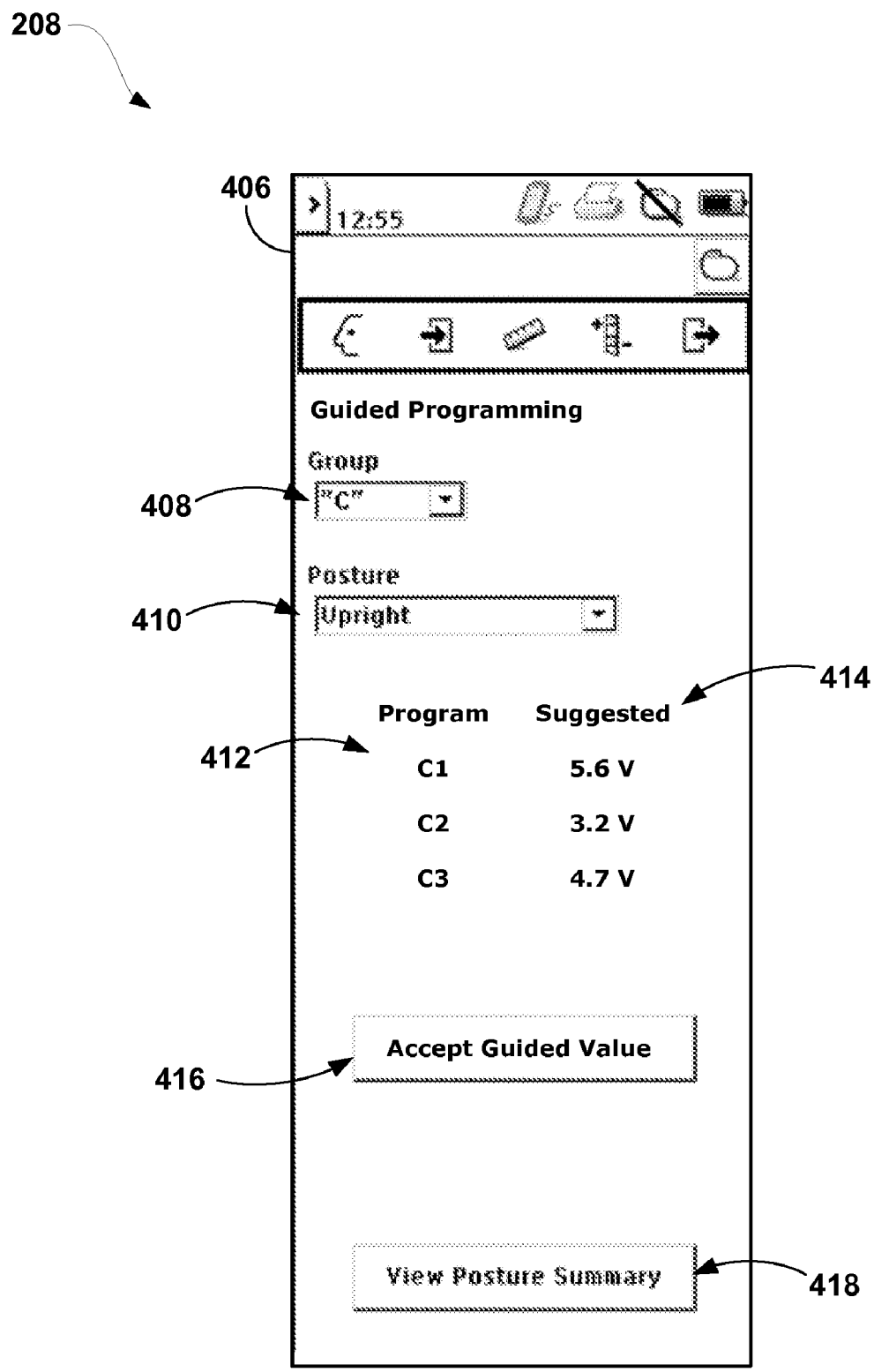
FIG. 29 is a conceptual diagram illustrating an example user interface presenting suggested therapy parameters for each program of a program group in guided programming.

FIG. 29 is a conceptual diagram illustrating an example user interface 208 presenting suggested therapy parameters for each program of a program group in guided programming. In general, a programmer receives therapy adjustment information that includes therapy adjustments made by a patient to at least one parameter of one or more stimulation therapy programs for one or more patient posture states, and generates one or more suggested therapy parameters for one or more of the stimulation therapy programs based on the therapy adjustment information. The suggested therapy parameters are presented to a user for selection in order to program therapy parameter values for posture states to support posture state-responsive therapy.

FIG. 29 is similar to FIG. 19, but screen 406 of FIG. 29 presents suggested therapy parameters to the clinician. Clinician programmer 60 is described, but any external programmer 20 may provide screen 406 to the user. Example user interface 208 shows suggested therapy parameters for each program in a group and allows guided programming with a single confirmation input. As shown in FIG. 29, screen 406 of user interface 208 presents suggested therapy parameters for each program, based upon the therapy adjustment information stored in IMD 14 and retrieved by clinician programmer 60. Screen 406 also includes group menu 408, posture state menu 410, programs 412, suggested therapy parameters 414, confirmation button 416, and summary button 418.

Group menu 408 allows the clinician to select the desired group of programs to be displayed on screen 406. Currently, the clinician has selected group "C," which is also the group currently selected (i.e., active) to deliver stimulation therapy because of the quotation marks around the group letter. Posture state menu 410 also allows the clinician to select the desired posture state so that the therapy adjustment information that is presented is related to the selected posture state. In FIG. 29, the clinician has selected the upright posture state in posture state menu 410.

Each of programs 412 (C1, C2, and C3) is presented with a suggested therapy parameter 414 that can be programmed for each of the programs 412. The suggested therapy parameter 414 may be generated by the programmer based upon the stored therapy adjustment information and a guided algorithm that is used to calculate the most appropriate therapy parameter for patient 12. The guided algorithm may be pre-programmed in memory 108 of clinician programmer 60 by the manufacturer or preselected by the clinician to best fit patient 12. The guided algorithm may use the therapy adjustment information to simply calculate the suggested therapy parameter 414 as a mean amplitude, median amplitude, or most frequently used amplitude from the therapy adjustments associated with the program and posture states, or the guided algorithm may perform more complex calculations. For example, processor 104 may calculate a weighted low amplitude value to attempt to generate a suggested therapy parameter that provided therapeutic stimulation without overstimulating patient 12. These and other guided algorithms are described further with reference to FIG. 30.

As an illustration, for a given program (e.g., C1_ and a given posture state (e.g., Upright), programmer 60 may compute a mean amplitude of all of the amplitudes selected by the patient for program C1 as a therapy adjustment when the patient was in the posture state. If there were four patient adjustments to program C1 in a given therapy session when the patient was in the Upright posture state, resulting in voltage amplitudes of 5.0 volts, 5.2 volts, 6.0 volts and 6.2 volts for program C1, then a mean voltage amplitude of 5.6 volts can be selected as the suggested amplitude to be automatically delivered when program C1 is applied as the patient is detected as residing in the Upright posture state. In addition to the mean value, programmer 60 may display the minimum and maximum values even if the user is only permitted to select the mean value. In this manner, the user can select the mean value as he suggested or guided value but still be able to conveniently observe the minimum and maximum values to understand where the guided value falls within the min-max range.

As another illustration, for a given program (e.g., C1_ and a given posture state (e.g., Upright), programmer 60 may determine a most frequently selected amplitude of all of the amplitudes selected by the patient for program C1 as a therapy adjustment when the patient was in the posture state. If there were ten patient adjustments to program C1 in a given therapy session when the patient was in the Upright posture state, resulting in voltage amplitudes of 5.0 volts, 5.2 volts, 6.0 volts, 6.0 volts, 6.0 volts, 5.8 volts, 4.8 volts, 5.5 volts, 6.0 volts, and 6.2 volts for program C1, then a most frequently selected voltage amplitude of 6.0 volts can be selected as the suggested amplitude to be automatically delivered when program C1 is applied as the patient is detected as residing in the Upright posture state.

With the suggested therapy parameters 414 presented to the clinician, screen 406 also may allow the clinician to make changes to the therapy parameters of each of the programs shown on screen 406. In the example of FIG. 29, the suggested therapy parameter is the mean amplitude of the values associated with recorded patient therapy adjustments for that posture state. The clinician may desire to set all of the programs of group "C" to their mean amplitude by selecting confirmation button 416 ("Accept Guided Value"), a confirmation input, only one time. In this manner, programming time and effort may be decreased because the clinician may only need a single click of confirmation button 416. Alternatively, the clinician may accept the guided value for individual programs rather than all programs at the same time. By selecting summary button 418, clinician programmer 60 will present additional posture state information or therapy adjustment information via user interface 208. The additional posture state information may include the total number of therapy adjustments associated with each posture state, as shown in FIGS. 25A and 25B.

Although screen 406 only shows the programs for one group at a time, alternative examples of user interface 208 may present more than one group of programs at one time. Then, the clinician may be able to set more suggested therapy parameters for multiple groups of programs with a single click of confirmation button 416. In other examples, the clinician may be able to select a global confirmation button (not shown) that sets the suggested therapy parameter for every program within IMD 14 with a single click of the global confirmation button.

Figure 30:
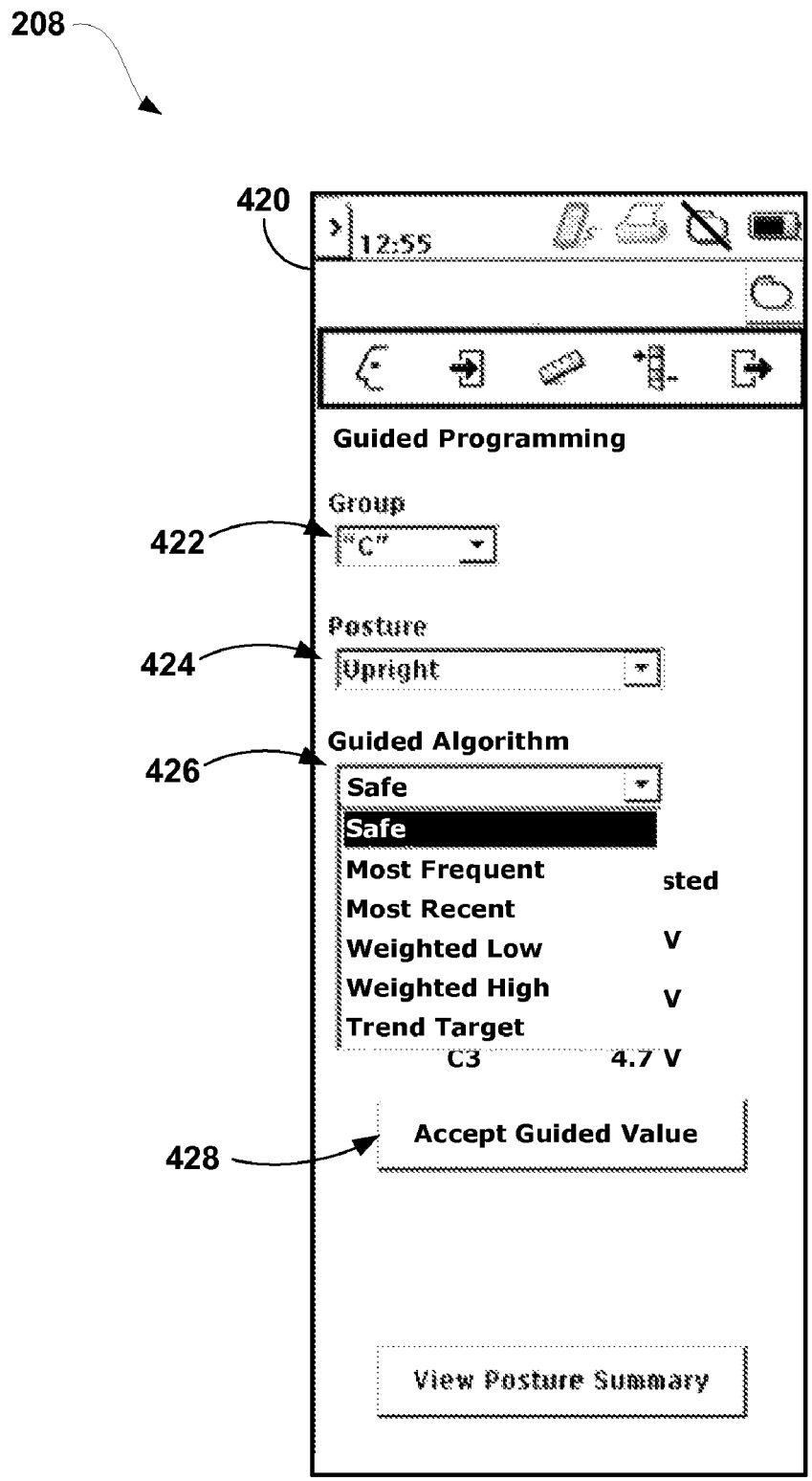
FIG. 30 is a conceptual diagram illustrating an example user interface showing different guided algorithms selectable by the user for guided programming.

FIG. 30 is a conceptual diagram illustrating an example user interface 208 showing different guided algorithms selectable by the user for guided programming. Screen 420 is similar to screen 406 of FIG. 29, but screen 420 allows the clinician to select a guided algorithm. As shown in FIG. 30, screen 420 includes group menu 422, posture state menu 424, guided algorithm menu 426, and confirmation button 428. Programs and suggested therapy parameters are not shown because they are covered by the drop-down portion of guided algorithm menu 426. As described previously, group menu 422 allows the selection of a group of programs and posture state menu 424 allows for the selection of a posture state. In addition, once suggested therapy parameters have been generated, the clinician may set all the programs to their respective suggested therapy parameters by a single selection confirmation button 428. However, guided algorithm menu 426 also allows the clinician to customize the method for generating the suggested therapy parameters.

Guided algorithm menu 426 may be populated with general guided algorithms for generating a suggested therapy parameter by the manufacturer, a technician, or the clinician. Guided algorithm menu 426 may include one or more guided algorithms. Generally, only one of the guided algorithms may be selected to generate the suggested therapy parameters for each group. Although the clinician may select the same guided algorithm for setting therapy parameters for each group of programs, the clinician may use different guided algorithms for different groups as needed.

Possible guided algorithms include a mean, a median, a safe average, a weighted low average, a weighted high average, a most frequent therapy parameter, a trend target, and a most recently used parameter. A safe average may be an average of the lowest half of the therapy parameters to prevent over stimulation. A weighted low average may average all therapy parameters used, but the lowest third of parameters are weighted double, for example. Conversely, a weighted high average may average all parameters used, but the highest third of parameters are weighted double, for example. The most frequent therapy parameter is just the most common parameter used by patient 12, while the most recent parameter is just the last used parameter for each program.

The trend target may be a guided algorithm that uses an average that weights more recently used therapy parameters while even rejecting therapy parameters that have not been used for a certain amount of time. The trend target may average each therapy parameter used, but only after reducing the weight of each parameter by a proportional number of days in the past it was used. For example, for each day old a therapy parameter was recorded, one percent of weight is reduced from the parameter prior to averaging. In this manner, a therapy parameter associated that day would have full weight, but a therapy parameter associated fifty days ago would only be given half weight. Therefore, the generated suggested therapy parameter will most resemble more recent therapy adjustments made by patient 12. A most recently used parameter algorithm may simply generate, as a suggested therapy parameter, a parameter value associated with a most recently received patient therapy adjustment.

In alternative embodiments, user interface 208 may provide a screen that allows the clinician to create new guided algorithms or modify currently stored guided algorithms. The guided algorithms may be stored by clinician programmer 60, patient programmer 30, IMD 14, or any other device. In some examples, clinician programmer 60 may even download new guided algorithms created by the manufacturer, a technician, or other clinicians over a network.

Figure 31:
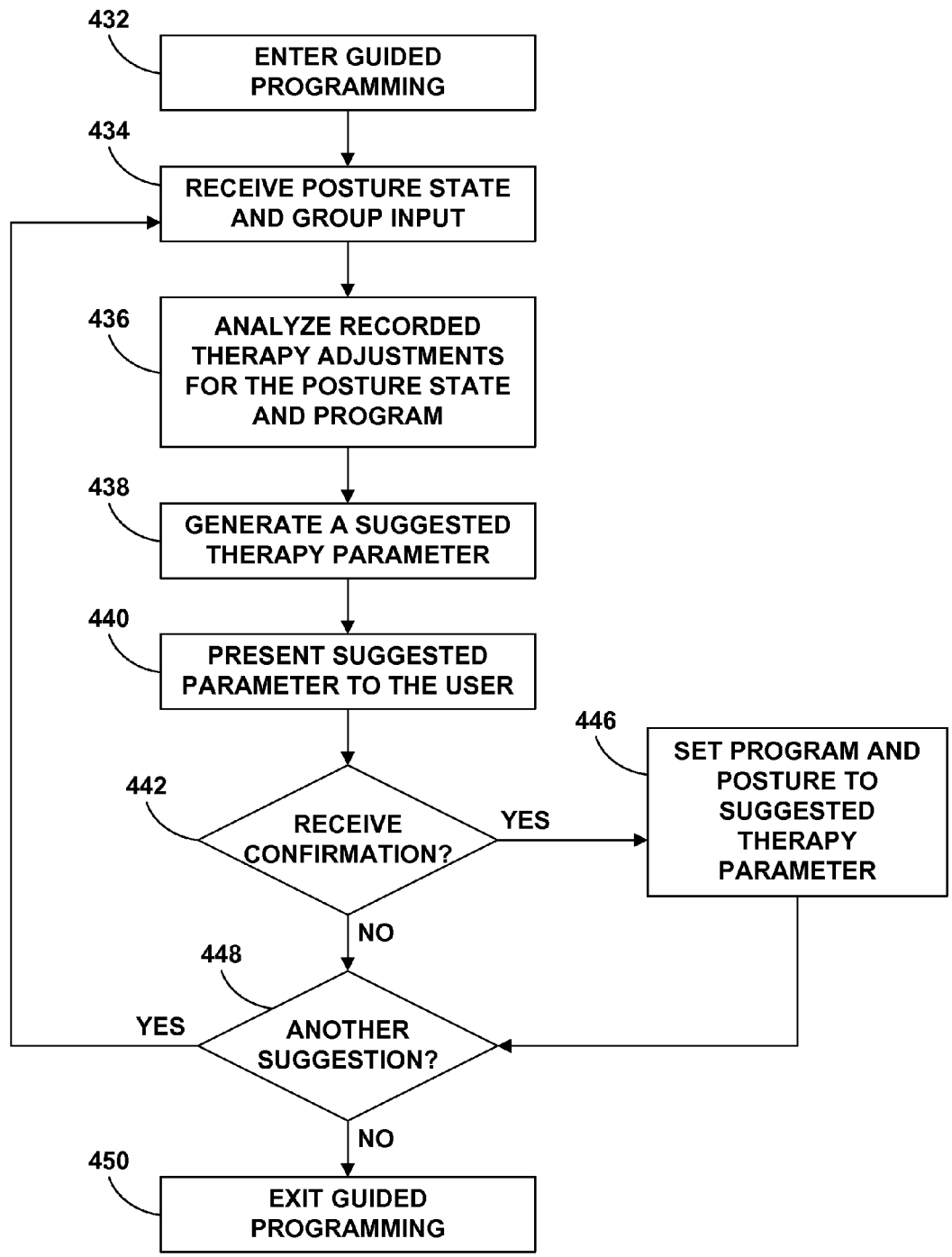
FIG. 31 is a flow diagram illustrating an example method for generating a suggested therapy parameter for each therapy program and receiving a confirmation input from the user.

FIG. 31 is a flow diagram illustrating an example method for generating a suggested therapy parameter for each therapy program and receiving a confirmation input from the user. Although clinician programmer 60 is described in FIG. 31, any external programmer 20 may function similarly. As shown in FIG. 31, clinician programmer 60 enters guided programming when requested by the clinician (432). Next, user interface 106 of clinician programmer 60 receives the posture state and group input that selects the desired group of programs and posture states (434). Next, processor 104 analyzes the stored therapy adjustment information for each posture state and program as stored during the record mode (436). In some examples, user interface 106 may also receive a guided algorithm input from the clinician that selects which guided algorithm processor 104 uses to generate the suggested therapy parameters.

Based on the guided algorithm set by the manufacturer or selected by the clinician, processor 104 generates a suggested therapy parameter for each of the plurality of programs (438). Next, user interface 106 presents the suggested therapy parameters to the clinician (440). If user interface 106 receives a confirmation input from the clinician to set the suggested therapy parameters to the programs (442), the processor 104 sets all the programs with the suggested therapy parameter (446) and determines if the clinician desires another suggestion (448). If user interface 106 does not receive a confirmation from the clinician (442), processor 104 waits to see if the clinician desires another suggestion (448). If the clinician desires more suggested therapy parameters (448), user interface 106 waits to receive the posture state input and the group input from the clinician (434). Otherwise, processor 104 exits the guided programming screen (450).

Figure 32:
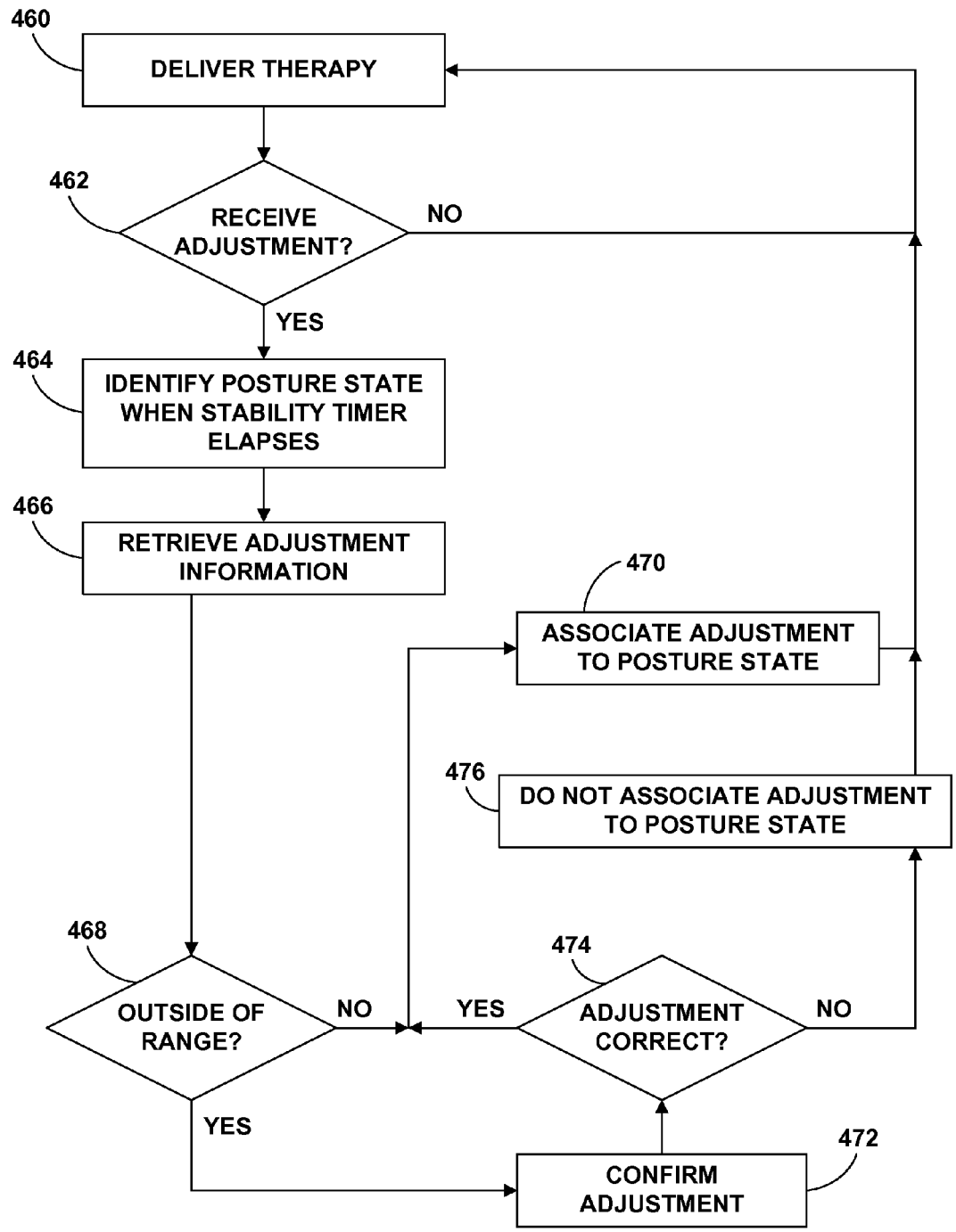
FIG. 32 is a flow diagram illustrating an example method for correcting a therapy adjustment associated with an unintended posture state.

FIG. 32 is a flow diagram illustrating an example method for correcting a therapy adjustment associated with an unintended posture state. In general, upon receiving a patient therapy adjustment to a parameter of a therapy program that defines electrical stimulation therapy delivered to the patient, and identifying a posture state of the patient, a programmer may associate the patient therapy adjustment with the posture state when the patient therapy adjustment is within a range determined based on stored adjustment information for the identified posture state.

Patient 12 may make an adjustment to a therapy parameter intending the adjustment for a specific posture state. However, the therapy adjustment may not be associated with the desired posture state because the transitions between posture states causes the stability period, and or search period, to fail to capture the desired posture state. The result in this circumstance is that a therapy adjustment may be associated with an unintended posture. IMD 14 and/or patient programmer 30 may be able to handle this exception to limit or prevent these unintended therapy adjustment associations. IMD 14 may automatically determine if the therapy adjustment should be associated with the identified posture state or IMD 14 may communicate with patient programmer 30 to prompt the user to confirm that the association is intended by patient 12 and is correct.

In the example of FIG. 32, IMD 14 delivers therapy to patient 12 (460) and continues to deliver therapy unless patient programmer 30 receives a therapy adjustment to a therapy parameter of the therapy program from patient 12 (462). If processor 104 of patient programmer 30 receives a therapy adjustment, processor 104 changes the therapy parameter according to the adjustment and then identifies the posture state of patient 12 once the stability period expires (464). In some examples, processor 104 of patient programmer 30 may cancel any association if the search period expires prior to expiration of the stability period, as described herein.

Once the posture state of patient 12 is identified, processor 104 retrieves the stored adjustment information from memory 108 for the therapy program and identified posture state (466). Processor 104 then analyzes the stored adjustment information, and if processor 104 determines that the received therapy adjustment is within a historical range of the stored adjustment information (468), processor 104 then associates the therapy adjustment with the identified posture state (470) and continues to deliver therapy (460). A historical range may be determined in a variety of ways.

If the received therapy adjustment is outside of the historical range of adjustments for the identified posture state (468), then processor 104 prompts patient 12 to confirm the association of the therapy adjustment to the identified posture state (472). If patient 12 confirms that the association is correct (474), then processor 104 associates the therapy adjustment to the posture state (470) and continues to deliver therapy (460). If patient 12 does not confirm the association, or rejects the association (474), then processor 104 does not associate the therapy adjustment to the identified posture state (476) before continuing to deliver therapy (460).

The historical range used by processor 104 to determine whether the received therapy adjustment should be associated with a posture state may vary based upon the therapy for patient 12 or the desires of the clinician. The historical range may be any range or threshold based upon the prior adjustments stored for the identified posture state. For example, the historical range may simply be bounded by the highest and lowest parameter values for the adjusted parameter. In other examples, the historical range may include an upper threshold or lower threshold to prevent an unintended parameter value association that could cause uncomfortable or even painful stimulation if posture responsive stimulation is enabled.

Alternatively, the historical range may be a calculated historical range that weights recent parameter adjustments greater than older parameter adjustments of the adjustment information made by patient 12 in the posture state. For example, previous patient adjustments can be divided into a lower set of patient adjustments and a higher set of patient therapy adjustments, e.g., as determined by parameter values associated with such adjustments, such as voltage or current amplitude An upper bound of the range may be set according to an average of the higher set of patient therapy adjustments, and a lower bound of the range may be set according to an average of the lower set of patient adjustments. If the prior patient therapy adjustments include amplitude values of 4.0, 4.2, 4.4, 5.0, 5.2, 5.6, 6.0 and 6.2 volts, for example, the upper bound could be computed as an average of the four largest values (5.2, 5.6, 6.0 and 6.2), and the lower bound could be computed as an average of the four lowest values (4.0, 4.2, 4.4, 5.0) In some cases, the lower and upper patient therapy adjustments may be weighted so that more recent patient therapy adjustments are weighted more heavily than less recent patient therapy adjustments in calculating the upper and lower bounds of the range. This weighted historical range would essentially limit the historical range to more recent parameter values used by patient 12. In each case, the range may be inclusive of at least a subset of the previous patient therapy adjustments for the program and the posture, but may be effective in avoiding unintended associations of outliers.

As another example, a range may be determined by determining an average, median or mean of previous patient therapy adjustments and then establishing threshold bounds above and below the average, median or mean. The thresholds may be symmetrical about the average, median or mean, or asymmetrical. If an average voltage amplitude is 5.0 volts, for example, lower and upper threshold bounds could be placed at 4.0 and 6.0 volts, and patient therapy adjustments outside of that range would be disregarded and not associated with pertinent program and posture state. In this case, the upper and lower bounds are placed symmetrically about the average. Alternatively, the upper and lower bounds could be placed asymmetrically such that one bound is closer to the average than the other bound.

In some cases, the threshold bounds may be computed as a percentage of the average. In the above example, the upper and lower bounds of 6.0 volts and 4.0 volts are plus/minus 20 percent of the average of 5.0 volts. As described above, in some cases, average may be an average of weighted values so that more recent patient therapy adjustments are weighted more heavily than less recent patient therapy adjustments in calculating the average, and ultimately the upper and lower bounds of the range, which may be centered or not centered about the average value. Again, this weighted historical range would limit the historical range to more recent parameter values used by patient 12.

Further, the historical range may be determined at least in part by a perception threshold and a pain threshold for the parameter predetermined by the clinician for patient 12. For example, the upper bound is set to be at or below a pain threshold and the lower bound is set to be at or above the perception threshold. In this case, patient therapy adjustments that result in parameter values below a perception threshold or above a pain threshold, each of which may be established in clinic, may be disregarded and not associated with a particular program and posture state, e.g., on the basis that such patient therapy adjustments may have been unintended for association with the posture state.

Any type of range may be used to trigger confirmation by patient 12 before an association is made, and the range may be set upon initialization of therapy or changed during stimulation therapy to patient 12. In any case, the historical range calculated by processor 104 is inclusive of therapy adjustments that would be acceptable for the particular identified posture state. For example, the range may be inclusive of at least a subset of previous therapy adjustments for the program and posture state. In some cases, the range could even allow for patient therapy adjustments that are within a predetermined margin outside of the previous patient therapy adjustments. Unacceptable therapy adjustments are those therapy adjustments that would not be desirable by patient 12 and/or outside of previously used therapy parameter values stored as the therapy adjustment information.

As described above, ranges to avoid unintended associations with programs and postures states may be computed, calculated, or otherwise determined in a variety of ways. Also, as new patient therapy adjustments are received, the range may be updated to take into account the values of the new patient therapy adjustments. In some cases, even though a new patient therapy adjustment falls outside of the current range, and therefore is not associated with a program and posture state (or at least requires patient confirmation to make the association), the new patient therapy adjustment could still be used to update the current range, i.e., as one of the values used to produce an average, weighted average or other range calculation.

In other examples, IMD 14 and/or patient programmer 30 may automatically remove unintended therapy adjustment associations without any input from patient 12. If the received therapy adjustment is outside of the historical range, processor 104, for example, may simply prevent that adjustment from being associated with the current program and identified posture state without requiring a confirmation from patient 12. In this manner, patient 12 may not be burdened by continually interacting with patient programmer 30. Alternatively, the therapy adjustments determined as unintended may be stored in a separate category such that the clinician may access the unintended therapy adjustments when reviewing the efficacy of therapy. Further, patient programmer 30 may prompt patient 12 to review how to adjust therapy or to visit the clinician after a certain number of unintended associations or a high frequency of unintended associations.

This disclosure may provide multiple features to a user. For example, implementing a posture search timer and a posture stability timer allows the system to correctly associate therapy adjustments to posture states even when the patient does not make the therapy adjustment while engaged in the intended posture state. Further, storing each association of therapy adjustments to posture states allows a clinician to review when the patient is adjusting stimulation therapy. This information may allow the clinician to modify the stimulation therapy in order to find the most effective therapy.

In addition, the disclosure provides a system that can use the associations between therapy adjustments and posture states in order to aid the clinician in quickly programming stimulation parameters for a plurality of therapy programs in a program group. For example, the system may set all therapy programs to the minimum amplitude used by the patient during stimulation therapy with one confirmation by the user. Moreover, the user interface may present a suggested parameter value for each of the therapy programs based upon the associations and a guide algorithm. In this manner, the user may select to confirm all suggested parameter values with one confirmation input in decrease the amount of time needed to program or modify the stimulation therapy.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to cause one or more processors to support one or more aspects of the functionality described in this disclosure.

In addition, it should be noted that the systems described herein may not be limited to treatment of a human patient. In alternative embodiments, these systems may be implemented in non-human patients, e.g., primates, canines, equines, pigs, and felines. These animals may undergo clinical or research therapies that my benefit from the subject matter of this disclosure.

Many embodiments of the invention have been described. Various modifications may be made without departing from the scope of the claims. These and other embodiments are within the scope of the following claims.

The invention claimed is:

1. A method comprising:
   detecting a patient adjustment to electrical stimulation therapy delivered to the patient;
   sensing a posture state of the patient; and
   associating the detected adjustment with the sensed posture state when the sensed posture state is sensed within a first period following the detection of the adjustment and when the sensed posture state does not change during a second period following the sensing of the sensed posture state.

2. The method of claim 1, further comprising:
   starting a posture search timer to time the first period in response to the detection of the adjustment; and
   starting a posture stability timer to time the second period in response to the sensing of the posture state.

3. The method of claim 1, further comprising restarting the posture timer when a new patient adjustment is detected before the end of the first period.

4. The method of claim 2, further comprising:
   restarting the posture stability time when the sensed posture state changes to a different posture state during the stability period; and
   associating the detected adjustment with the different posture state when the different posture state does not change during the second period following the sensing of the different posture state.

5. The method of claim 4, further comprising associating the detected adjustment with the different posture state when the different posture state does not change during the second period following the sensing of the different posture state and the posture stability timer is restarted before expiration of the first period.

6. The method of claim 1, wherein the first and second periods are equal.

7. The method of claim 1, wherein the first and second periods are different.

8. The method of claim 1, wherein the second period starts before an end of the first period and extends beyond the end of the first period.

9. The method of claim 1, wherein the first period is between approximately 30 seconds and 30 minutes, and the second period is between approximately 30 seconds and 30 minutes.

10. The method of claim 1, wherein the first period is between approximately 2 minutes and 4 minutes, and the second period is between approximately 2 minutes and 4 minutes.

11. The method of claim 1, further comprising storing the association in a memory of at least one of an implantable medical device or an external programmer for the implantable medical device.

12. A system comprising:
    a user interface configured to detect a patient adjustment to electrical stimulation therapy delivered to the patient;
    a posture state module configured to sense a posture state of the patient; and
    a processor configured to associate the detected adjustment with the sensed posture state when the sensed posture state is sensed within a first period following the detection of the adjustment and when the sensed posture state does not change during a second period following the sensing of the sensed posture state.

13. The system of claim 12, wherein the processor is configured to:
start a posture search timer to time the first period in response to the detection of the adjustment; and
start a posture stability timer to time the second period in response to the sensing of the posture state.

14. The system of claim 13, wherein the processor is configured to restart the posture search timer when a new patient adjustment is detected before the end of the first period.

15. The system of claim 13, wherein the processor is configured to:
restart the posture stability timer when the sensed posture state changes to a different posture state during the stability period; and
associate the detected adjustment with the different posture state when the different posture state does not change during the second period following the sensing of the different posture state.

16. The system of claim 15, wherein the processor is configured to associate the detected adjustment with the different posture state when the different posture state does not change during the second period following the sensing of the different posture state and the posture stability timer is restarted before expiration of the first period.

17. The system of claim 13, wherein the first and second period are equal.

18. The system of claim 13, wherein the first and second periods are different.

19. The system of claim 13, wherein the second period starts before an end of the first period and extends beyond the end of the first period.

20. The system of claim 13, wherein the first period is between approximately 30 seconds and 30 minutes, and the second period is between approximately 30 seconds and 30 minutes.

21. The system of claim 13, wherein the first period is between approximately 2 minutes and 4 minutes, and the second period is between approximately 2 minutes and 4 minutes.

22. The system of claim 13, further comprising an implantable medical device configured to deliver the electrical stimulation therapy, wherein the processor is configured to store the association in a memory of at least one of the implantable medical device or an external programmer for the implantable medical device, and wherein the processor is located in one of the implantable medical device or the external programmer.

23. A system comprising:
means for detecting a patient adjustment to electrical stimulation therapy delivered to the patient;
means for sensing a posture state of the patient; and
means for associating the detected adjustment with the sensed posture state when the sensed posture state is sensed within a first period following the detection of the adjustment and when the sensed posture state does not change during a second period following the sensing of the sensed posture state.

24. The system of claim 23, further comprising:
means for starting a posture search timer to time the first period in response to the detection of the adjustment; and
means for starting a posture stability timer to time the second period in response to the sensing of the posture state.

25. The system of claim 24, further comprising means for restarting the posture search timer when a new patient adjustment is detected before the end of the first period.

26. The system of claim 24, further comprising:
means for restarting the posture stability timer when the sensed posture state changes to a different posture state during the stability period; and
means for associating the detected adjustment with the different posture state when the different posture state does not change during the second period following the sensing of the different posture state.

27. The system of claim 26, further comprising means for associating the detected adjustment with the different posture state when the different posture state does not change during the second period following the sensing of the different posture state and the posture stability timer is restarted before expiration of the first period.

28. The system of claim 24, wherein the first and second period are equal.

29. The system of claim 24, wherein the first and second periods are different.

30. The system of claim 24, wherein the second period starts before an end of the first period and extends beyond the end of the first period.

31. The system of claim 24, wherein the first period is between approximately 30 seconds and 30 minutes, and the second period is between approximately 30 seconds and 30 minutes.

32. The system of claim 24, wherein the first period is between approximately 2 minutes and 4 minutes, and the second period is between approximately 2 minutes and 4 minutes.

33. The system of claim 24, further comprising means for storing the association in a memory of at least one of an implantable medical device or an external programmer for the implantable medical device.

34. An external programmer for an implantable medical device comprising:
a user interface configured to receive patient adjustments to electrical stimulation therapy delivered to the patient by the implantable medical device;
a telemetry interface configured to receive a sensed posture state from the implantable medical device and transmit the received adjustments to the implantable medical device;
a processor configured to associate the detected adjustment with the sensed posture state when the sensed posture state is sensed within a first period following the detection of the adjustment and when the sensed posture state does not change during a second period following the sensing of the sensed posture state; and
a memory configured to store the associations of the received adjustments with the sensed posture state.

35. An implantable medical device comprising:
a stimulation generator configured to deliver electrical stimulation therapy to a patient;
a telemetry interface configured to receive patient adjustments to the electrical stimulation therapy from an external programmer;
a posture sensing module configured to sense a posture state of the patient;
a processor configured to associate the received adjustments with the sensed posture state when the sensed posture state is sensed within a first period following the receiving of the adjustment and when the sensed posture state does not change during a second period following the sensing of the sensed posture state; and
a memory configured to store the associations of the received adjustments with the sensed posture state.

* * * * *